United States Patent
Wolleb et al.

(10) Patent No.: US 9,284,278 B2
(45) Date of Patent: *Mar. 15, 2016

(54) ELECTROLUMINESCENT METAL COMPLEX

(75) Inventors: Annemarie Wolleb, Fehren (CH); Heinz Wolleb, Fehren (CH)

(73) Assignee: BASF SE, Ludwigshafen (DE)

( * ) Notice: Subject to any disclaimer, the term of this patent is extended or adjusted under 35 U.S.C. 154(b) by 882 days.

This patent is subject to a terminal disclaimer.

(21) Appl. No.: 12/526,069

(22) PCT Filed: Feb. 4, 2008

(86) PCT No.: PCT/EP2008/051308
§ 371 (c)(1),
(2), (4) Date: Oct. 8, 2009

(87) PCT Pub. No.: WO2008/098851
PCT Pub. Date: Aug. 21, 2008

(65) Prior Publication Data
US 2010/0044688 A1    Feb. 25, 2010

(30) Foreign Application Priority Data
Feb. 14, 2007 (EP) ................. 07102336
May 7, 2007 (EP) ................. 07107611

(51) Int. Cl.
| | |
|---|---|
| *H01L 51/54* | (2006.01) |
| *C09K 11/06* | (2006.01) |
| *C07D 233/64* | (2006.01) |
| *C07F 15/00* | (2006.01) |
| *H05B 33/14* | (2006.01) |

(Continued)

(52) U.S. Cl.
CPC ............ *C07D 233/64* (2013.01); *C07D 233/90* (2013.01); *C07D 235/12* (2013.01); *C07D 235/30* (2013.01); *C07D 263/48* (2013.01); *C07D 263/56* (2013.01); *C07D 263/57* (2013.01); *C07D 263/58* (2013.01); *C07D 277/46* (2013.01); *C07D 277/66* (2013.01); *C07D 277/82* (2013.01); *C07F 15/0033* (2013.01); *C09K 11/06* (2013.01); *H01L 51/0085* (2013.01); *H05B 33/14* (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/5016* (2013.01)

(58) Field of Classification Search
USPC ....................................................... 548/106
See application file for complete search history.

(56) References Cited

U.S. PATENT DOCUMENTS

| | | |
|---|---|---|
| 6,335,334 B1 | 1/2002 | Schindler et al. |
| 6,420,057 B1 | 7/2002 | Ueda et al. |

(Continued)

FOREIGN PATENT DOCUMENTS

| | | |
|---|---|---|
| GB | 01345552 | 1/1974 |
| JP | 2000-355687 | 12/2000 |

(Continued)

OTHER PUBLICATIONS

Beilstein Reg. No. 522832, Jayanth et al. Indian J. Chem. vol. 11, 1973.
Beilstein Reg. No. 1106841, Chandramohan et al., Indian J. Chem. 10, 1972.
Beilstein Reg. No. 9995687, Wipf et al. Biomol. Che. vol. 3, No. 1, 2005.
Beilstein Reg. No. 5088040, Knoll et al., Synthesis, vol. 10, 1987.
Beilstein Reg. No. 5561334, Padmanabhan et al., Indian J. Chem. Sect. B, vol. 24, 1985.
Beilstein Reg. No. 5982172, Knoll et al., J. Prakt. Chem vol. 327, No. 3 1985.
Beilstein Reg. No. 1582752, Andrews et al., J. of the Chem. Soc, Sect. C, vol. 14, 1968.

(Continued)

*Primary Examiner* — Marie R. Yamnitzky
(74) *Attorney, Agent, or Firm* — Shruti Costales

(57) ABSTRACT

Metal complexes of the formula I or I' $[LDH]_n M[L]_m$ (I) $[LTH](M[L]_p)_2$ (II) wherein n is an integer 1 or 2, m and p each is an integer 1 or 2, the sum (n+m) being 2 or 3, M is a metal with an atomic weight of greater than 40 such as Iridium, L is a ligand as described in claim 1, and LDH is a bidentate ligand of the formula I1 and LTH is a dimer of LDH, binding to 2 metal atoms M, of the formula II' wherein W is selected from O, S, $NR_4$, $CR_5R_6$, X is N or $CR_7$, Y is selected from O, S, $NR_8$; and further residues are as defined in claim 1, show good light emitting efficiency in electroluminescent applications.

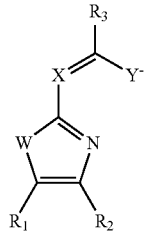

(II)

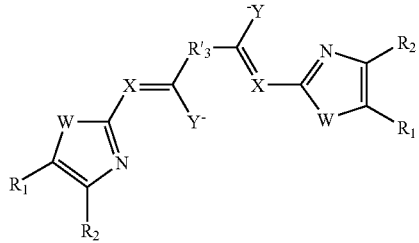

(II')

20 Claims, No Drawings

(51) Int. Cl.
*C07D 263/56* (2006.01)
*C07D 233/90* (2006.01)
*C07D 235/12* (2006.01)
*C07D 235/30* (2006.01)
*C07D 263/48* (2006.01)
*C07D 263/57* (2006.01)
*C07D 263/58* (2006.01)
*C07D 277/46* (2006.01)
*C07D 277/66* (2006.01)
*C07D 277/82* (2006.01)
*H01L 51/00* (2006.01)
*H01L 51/50* (2006.01)

(56) References Cited

U.S. PATENT DOCUMENTS

| | | | |
|---|---|---|---|
| 6,790,540 | B2 | 9/2004 | Mori et al. |
| 7,317,007 | B2 | 1/2008 | Alanine et al. |
| 7,820,828 | B2 * | 10/2010 | Schafer et al. ............. 548/108 |
| 8,080,667 | B2 * | 12/2011 | Schafer et al. ............. 548/108 |
| 8,492,749 | B2 * | 7/2013 | Pretot et al. ............. 257/40 |
| 2004/0065544 | A1 | 4/2004 | Igarashi et al. |
| 2004/0137267 | A1 * | 7/2004 | Igarashi et al. ............. 428/690 |
| 2008/0015355 | A1 | 1/2008 | Schafer et al. |
| 2008/0193700 | A1 | 8/2008 | Wolleb et al. |
| 2009/0062560 | A1 | 3/2009 | Pretot et al. |
| 2011/0114922 | A1 | 5/2011 | Pretot et al. |

FOREIGN PATENT DOCUMENTS

| | | |
|---|---|---|
| JP | 2001-076878 | 3/2001 |
| JP | 2001-139550 | 5/2001 |
| JP | 2002-338957 | 11/2002 |
| JP | 2003-535887 | 12/2003 |
| JP | 2006-152101 | 6/2006 |
| JP | 2007-099962 | 4/2007 |
| WO | 01/92437 | 12/2001 |
| WO | 2004/016221 | 2/2004 |
| WO | 2005/037845 | 4/2005 |
| WO | 2005/106868 | 11/2005 |
| WO | 2006/000544 | 1/2006 |
| WO | 2006/067074 | 6/2006 |

OTHER PUBLICATIONS

Beilstein Reg. No. 10281786 Frolov, et al., Izv. Akad. Nauk. Ser. Khim. vol. 5, 2005.

Beilstein Reg. No. 541860, Kamala et al., Indian J. Chem. Sect. vol. 22, No. 12, 1983.

Beilstein Reg. No. 4735029, Gompper et al. Angewandte Chemie, vol. 80, 1968.

Beilstein Reg. No. 9203869 Fahrni et al., J. Phys. Chem. vol. 106, No. 34, 2002.

Beilstein Registry No. 6154939 Tanaka et al., Chem. Pharm. Bull, vol. 40, No. 12, 1992.

Siegl, Walter; Journal of Organometallic Chemistry 107 (2), pp. C27-C30 (1976), and the Chemical abstract thereof, AN 1976:159027, (STN CAPLUS).

Abarghaz, M. et al., "Regioselective alkylation of the exocyclic nitrogen of heterocyclic amidines via the Mitsunobu reaction", Tetrahedron Letters, 1995, vol. 36, No. 36, pp. 6463-6466.

Sambaiah, T. and Reddy, K. K., "Synthesis of 2-aryl[1, 2, 4] triazolo[5, 1-b]benzoxazoles by oxidative cyclization of N-(benzoxazol-2-yl)benzamidines", Synthesis, 1990, vol. 5, pp. 422-424.

Angulo-Cornejo, J. et al.,"Metal chelates of N-benzothiazol-2-yl-, N-benzoxazol-2-yl- and N-(1H-benzimidazol-2-yl)-benzamide", Inorganica Chimica Acta, 2000, vol. 305, pp. 38-45.

Lazzaro, A. et al., "Synthesis, characterization, properties and structures of rhenium-(II), -(III), and -(V) complexes containing amino acids conjugated with a 2-aminothiazole ligand", Journal of the Chemical Society, Dalton Transactions, 2002, vol. 14, pp. 2843-2851.

Haga, M. and Tanaka, T., "Synthesis and properties of mixed-ligand ruthenium(II) complexes containing 2-(2-pyridyl) benzimidazole and related ligands", Chemistry Letters, 1979, vol. 7, pp. 863-864.

Keyes, T. E. et al., Redox and Spectroscopic Orbitals in Ru(II) and Os(II) Phenolate Complexes, Inorganic Chemistry, 2002, vol. 41, No. 22, pp. 5721-5732.

English language machine-generated translation for JP2006-152101 (233 pages); 2006.

English language machine-generated translation for JP2000-355687 (39 pages); 2000.

English language machine-generated translation for JP2002-338957 (37 pages); 2002.

English language machine-generated translation for JP2007-099962 (262 pages); 2007.

English language machine-generated translation for JP2001-076878 (88 pages); 2001.

English language machine-generated translation for JP2001-139550 (45 pages); 2001.

* cited by examiner

ELECTROLUMINESCENT METAL COMPLEX

The present invention relates to novel electroluminescent metal complexes, new intermediates (ligands) for their preparation, electronic devices comprising the metal complexes, and their use in electronic devices, especially organic light emitting diodes (OLEDs), as oxygen sensitive indicators, as phosphorescent indicators in bioassays, and as catalysts.

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of a voltage across the contact layers.

Organic electroluminescent compounds known for use as the active component in a light-emitting diode include metal complexes containing chelate ligands binding to the central metal atom via a carbon and a nitrogen atom (C,N-binding bidentate ligand; see, for example, [benzo]triazole ligands as of WO06/000544) or certain carbene ligands (C,C-binding) as disclosed in WO06/067074. Complexes of this class may further contain certain heteroatom-binding ligands such as those selected from derivatives of acetylacetonate, pyridyl-carboxylate, 1,1-bipyridine. Related ligand structures are also disclosed in US-2004-065544, WO05/106868, U.S. Pat. No. 6,420,057.

It has now been found that a certain class of heteroatom-binding bidentate ligands is especially useful for the preparation of electroluminescent metal complexes when combined with another (C,N- and/or C,C-binding) type of ligand. The invention therefore primarily pertains to a metal complex of the formula I or I'

$$[LDH]_n M[L]_m \qquad (I)$$

$$[LTH](M[L]_p)_2 \qquad (I')$$

wherein
n is an integer 1 or 2,
m and p each is an integer 1 or 2,
the sum (n+m) being 2 or 3,
M is a metal with an atomic weight of greater than 40,
L independently is a colour emission triggering moiety, consisting of 2 monodentate ligands or 1 bidentate ligand other than LDH or LTH;
LDH is a bidentate ligand of the formula II

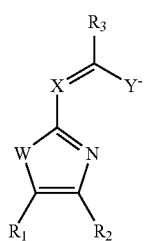

and LTH is a dimer of LDH, binding to 2 metal atoms M, of the formula II'

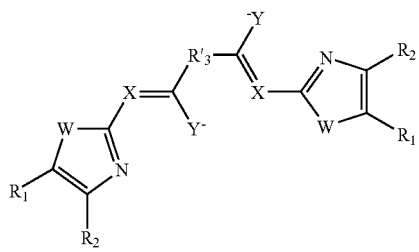

wherein
W is selected from O, S, $NR_4$, $CR_5R_6$,
X is N or $CR_7$,
Y is selected from O, S, $NR_8$;
$R_1$, $R_2$, $R_4$, $R_5$, $R_6$ independently are H, unsubstituted or substituted $C_1$-$C_{18}$alkyl, unsubstituted or substituted $C_2$-$C_{18}$alkenyl, unsubstituted or substituted $C_5$-$C_{10}$aryl, unsubstituted or substituted $C_2$-$C_{10}$heteroaryl, $C_1$-$C_{18}$acyl;
or $R_1$, $R_2$ may stand for a substituent selected from halogen, $C_1$-$C_{18}$alkoxy, $C_1$-$C_{18}$alkylthio, $C_1$-$C_{18}$acyl, $C_5$-$C_{10}$aryl, $C_3$-$C_{12}$cycloalkyl, $C_1$-$C_{18}$acyloxy, $C_5$-$C_{10}$aryloxy, $C_3$-$C_{12}$cycloalkyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R", PORR', PO(OR)R', $PO(OR)_2$, $PO(NHR)_2$, $PO(NRR')_2$, CN, $NO_2$, NHR, NRR', NH—NHR, NH—NRR', CONROH;

R, R' and R" independently are selected from $C_1$-$C_{12}$alkyl, $C_5$-$C_{10}$aryl, $C_3$-$C_{12}$cycloalkyl, preferably from $C_1$-$C_6$alkyl, phenyl, cyclopentyl, cyclohexyl;

and R may also be hydrogen;

or the neighbouring residues $R_1$ and $R_2$ form an organic bridging group completing, together with the carbon atoms they are bonding to, a carbocyclic or heterocyclic, non-aromatic or preferably aromatic ring of 5 to 7 ring atoms in total, which optionally may be substituted;

$R_7$, if present, together with its neighbouring residue $R_3$ forms an organic bridging group completing, with the carbon atoms they are bonding to, a carbocyclic or heterocyclic, non-aromatic or preferably aromatic ring of 5 to 7 ring atoms in total, which optionally may be substituted; or $R_7$ embraces the meanings given for $R_4$, or is halogen, OR, SR, NRR', COOR, CONRR', CN, OCN, SCN, or is $C_2$-$C_5$alkynyl, $C_3$-$C_5$cycloalkyl, hetero-$C_2$-$C_5$cycloalkyl, or $C_3$-$C_5$cycloalkenyl, each unsubstituted or substituted; or $R_3$ is H, unsubstituted or substituted $C_1$-$C_{18}$alkyl, unsubstituted or substituted $C_2$-$C_{18}$alkenyl, unsubstituted or substituted $C_5$-$C_{10}$aryl, unsubstituted or substituted $C_2$-$C_{10}$heteroaryl, $C_1$-$C_{18}$acyl, OR, SR, NRR', or is $C_2$-$C_5$alkynyl, $C_3$-$C_5$cycloalkyl, hetero-$C_2$-$C_5$cycloalkyl or $C_3$-$C_5$cycloalkenyl each unsubstituted or mono- or poly-substituted by COR, COOR, CONRR', CN, halogen and/or by OR;

$R'_3$ is unsubstituted or substituted $C_1$-$C_{18}$alkylene, unsubstituted or substituted $C_2$-$C_{18}$alkenylene, unsubstituted or substituted $C_5$-$C_{10}$arylene, unsubstituted or substituted $C_2$-$C_{10}$heteroarylene, $C_2$-$C_{18}$diacylene;

$R_8$ is hydrogen or a substituent.

In typical compounds, L independently is a moiety

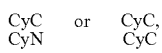

consisting of 2 monodentate ligands CyC and/or CyN, or 1 bidentate ligand wherein the 2 moieties CyC and CyN, or CyC and CyC, are interlinked by a chemical bond,
CyC is a an organic moiety containing a carbon atom bonding to M, and CyN is a cyclic organic moiety containing a nitrogen atom bonding to M,
and
LDH is a bidentate ligand of the formula II

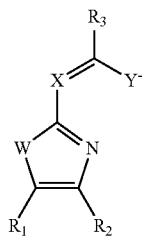

and LTH is a dimer of LDH, binding to 2 metal atoms M, of the formula II'

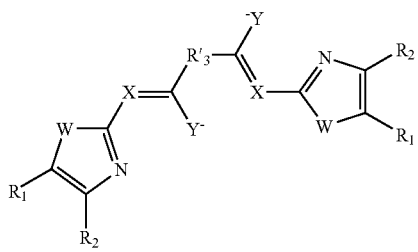

wherein
W is selected from O, S, $NR_4$, $CR_5R_6$,
X is N or $CR_7$,
Y is selected from O, S, $NR_8$;
$R_1$, $R_2$, $R_4$, $R_5$, $R_6$ independently are H, unsubstituted or substituted $C_1$-$C_{18}$alkyl, unsubstituted or substituted $C_2$-$C_{18}$alkenyl, unsubstituted or substituted $C_5$-$C_{10}$aryl, unsubstituted or substituted $C_2$-$C_{10}$heteroaryl, $C_1$-$C_{18}$acyl;
or $R_1$, $R_2$ independently may stand for a substituent selected from halogen, $C_1$-$C_{18}$alkoxy, $C_1$-$C_{18}$alkylthio, $C_1$-$C_{18}$acyl, $C_5$-$C_{10}$aryl, $C_3$-$C_{12}$cycloalkyl, $C_1$-$C_{18}$acyloxy, $C_5$-$C_{10}$aryloxy, $C_3$-$C_{12}$cycloalkyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R'', PORR', PO(OR)R', $PO(OR)_2$, $PO(NHR)_2$, $PO(NRR')_2$, CN, $NO_2$, NHR, NRR', NH—NHR, NH—NRR', CONROH;
R, R' and R'' independently are selected from $C_1$-$C_{12}$alkyl, $C_5$-$C_{10}$aryl, $C_3$-$C_{12}$cycloalkyl, preferably from $C_1$-$C_6$alkyl, phenyl, cyclopentyl, cyclohexyl;
and R may also be hydrogen;
or the neighbouring residues $R_1$ and $R_2$ form an organic bridging group completing, together with the carbon atoms they are bonding to, a carbocyclic or heterocyclic, non-aromatic or preferably aromatic ring of 5 to 7 ring atoms in total, which optionally may be substituted;
$R_7$, if present, together with its neighbouring residue $R_3$ forms an organic bridging group completing, with the carbon atoms they are bonding to, a carbocyclic or heterocyclic, non-aromatic or preferably aromatic ring of 5 to 7 ring atoms in total, which optionally may be substituted; and in case that W is O, $NR_4$, $CR_5R_6$ and/or Y contains a nitrogen atom, $R_7$ also embraces the meanings given for $R_4$;
or $R_3$ is H, unsubstituted or substituted $C_1$-$C_{18}$alkyl, unsubstituted or substituted $C_2$-$C_{18}$alkenyl, unsubstituted or substituted $C_5$-$C_{10}$aryl, unsubstituted or substituted $C_2$-$C_{10}$heteroaryl, $C_1$-$C_{18}$acyl;
$R'_3$ is unsubstituted or substituted $C_1$-$C_{18}$alkylene, unsubstituted or substituted $C_2$-$C_{18}$alkenylene, unsubstituted or substituted $C_5$-$C_{10}$arylene, unsubstituted or substituted $C_2$-$C_{10}$heteroarylene, $C_2$-$C_{18}$diacylene;
$R_8$ is hydrogen or a substituent.

The complexes of the invention show a number of advantageous features such as improved efficiency and high quantum yield in electroluminescent applications.

The moieties CyC and CyN in formula I and I' may be separate chemical entities (i.e. monodentate ligands) or preferably may be interconnected by a chemical bond (thus together forming a bidentate ligand). Ligands of these classes are well known in the art, see for example US-2004-265633; US-2006-172150; WO04/017043; WO06/067074; and documents mentioned further above. For example, the moiety CyC may be a ring A,

(alternatively named as ring D, see below) representing an optionally substituted aryl group which may contain a heteroatom,
or a group C,

representing a ligand is derived from a nucleophilic carbene, which may contain a heteroatom, and the moiety CyN may be a ring B,

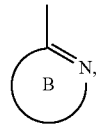

representing an optionally substituted nitrogen containing aryl group, which may contain a further heteroatom. In preferred ligands of these classes, 2 rings are interconnected, respectively, to form a bidentate ligand of the formula

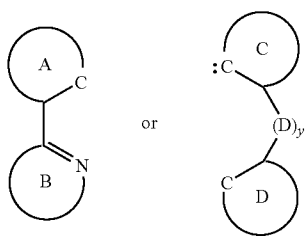

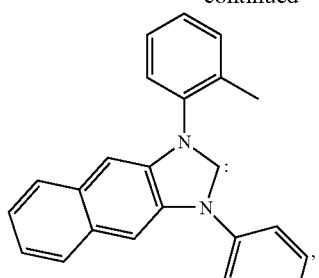

wherein
D is —C(=O)—, or —C($X^1$)$_2$—, wherein $X^1$ is hydrogen, or $C_{1-4}$alkyl, especially hydrogen, and y is 0, or 1, especially 0.

"Nucleophilic carbene ligand" in the context of the present invention means typical σ-donor ligands that can substitute classical 2e⁻ donor ligands. They can be cyclic or acyclic. They can have no or several different heteroatoms or several heteroatoms of the same kind. Possible carbenes are, for example, diarylcarbenes, cyclic diaminocarbenes, imidazol-2-ylidenes, imidazolidin-2-ylidene, 1,2,4-triazol-3-yildenes, 1,3-thiazol-2-ylidenes, acyclic diaminocarbenes, acyclic aminooxycarbenes, acyclic aminothiocarbenes, cyclic diborylcarbenes, acyclic diborylcarbenes, phosphinosilyl-carbenes, phosphinophosphonio-carbenes, sulfenyl-trifluormethylcarbenes, sulfenylpentafluorothiocarbenes etc.

Examples for bidentate ligands of this class include those of the formulae

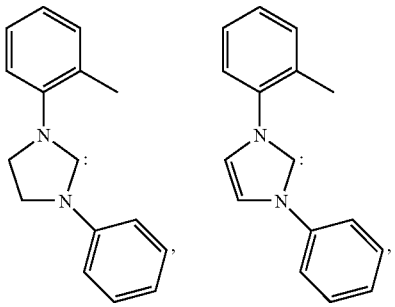

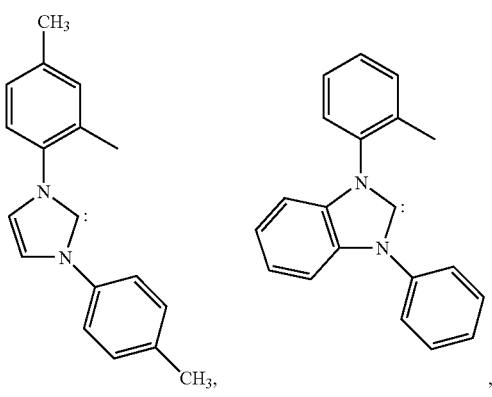

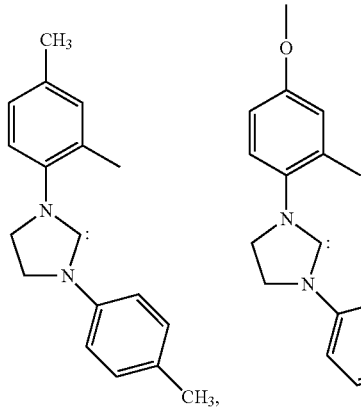

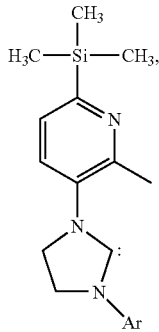

wherein the open bond indicates the carbon atom bonding to the central metal atom, the 2 dots (:) indicate the carbene bonding to metal, and Ar stands for an aryl group, e.g. phenyl or substituted phenyl such as 2,6-diisopropylphenyl. Further explanations for such carbene-type ligands and examples are given in WO06/067074, see passages from page 5, line 27, to page 11, line 16, which are hereby incorporated by reference.

The metal M is generally a metal M with an atomic weight of greater than 40, preferably the metal M is selected from Tl, Pb, Bi, In, Sn, Sb, Te, especially Mo, Cr, Mn, Ta, V, Cu, Fe, Ru, Ni, Co, Ir, Pt, Pd, Rh, Re, Os, Ag and Au. More preferably the metal is selected from Ir and Ru as well as Ag, Au, Pt and Pd, wherein Ir and Pt are most preferred.

If M is Co, or Fe, especially Ir, or Rh, (n+m) is preferably 3, especially where n is 1 and m is 2, and p is preferably 2.

If M is Ni, Rh, or Ru, especially Pd, or Pt, (n+m) is preferably 2 and p is preferably 1.

The above formulae II and II' only show one of the possible resonance/tautomeric forms of the novel ligand ("enol-form"), while other forms are possible as well, such as the one of the following formula II" ("keto-form"):

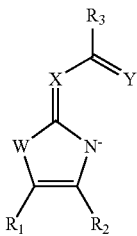
(II″)

or its dimer corresponding to present formula II', the predominant form mainly depending on the substitution pattern such as $R_3$ and X.

The bidentate ligand of the formula II or II″, or the tetradentate ligand of the formula II', usually bonds to the metal atom(s) by the N and Y atom(s) shown in the above structures. In case that W stands for a sulfur atom, however, a bond by the sulfur atom may replace the one by the nitrogen; corresponding conformations thus includes those of the below formulae IIa, IIb and IIc (with lines representing bonds to M, coordination bonds indicated by a dashed line, and electron pair bonds indicated by a straight line):

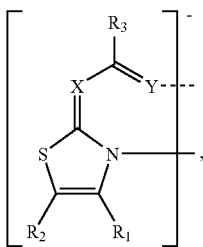
(IIa)

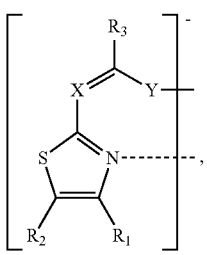
(IIb)

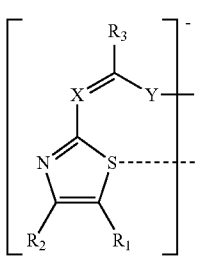
(IIc)

The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The term "facial" is intended to mean one isomer of a complex, $Ma_3b_3$, having octahedral geometry, in which the three "a" groups are all adjacent, i.e. at the corners of one triangular face of the octahedron. The term "meridional" is intended to mean one isomer of a complex, $Ma_3b_3$, having octahedral geometry, in which the three "a" groups occupy three positions such that two are trans to each other, i.e. the three "a" groups sit in three coplanar positions, forming an arc across the coordination sphere that can be thought of as a meridion. The phrase "adjacent to," when used to refer to layers in a device, does not necessarily mean that one layer is immediately next to another layer. The term "photoactive" refers to any material that exhibits electroluminescence and/or photosensitivity.

Any carbocyclic or heterocyclic, non-aromatic or preferably aromatic ring of 5 to 7 ring atoms in total formed by two neighbouring residues as an organic bridging group together with their anchor atoms often is selected from aryl, heteroaryl, cycloalkyl, or cycloaliphatic unsaturated moieties as explained below.

Substituents, if present, preferably are selected from halogen, $C_1$-$C_{18}$alkoxy, $C_1$-$C_{18}$alkyl, $C_2$-$C_{18}$alkenyl, $C_1$-$C_{18}$alkylthio, $C_1$-$C_{18}$acyl, $C_5$-$C_{10}$aryl, $C_4$-$C_{10}$heteroaryl, $C_3$-$C_{12}$cycloalkyl, $C_1$-$C_{18}$acyloxy, $C_5$-$C_{10}$aryloxy, $C_3$-$C_{12}$cycloalkyloxy, or from the residues COR, CH═NR, CH═N—OH, CH═N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R″, PORR', PO(OR)R', $PO(OR)_2$, $PO(NHR)_2$, $PO(NRR')_2$, CN, $NO_2$, NHR, NRR', NH—NHR, NH—NRR', CONROH;

where R, R' and R″ independently are selected from $C_1$-$C_{12}$alkyl, $C_1$-$C_{12}$haloalkyl, $C_5$-$C_{10}$aryl, $C_3$-$C_{12}$cycloalkyl, preferably from $C_1$-$C_6$alkyl, phenyl, cyclopentyl, cyclohexyl; and R may also be hydrogen.

$R_8$ may advantageously be selected from hydrogen, $C_1$-$C_{18}$alkyl, $C_2$-$C_{18}$alkenyl, $C_5$-$C_{10}$aryl, $C_4$-$C_{10}$heteroaryl, and electron pulling substituents such as $SO_2R'$, $SO_3R'$, $SO_2NHR'$, $SO_2NRR'$, $SO_2NH$—NHR', $SO_2NH$—NRR', $C_1$-$C_{18}$acyl, $C_1$-$C_8$haloalkyl, especially $SO_2R$ or $C_1$-$C_4$ perhaloalkyl such as $C_1$-$C_4$ perfluoroalkyl. Preferred $R_8$ (or $R_{20}$) are selected from H, $SO_2R$, COR', $C_1$-$C_8$alkyl, $C_2$-$C_8$alkenyl, unsubstituted or substituted phenyl, pyridyl; more preferably from H, $SO_2$—$R_{11}$, CO—$R_{11}$, where $R_{11}$ is $C_1$-$C_{12}$alkyl, $C_1$-$C_{12}$haloalkyl such as $CF_3$, phenyl, phenyl substituted by halogen.

Acyl stands for a residue of a sulfonic acid or especially organic carboxylic acid, which is formed formally by abstraction of the acid OH; examples are formyl, acetyl, propionyl, benzoyl. Generally, $C_1$-$C_{18}$ acyl stands for a radical X'—$R_{11}$, wherein X' is CO or $SO_2$ and $R_{11}$ is selected from monovalent aliphatic or aromatic organic residues, usually from molecular weight up to 300; for example, $R_{11}$ may be selected from $C_1$-$C_{18}$alkyl, $C_2$-$C_{18}$alkenyl, $C_5$-$C_{10}$aryl which may be unsubstituted or substituted by $C_1$-$C_8$alkyl or halogen or $C_1$-$C_8$alkoxy, $C_6$-$C_{15}$arylalkyl which may be unsubstituted or substituted in the aromatic part by $C_1$-$C_8$alkyl or halogen or $C_1$-$C_8$alkoxy, $C_4$-$C_{12}$cycloalkyl, and in case that X' is CO, $R_{11}$ may also be H. Acyl is preferably an aliphatic or aromatic residue of an organic acid —CO—$R_{11}$, usually of 1 to 30 carbon atoms, wherein $R_{11}$ embraces aryl, alkyl, alkenyl, alkynyl, cycloalkyl, each of which may be substituted or unsubstituted and/or interrupted as described elsewhere inter alia for alkyl residues, or R' may be H (i.e. COR' being formyl). Preferences consequently are as described for aryl, alkyl etc.; more preferred acyl residues are substituted or unsubstituted benzoyl, substituted or unsubstituted $C_1$-$C_{17}$alkanoyl or alkenoyl such as acetyl or propionyl or butanoyl or pentanoyl or hexanoyl, substituted or unsubstituted $C_5$-$C_{12}$cycloalkylcarbonyl such as cyclohexylcarbonyl.

The complex of formula I may carry a net charge, which is neutralized by suitable counterions, or the (formally positive) charge of its central atom M may be neutralized by the equivalent number of ligands (of formally negative charge), which is preferred.

In preferred complexes of the invention, the central atom M is obtained from a salt of a metal cation of charge 2+ (e.g. Pt2+) or especially 3+ (e.g. Ir3+,).

In complexes of special interest, n is 1 and m is 2.

Where aryl (e.g. in $C_1$-$C_{14}$-aryl) is used, this preferably comprises monocyclic rings or polycyclic ring systems with the highest possible number of double bonds, such as preferably phenyl, naphthyl, anthrachinyl, anthracenyl or fluorenyl. The term aryl mainly embraces $C_1$-$C_{18}$aromatic moieties, which may be heterocyclic rings (also denoted as heteroaryl) containing, as part of the ring structure, one or more heteroatoms mainly selected from O, N and S; hydrocarbon aryl examples mainly are $C_6$-$C_{18}$ including phenyl, naphthyl, anthrachinyl, anthracenyl, fluorenyl, especially phenyl. Heteroaryl such as $C_4$-$C_{18}$heteroaryl stands for an aryl group containing at least one heteroatom, especially selected from N, O, S, among the atoms forming the aromatic ring; examples include pyridyl, pyrimidyl, pyridazyl, pyrazyl, thienyl, benzothienyl, pyrryl, furyl, benzofuryl, indyl, carbazolyl, benzotriazolyl, thiazolyl, chinolyl, isochinolyl, triazinyl, tetrahydronaphthyl, thienyl, pyrazolyl, imidazolyl. Preferred are $C_4$-$C_{18}$aryl, e.g. selected from phenyl, naphthyl, pyridyl, tetrahydronaphthyl, furyl, thienyl, pyrryl, chinolyl, isochinolyl, anthrachinyl, anthracenyl, phenanthryl, pyrenyl, benzothiazolyl, benzoisothiazolyl, benzothienyl, especially $C_6$-$C_{10}$aryl; most preferred is phenyl, naphthyl.

Halogen denotes I, Br, Cl, F, preferably Cl, F, especially F.

Alkyl stands for any acyclic saturated monovalent hydrocarbyl group; alkenyl denotes such a group but containing at least one carbon-carbon double bond (such as in allyl); similarly, alkynyl denotes such a group but containing at least one carbon-carbon triple bond (such as in propargyl). In case that an alkenyl or alkynyl group contains more than one double bond, these bonds usually are not cumulated, but may be arranged in an alternating order, such as in —[CH═CH—]$_n$ or —[CH═C(CH$_3$)—]$_n$, where n may be, for example, from the range 2-50. Where not defined otherwise, preferred alkyl contains 1-22 carbon atoms; preferred alkenyl and alkinyl each contains 2-22 carbon atoms, especially 3-22 carbon atoms.

Where indicated as interrupted, any alkyl moiety of more than one, especially more than 2 carbon atoms, or such alkyl or alkylene moieties which are part of another moiety, may be interrupted by a heterofunction such as O, S, COO, OCNR10, OCOO, OCONR10, NR10CNR10, or NR10, where R10 is H, $C_1$-$C_{12}$alkyl, $C_3$-$C_{12}$cycloalkyl, phenyl. They can be interrupted by one or more of these spacer groups, one group in each case being inserted, in general, into one carbon-carbon bond, with hetero-hetero bonds, for example O—O, S—S, NH—NH, etc., not occurring; if the interrupted alkyl is additionally substituted, the substituents are generally not α to the heteroatom. If two or more interrupting groups of the type —O—, —NR10-, —S— occur in one radical, they often are identical.

The term alkyl, wherever used, thus mainly embraces especially uninterrupted and, where appropriate, substituted $C_1$-$C_{22}$alkyl such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. Alkoxy is alkyl-O—; alkylthio is alkyl-S—.

Haloalkyl denotes alkyl substituted by halogen; this includes perhalogenated alkyl such as perfluoroalkyl, especially $C_1$-$C_4$ perfluoroalkyl, which is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

Aralkyl is, within the definitions given, usually selected from $C_7$-$C_{24}$aralkyl radicals, preferably $C_7$-$C_{15}$aralkyl radicals, which may be substituted, such as, for example, benzyl, 2-benzyl-2-propyl, β-phenethyl, α-methylbenzyl, α,α-dimethylbenzyl, ω-phenyl-butyl, ω-phenyl-octyl, ω-phenyl-dodecyl; or phenyl-$C_1$-$C_4$alkyl substituted on the phenyl ring by one to three $C_1$-$C_4$alkyl groups, such as, for example, 2-methylbenzyl, 3-methylbenzyl, 4-methylbenzyl, 2,4-dimethylbenzyl, 2,6-dimethylbenzyl or 4-tert-butylbenzyl. or 3-methyl-5-(1',1',3',3'-tetramethyl-butyl)-benzyl.

The term alkenyl, wherever used, thus mainly embraces especially uninterrupted and, where appropriate, substituted $C_2$-$C_{22}$alkyl such as vinyl, allyl, etc.

$C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic cyclic moieties include cycloalkyl, aliphatic heterocyclic moieties, as well as unsaturated variants thereof such as cycloalkenyl. Cycloalkyl such as $C_3$-$C_{18}$cycloalkyl, is preferably $C_3$-$C_{12}$cycloalkyl or said cycloalkyl substituted by one to three $C_1$-$C_4$alkyl groups, and includes cyclopropyl, cyclobutyl, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred. $C_3$-$C_{12}$cycloalkyl includes cyclopropyl, cyclobutyl, cyclopentyl, cyclohexyl, cycloheptyl, cyclooctyl, cyclononyl, cyclodecyl, cycloundecyl, cyclododecyl; preferred among these residues are $C_3$-$C_6$cycloalkyl as well as cyclododecyl, especially cyclohexyl. Further ring structures occurring are heterocyclic aliphatic rings usually containing 5 to 7 ring members, among them at least 1, especially 1-3, heteromoieties, usually selected from O, S, NR10, where R10 is as explained above for interrupting NR10-groups; examples include $C_4$-$C_{18}$cycloalkyl, which is interrupted by S, O, or NR10, such as piperidyl, tetrahydrofuranyl, piperazinyl and morpholinyl. Unsaturated variants may be derived from these structures by abstraction of a hydrogen atom on 2 adjacent ring members with formation of a double bond between them; an example for such a moiety is cyclohexenyl.

Alkoxy such as $C_1$-$C_{24}$alkoxy is a straight-chain or branched radical, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_6$-$C_{18}$cycloalkoxy is, for example, cyclopentyloxy, cyclohexyloxy, cycloheptyloxy or cyclooctyloxy, or said cycloalkoxy substituted by one to three $C_1$-$C_4$alkyl, for example, methylcyclopentyloxy, dimethylcyclopentyloxy, methylcyclohexyloxy, dimethylcyclohexyloxy, trimethylcyclohexyloxy, or tert-butylcyclohexyloxy.

$C_6$-$C_{24}$aryloxy is typically phenoxy or phenoxy substituted by one to three $C_1$-$C_4$alkyl groups, such as, for example o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

$C_6$-$C_{24}$aralkoxy is typically phenyl-$C_1$-$C_9$alkoxy, such as, for example, benzyloxy, α-methylbenzyloxy, α,α-dimethylbenzyloxy or 2-phenylethoxy.

$C_1$-$C_{24}$alkylthio radicals are straight-chain or branched alkylthio radicals, such as e.g. methylthio, ethylthio, propylthio, isopropylthio, n-butylthio, isobutylthio, pentylthio, isopentyl-thio, hexylthio, heptylthio, octylthio, decylthio, tetradecylthio, hexadecylthio or octadecylthio.

Silyl such as SiRR'R" is preferably Si substituted by two or preferably three moieties selected from unsubstituted or substituted hydrocarbyl or hydrocarbyloxy (wherein the substituents are preferably other than substituted silyl), as defined above, or by unsubstituted or substituted heteroaryl. In case that Si carries only two substituents, the silyl group is of the type —SiH($R_2$) with $R_2$ preferably being hydrocarbyl or hydrocarbyloxy. Preferred hydrocarbyl(oxy) are $C_1$-$C_{20}$alkyl(oxy), aryl(oxy) such as phenyl(oxy), $C_1$-$C_9$alkylphenyl(oxy), where "(oxy)" stands for the optional linker "—O—" which may be present or not. More preferred are three $C_1$-$C_{20}$-alkyl or -alkoxy substituents, i.e. substituted silyl then is Si($R12$)$_3$ with R12 being $C_1$-$C_{20}$-alkyl or -alkoxy, especially three $C_1$-$C_8$-alkyl substitutents, such as methyl, ethyl, isopropyl, t-butyl or isobutyl.

In one embodiment, the present invention is directed to metal complexes comprising at least one ligand LDH or LTH as described above and at least one ligand as described in WO06/067074, such as one of the formula

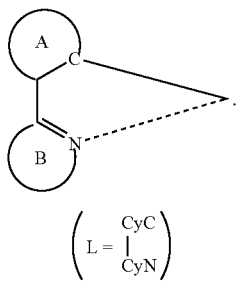

$$L = \begin{pmatrix} CyC \\ | \\ CyN \end{pmatrix}$$

Ring system B (hereinafter also referred to as pyridyl group, though not limited to pyridyl) in preferred ligands of this class includes a phenyl group, a substituted phenyl group, a naphthyl group, a substituted naphthyl group, a furyl group, a substituted furyl group, a benzofuryl group, a substituted benzofuryl group, a thienyl group, a substituted thienyl group, a benzothienyl group, a substituted benzothienyl group, and the like. The substitutent on the substituted phenyl group, substituted naphthyl group, substituted furyl group, substituted benzofuryl group, substituted thienyl group, and substituted benzothienyl group include $C_1$-$C_{24}$alkyl groups, $C_2$-$C_{24}$alkenyl groups, $C_2$-$C_{24}$alkynyl groups, aryl groups, heteroaryl groups, $C_1$-$C_{24}$alkoxy groups, $C_1$-$C_{24}$alkylthio groups, a cyano group, $C_2$-$C_{24}$acyl groups, $C_1$-$C_{24}$alkyloxycarbonyl groups, a nitro group, halogen atoms, alkylenedioxy groups, and the like.

In said embodiment the ligand

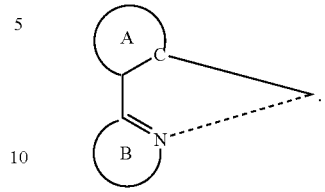 (L)

is more preferably a group of formula

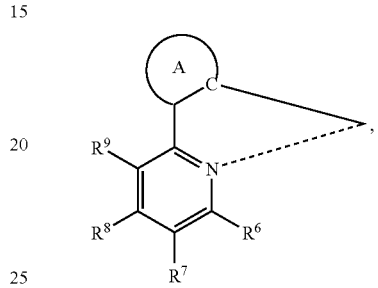

wherein $R^6$, $R^7$, $R^8$, and $R^9$ are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, acyl, alkyloxycarbonyl, a nitro group, or a halogen atom; or two substituents $R^6$, $R^7$, $R^8$, and $R^9$, which are adjacent to each other, together form a group

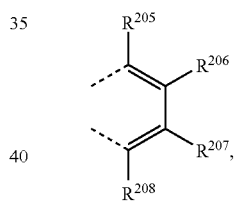

wherein $R^{205}$, $R^{206}$, $R^{207}$ and $R^{208}$ are independently of each other H, or $C_1$-$C_8$alkyl,
the ring A represents an optionally substituted aryl or heteroaryl group; or the ring A may be taken with the pyridyl group binding to the ring A to form a ring; the alkyl group, alkenyl group, alkynyl group, aryl group, heteroaryl group, alkoxy group, alkylthio group, acyl group, and alkyloxycarbonyl group represented by $R^6$, $R^7$, $R^8$, and $R^9$ may be substituted.

Another example of a preferred class of ligands L are compounds of the formula

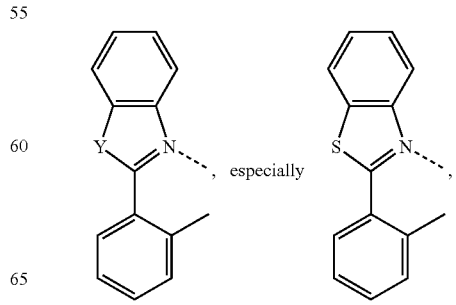, especially wherein Y is S, O, $NR^{200}$, wherein $R^{200}$ is hydrogen, $C_1$-$C_4$alkyl, $C_2$-$C_4$alkenyl, optionally substituted $C_6$-$C_{10}$aryl (especially phenyl), —$(CH_2)_r$—Ar (wherein Ar is an optionally substituted $C_6$-$C_{10}$aryl, especially

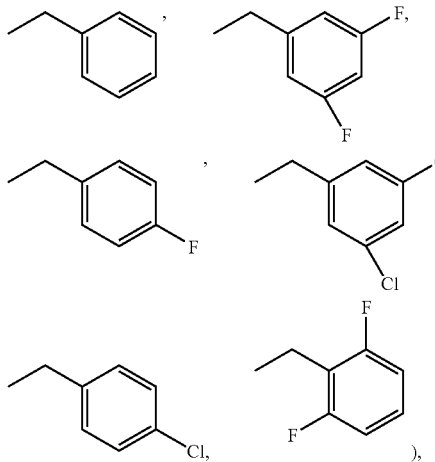

a group —$(CH_2)_r X^{20}$, wherein r' is an integer of 1 to 5, $X^{20}$ is halogen (especially F, or Cl), hydroxy, cyano, —O—$C_1$-$C_4$alkyl, di($C_1$-$C_4$alkyl)amino, amino, or cyano; a group —$(CH_2)_r OC(O)(CH_2)r''CH_3$, where r is 1, or 2, and r'' is 0, or 1;

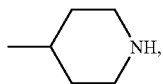

—NH-Ph, —$C(O)CH_3$, —$CH_2$—O—$(CH_2)_2$—$Si(CH_3)_3$, or

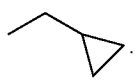

Another preferred class of ligands L is described in WO06/000544, of which the following can advantageously be used according to the present invention:

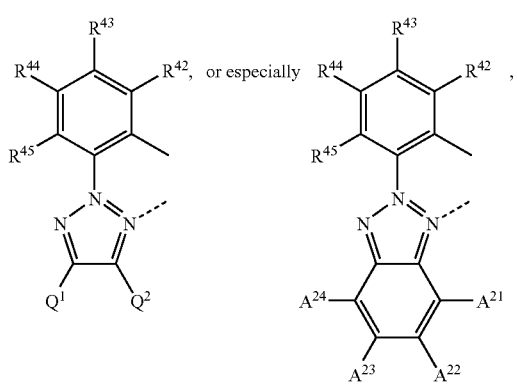

wherein
$Q^1$ and $Q^2$ are independently of each other hydrogen, $C_1$-$C_{24}$alkyl, or $C_6$-$C_{18}$aryl, $A^{21}$ is hydrogen, halogen, $C_1$-$C_4$alkoxy, or $C_1$-$C_4$alkyl,
$A^{22}$ is hydrogen, halogen, $C_1$-$C_{12}$alkoxy, $C_1$-$C_{12}$alkyl, or $C_6$-$C_{10}$aryl,
$A^{23}$ is hydrogen, halogen, $C_1$-$C_{12}$alkoxy, $C_1$-$C_{12}$alkyl, or $C_6$-$C_{10}$aryl,
$A^{24}$ is hydrogen, halogen, $C_1$-$C_4$alkoxy, or $C_1$-$C_4$alkyl, or
$A^{22}$ and $A^{23}$, or $A^{23}$ and $A^{24}$ together form a group

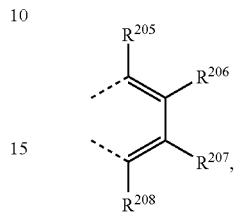

wherein $R^{205}$, $R^{206}$, $R^{207}$ and $R^{208}$ are independently of each other H, halogen, $C_1$-$C_{12}$alkoxy, or $C_1$-$C_{12}$alkyl,
$R^{42}$ is H, halogen, $C_1$-$C_{12}$alkyl, $C_1$-$C_{12}$alkoxy, or $C_1$-$C_4$ perfluoroalkyl,
$R^{43}$ is H, halogen, $C_1$-$C_{12}$alkyl, $C_1$-$C_{12}$alkoxy, $C_1$-$C_4$ perfluoroalkyl, $C_7$-$C_{15}$aralkyl, or $C_6$-$C_{10}$aryl,
$R^{44}$ is H, halogen, $C_1$-$C_{12}$alkyl, $C_1$-$C_{12}$alkoxy, $C_6$-$C_{10}$aryl, $C_7$-$C_{15}$aralkyl, or $C_1$-$C_4$ perfluoroalkyl,
$R^{45}$ is H, halogen, $C_1$-$C_{12}$alkyl, $C_1$-$C_{12}$alkoxy, or $C_1$-$C_4$ perfluoroalkyl,
more especially wherein
$A^{21}$ is hydrogen,
$A^{22}$ is hydrogen, $C_1$-$C_{12}$alkoxy, $C_1$-$C_{12}$alkyl, or phenyl,
$A^{23}$ is hydrogen, $C_1$-$C_{12}$alkoxy, $C_1$-$C_{12}$alkyl, or phenyl,
$A^{24}$ is hydrogen, or
$A^{23}$ and $A^{24}$, or $A^{23}$ and $A^{24}$ together form a group

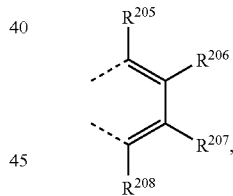

wherein $R^{205}$, $R^{206}$, $R^{207}$ and $R^{208}$ are independently of each other H, or $C_1$-$C_8$alkyl,
$R^{42}$ is H, F, $C_1$-$C_{12}$alkyl, $C_1$-$C_8$alkoxy, or $C_1$-$C_4$ perfluoroalkyl,
$R^{43}$ is H, F, $C_1$-$C_{12}$alkyl, $C_1$-$C_8$alkoxy, $C_1$-$C_4$ perfluoroalkyl, or phenyl,
$R^{44}$ is H, F, $C_1$-$C_{12}$alkyl, $C_1$-$C_8$alkoxy, or $C_1$-$C_4$ perfluoroalkyl, and
$R^{45}$ is H, F, $C_1$-$C_{12}$alkyl, $C_1$-$C_8$alkoxy, or $C_1$-$C_4$ perfluoroalkyl.

Further examples for this class of ligands are described in WO06/000544 from page 14, line 12, to page 18, line 3, and in the examples on pages 21-56 and 67-72 of said document, which passages are hereby incorporated by reference.

Another preferred class of ligands L is described in patent application No. PCT/EP2006/069803, of which the following can advantageously be used according to the present invention:

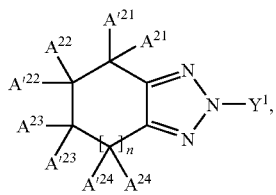

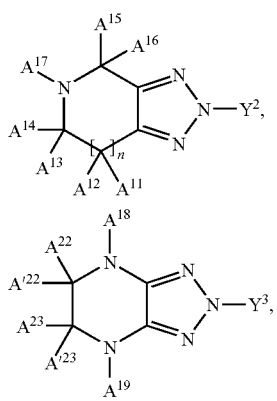

wherein n is 0, 1 or 2, especially 1;

$A^{12}, A^{14}, A^{16}, A^{21}, A^{22}, A^{23}$ and $A^{24}$ are independently of each other hydrogen, CN, halogen, $C_1$-$C_{24}$alkyl, $C_1$-$C_{24}$alkoxy, $C_1$-$C_{24}$alkylthio, $C_1$-$C_{24}$ perfluoroalkyl, $C_6$-$C_{18}$aryl, which is optionally substituted by G; —$NR^{25}R^{26}$, —$CONR^{25}R^{26}$, or —$COOR^{27}$, or $C_2$-$C_{10}$heteroaryl, which is optionally substituted by G; or $C_5$-$C_{12}$cycloalkyl, $C_5$-$C_{12}$cycloalkoxy, $C_5$-$C_{12}$cycloalkylthio, each of which is optionally substituted by G; especially a group of formula

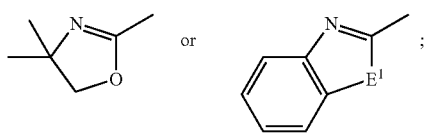

or 2 adjacent radicals $A^{12}$, $A^{14}$; or $A^{14}$, $A^{17}$; or $A^{17}$, $A^{16}$; or $A^{21}$, $A^{22}$; or $A^{22}$, $A^{23}$; or $A^{23}$, $A^{24}$; or $A^{18}$, $A^{22}$; or $A^{23}$, $A^{19}$, bonding to vicinal atoms, together are a group of formula

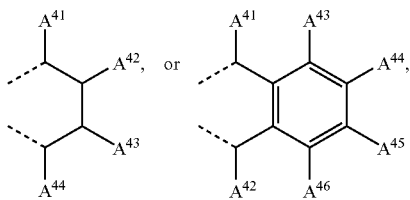

wherein $A^{41}$, $A^{42}$, $A^{43}$, $A^{44}$, $A^{45}$, $A^{46}$ and $A^{47}$ are independently of each other H, halogen, CN, $C_1$-$C_{24}$alkyl, $C_1$-$C_{24}$ perfluoroalkyl, $C_1$-$C_{24}$alkoxy, $C_1$-$C_{24}$alkylthio, $C_6$-$C_{18}$aryl, which may optionally be substituted by G, —$NR^{25}R^{26}$, —$CONR^{25}R^{26}$, or —$COOR^{27}$, or $C_2$-$C_{10}$heteroaryl; especially

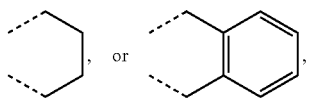

while each $A^{11}, A^{13}, A^{15}, A^{'21}, A^{'22}, A^{'23}$ and $A^{'24}$ independently is hydrogen or $C_1$-$C_{24}$alkyl;

or 2 adjacent radicals $A^{11}, A^{12}$; $A^{13}, A^{14}$; $A^{15}, A^{16}$; $A^{'21}, A^{21}$; $A^{'22}, A^{22}$; $A^{'23}, A^{23}$; $A^{'24}, A^{24}$, bonding to the same carbon atom, together are =O or =$NR^{25}$ or =N—$OR^{25}$ or =N—OH;

$E^1$ is O, S, or $NR^{25}$, $R^{25}$ and $R^{26}$ are independently of each other $C_6$-$C_{18}$aryl, $C_7$-$C_{18}$aralkyl, or $C_1$-$C_{24}$alkyl, $R^{27}$ is $C_1$-$C_{24}$alkyl, $C_6$-$C_{18}$aryl, or $C_7$-$C_{18}$aralkyl; and $Y^1, Y^2$ and $Y^3$ are independently of each other a group of formula

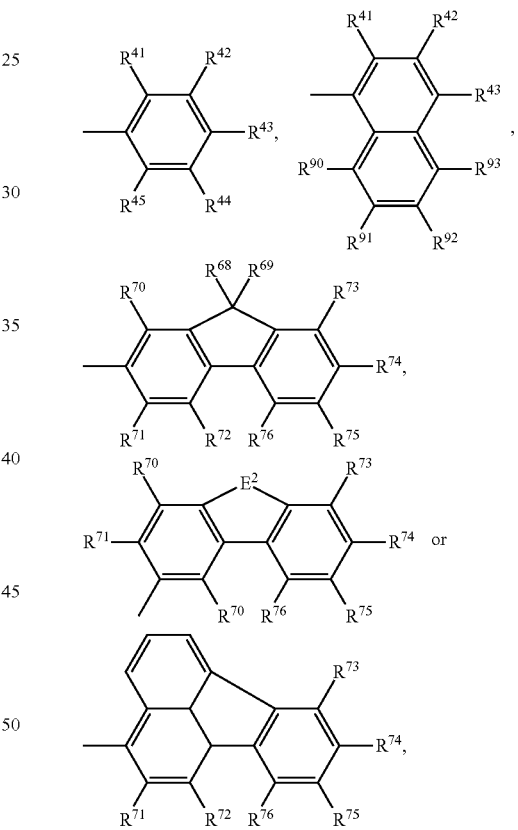

wherein $R^{41}$ is the bond to $M^2$, $R^{71}$ is the bond to $M^2$, $R^{42}$ is hydrogen, or $C_1$-$C_{24}$alkyl, CN, $C_1$-$C_{24}$alkyl, which is substituted by F, halogen, especially F, $C_6$-$C_{18}$-aryl, $C_6$-$C_{18}$-aryl which is substituted by $C_1$-$C_{12}$alkyl, or $C_1$-$C_8$alkoxy, $R^{43}$ is hydrogen, CN, halogen, especially F, $C_1$-$C_{24}$alkyl, which is substituted by F, $C_6$-$C_{18}$aryl, $C_6$-$C_{18}$aryl which is substituted by $C_1$-$C_{12}$alkyl, or $C_1$-$C_8$alkoxy, —$CONR^{25}R^{26}$, —$COOR^{27}$,

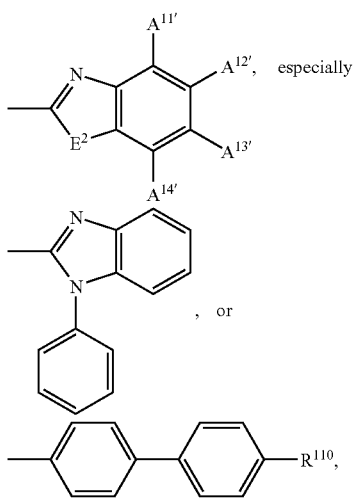, especially

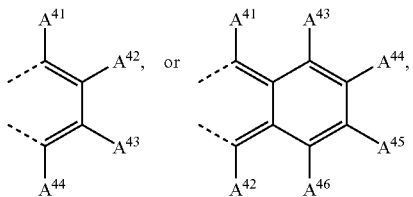

wherein
E² is —S—, —O—, or —NR²⁵'—, wherein R²⁵' is $C_1$-$C_{24}$alkyl, or $C_6$-$C_{10}$aryl,
$R^{110}$ is H, CN, $C_1$-$C_{24}$alkyl, $C_1$-$C_{24}$alkoxy, $C_1$-$C_{24}$alkylthio, —NR²⁵R²⁶, —CONR²⁵R²⁶, or —COOR²⁷, or
$R^{42}$ and $R^{43}$ are a group of formula

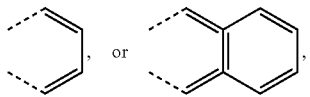

wherein $A^{41}$, $A^{42}$, $A^{43}$, $A^{44}$, $A^{45}$, $A^{46}$ and $A^{47}$ are independently of each other H, halogen, CN, $C_1$-$C_{24}$alkyl, $C_1$-$C_{24}$perfluoroalkyl, $C_1$-$C_{24}$alkoxy, $C_1$-$C_{24}$alkylthio, $C_6$-$C_{18}$aryl, which may optionally be substituted by G, —NR²⁵R²⁶, —CONR²⁵R²⁶ or —COOR²⁷, or $C_2$-$C_{10}$heteroaryl; especially

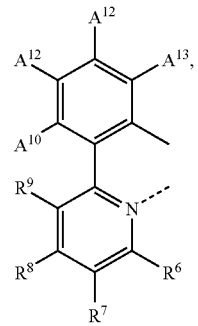

$R^{44}$ is hydrogen, CN or $C_1$-$C_{24}$alkyl, $C_1$-$C_{24}$alkyl, which is substituted by F, halogen, especially F, $C_6$-$C_{18}$-aryl, $C_6$-$C_{18}$-aryl which is substituted by $C_1$-$C_{12}$ alkyl, or $C_1$-$C_8$alkoxy,
$R^{45}$ is hydrogen, CN or $C_1$-$C_{24}$alkyl, $C_1$-$C_{24}$alkyl, which is substituted by F, halogen, especially F, $C_6$-$C_{18}$-aryl, $C_6$-$C_{18}$-aryl which is substituted by $C_1$-$C_{12}$ alkyl, or $C_1$-$C_8$alkoxy,
$A^{11'}$, $A^{12'}$, $A^{13'}$, and $A^{14'}$ are independently of each other H, halogen, CN, $C_1$-$C_{24}$alkyl, $C_1$-$C_{24}$alkoxy, $C_1$-$C_{24}$alkylthio, —NR²⁵R²⁶, —CONR²⁵R²⁶, or —COOR²⁷,
$R^{68}$ and $R^{69}$ are independently of each other $C_1$-$C_{24}$alkyl, especially $C_4$-$C_{12}$alkyl, especially hexyl, heptyl, 2-ethylhexyl, and octyl, which can be interrupted by one or two oxygen atoms, $R^{70}$, $R^{72}$, $R^{73}$, $R^{74}$, $R^{75}$, $R^{76}$, $R^{90}$, $R^{91}$, $R^{92}$, and $R^{93}$ are independently of each other H, halogen, especially F, CN, $C_1$-$C_{24}$alkyl, $C_6$-$C_{10}$aryl, $C_1$-$C_{24}$alkoxy, $C_1$-$C_{24}$alkylthio, —NR²⁵R²⁶, —CONR²⁵R²⁶, or —COOR²⁷, wherein R²⁵, R²⁶ and R²⁷ are as defined above and G is $C_1$-$C_{18}$alkyl, —OR³⁰⁵, SR³⁰⁵, NR³⁰⁵R³⁰⁶, —CONR³⁰⁵R³⁰⁶, or —CN, wherein R³⁰⁵ and R³⁰⁶ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—; or R³⁰⁵ and R³⁰⁶ together form a five or six membered ring such as

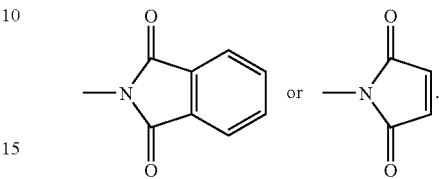

Another preferred class of ligands L is a compound of formula

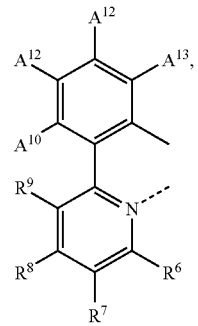

wherein $R^6$ is hydrogen, halogen, especially F, or Cl; nitro, $C_1$-$C_4$alkyl, $C_1$-$C_4$ perfluoroalkyl, $C_1$-$C_4$alkoxy, or optionally substituted $C_6$-$C_{10}$aryl, especially phenyl, $R^7$ is hydrogen, halogen, especially F, or Cl; $C_1$-$C_4$alkyl, $C_1$-$C_4$ perfluoroalkyl, optionally substituted $C_6$-$C_{10}$aryl, especially phenyl, or optionally substituted $C_6$-$C_{10}$ perfluoroaryl, especially $C_6F_5$,
$R^8$ is hydrogen, $C_1$-$C_4$alkyl, $C_1$-$C_8$alkoxy, $C_1$-$C_4$ perfluoroalkyl, optionally substituted $C_6$-$C_{10}$aryl, especially phenyl, or optionally substituted $C_6$-$C_{10}$ perfluoroaryl, especially $C_6F_5$,
$R^9$ is hydrogen, halogen, especially F, or Cl; nitro, cyano, $C_1$-$C_4$alkyl, $C_1$-$C_4$ perfluoroalkyl, $C_1$-$C_4$alkoxy, or optionally substituted $C_6$-$C_{10}$aryl, especially phenyl,
$A^{10}$ is hydrogen, halogen, especially F, or Cl; nitro, cyano, $C_1$-$C_4$alkyl, $C_2$-$C_4$alkenyl, $C_1$-$C_4$ perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$ perfluoroaryl, especially $C_6F_5$,
$A^{11}$ is hydrogen, halogen, especially F, or Cl; nitro, cyano, $C_1$-$C_4$alkyl, $C_2$-$C_4$alkenyl, $C_1$-$C_4$ perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$ perfluoroaryl, especially $C_6F_5$,
$A^{12}$ is hydrogen, halogen, especially F, or Cl; nitro, hydroxy, mercapto, amino, $C_1$-$C_4$alkyl, $C_2$-$C_4$alkenyl, $C_1$-$C_4$ perfluoroalkyl, $C_1$-$C_4$alkoxy, —O—$C_1$-$C_4$ perfluoroalkyl, —S—$C_1$-$C_4$alkyl, a group —(CH₂)ᵣX²⁰, wherein r is 1, or 2, X²⁰ is halogen, especially F, or Cl; hydroxy, cyano, —O—$C_1$-$C_4$alkyl, di($C_1$-$C_4$alkyl)amino, —CO₂X²¹, wherein X²¹ is H, or $C_1$-$C_4$alkyl; —CH=CHCO₂X²², wherein X²² is $C_1$-$C_4$alkyl; —CH(O), —SO₂X²³, —SOX²³, —N C(O)X²³, —NSO₂X²³, —NHX²³, —N(X²³)₂, wherein X²³ is C₁-C₄alkyl; tri(C₁-C₄alkyl)siloxanyl, optionally substituted —O—C₆-C₁₀aryl, especially phenoxy, cyclohexyl, optionally substituted C₆-C₁₀aryl, especially phenyl, or optionally substituted C₆-C₁₀ perfluoroaryl, especially C₆F₅, and A¹³ is hydrogen, nitro, cyano, C₁-C₄alkyl, C₂-C₄alkenyl, C₁-C₄ perfluoroalkyl, —O—C₁-C₄ perfluoroalkyl, tri(C₁-C₄alkyl)silanyl, or optionally substituted C₆-C₁₀aryl.

Specific examples of L are the following compounds (VI-1) to (VI-53):

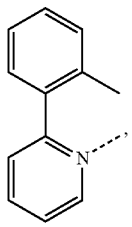
(VI-1)

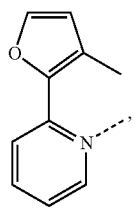
(VI-2)

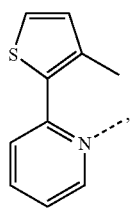
(VI-3)

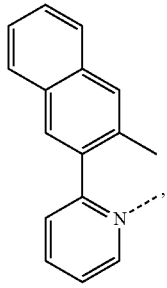
(VI-4)

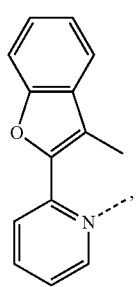
(VI-5)

-continued

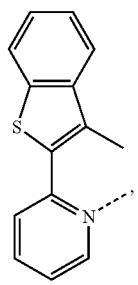
(VI-6)

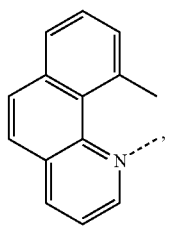
(VI-7)

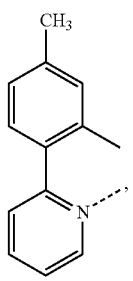
(VI-8)

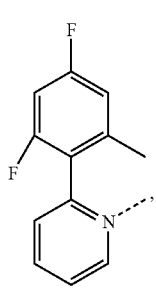
(VI-9)

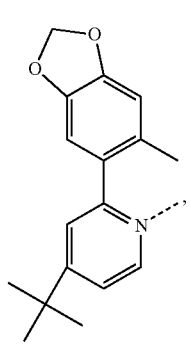
(VI-10)

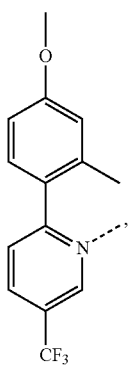 (VI-11)
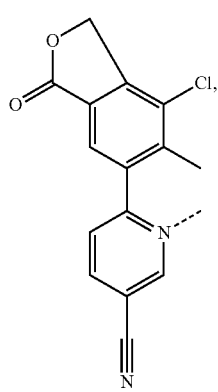 (VI-15)
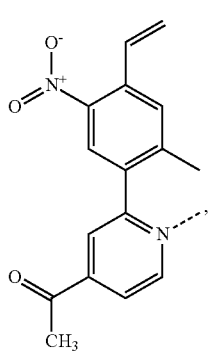 (VI-12)
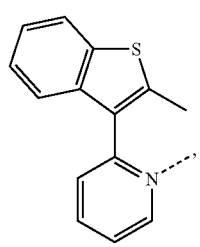 (VI-16)
(VI-17)
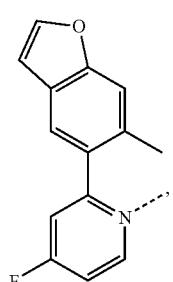
(VI-13)
(VI-18)
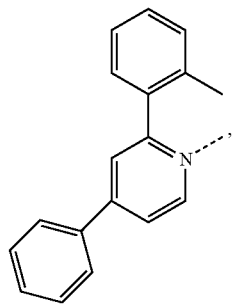
(VI-14)
(VI-19)

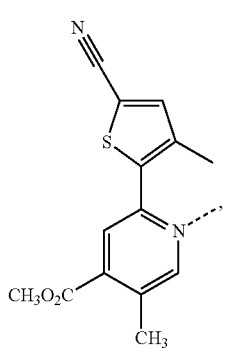 (VI-20)
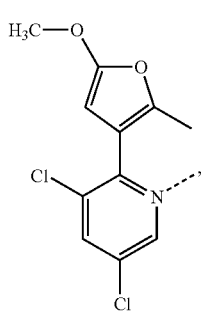 (VI-21)
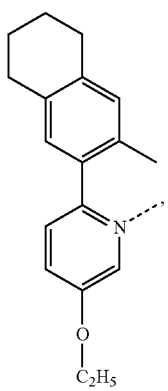 (VI-22)
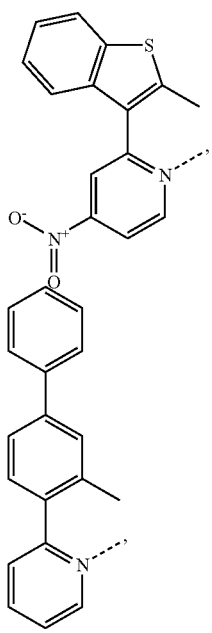 (VI-23)
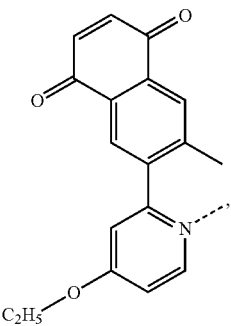 (VI-25)
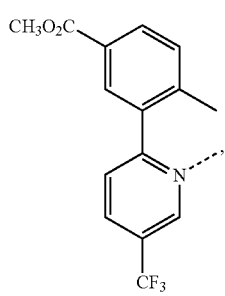 (VI-26)
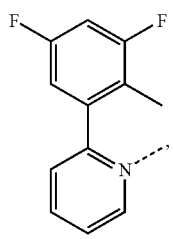 (VI-27)
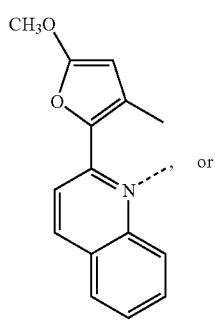 (VI-28)
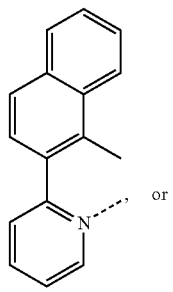 (VI-29)

-continued
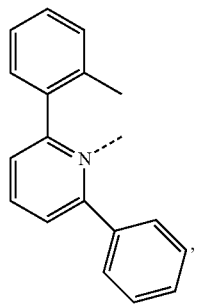 (VI-30)
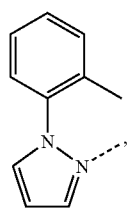 (VI-31)
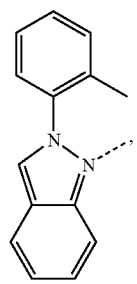 (VI-32)
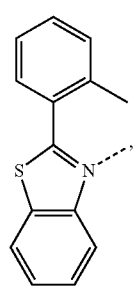 (VI-33)
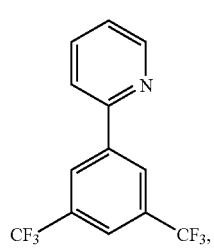 (VI-34)
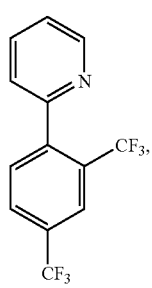 (VI-35)
-continued
(VI-36)
(VI-37)
(VI-37)
(VI-38)

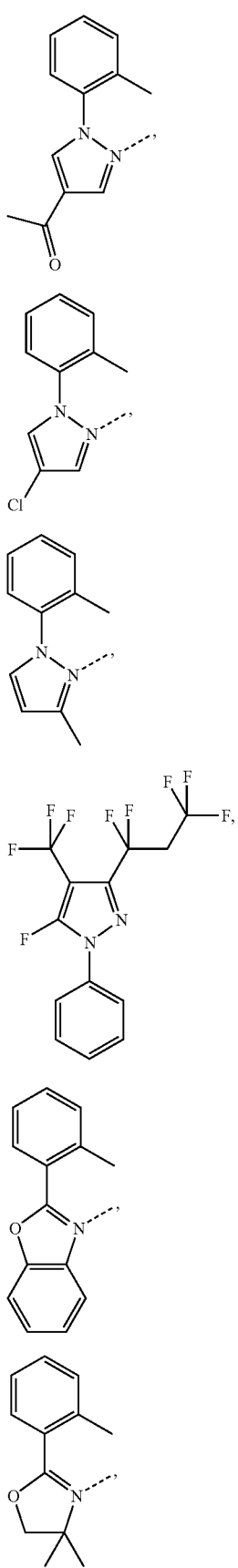
(VI-39)
(VI-40)
(VI-41)
(VI-42)
(VI-43)
(VI-44)
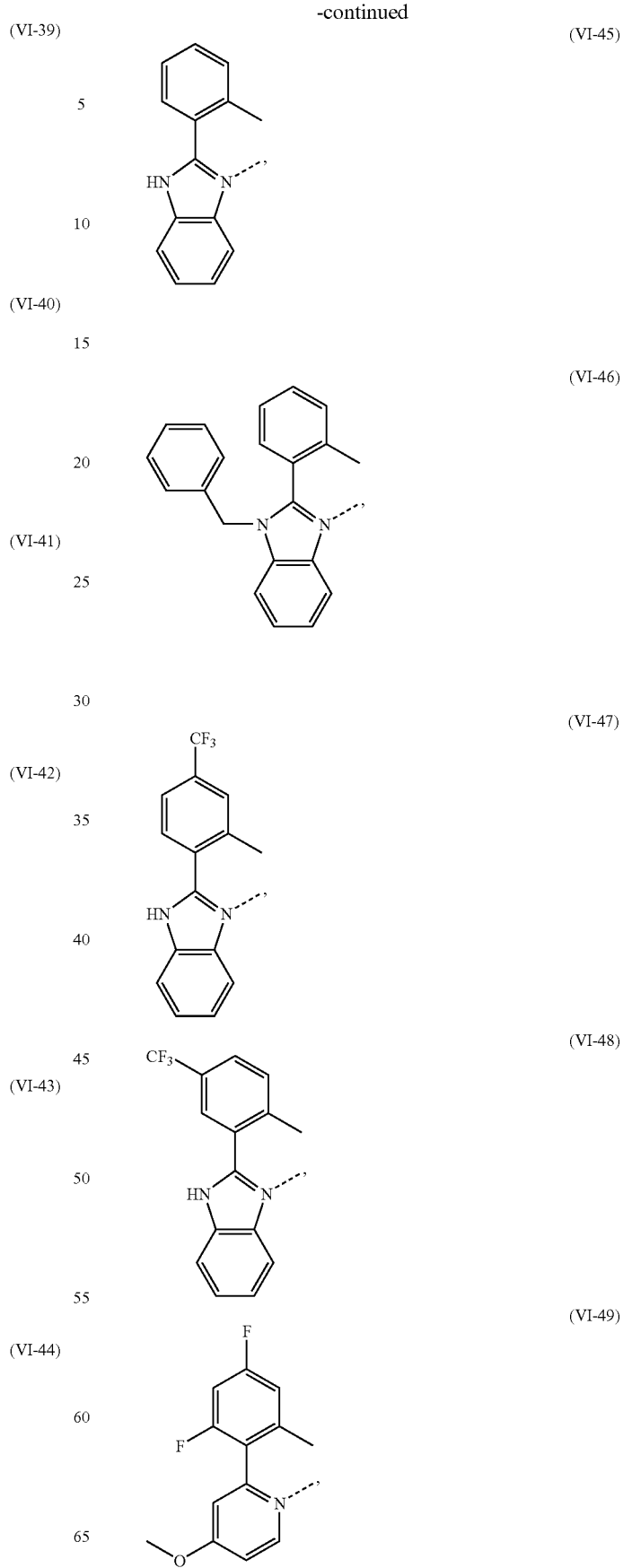
(VI-45)
(VI-46)
(VI-47)
(VI-48)
(VI-49)

-continued

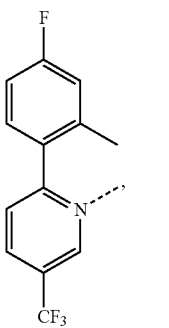
(VI-50)

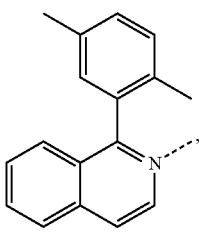
(VI-51)

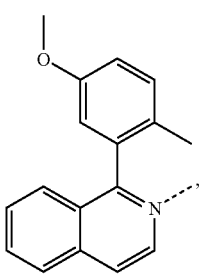
(VI-52)

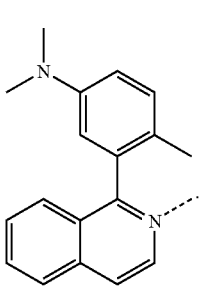
(VI-53)

Special emphasis among them is given to (VI-1) to (VI-47) as well as to those of the below examples.

Preferred complexes are of formula (I) or (I') wherein L independently is a bidentate ligand

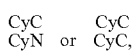

wherein the 2 moieties CyC and CyN, or CyC and CyC, are interlinked by a chemical bond,
and
LDH is a bidentate ligand of the formula II and LTH is a dimer of LDH, binding to 2 metal atoms M, of the formula II', wherein
W is selected from O, S, $NR_4$, $CR_5R_6$,
X is N or $CR_7$,
Y is selected from O, S, $NR_8$;
$R_1$, $R_2$ independently are selected from H, unsubstituted or substituted $C_1$-$C_{18}$alkyl, unsubstituted or substituted $C_2$-$C_{18}$alkenyl, unsubstituted or substituted $C_5$-$C_{10}$aryl, unsubstituted or substituted $C_2$-$C_{10}$heteroaryl, $C_1$-$C_{18}$acyl, halogen, $C_1$-$C_{18}$alkoxy, $C_1$-$C_{18}$alkylthio, $C_1$-$C_{18}$acyl, $C_5$-$C_{10}$aryl, $C_3$-$C_{12}$cycloalkyl, $C_1$-$C_{18}$acyloxy, $C_5$-$C_{10}$aryloxy, $C_3$-$C_{12}$cycloalkyloxy, or from the residues COR, CH=NR, CH=N—OH, CH=N—OR, COOR, CONHR, CONRR', CONH—NHR, CONH—NRR', $SO_2R$, $SO_3R$, $SO_2NHR$, $SO_2NRR'$, $SO_2NH$—NHR, $SO_2NH$—NRR', S(O)R, S(O)OR, S(O)NHR, S(O)NRR', S(O)NH—NHR, S(O)NH—NRR', SiRR'R'', PORR', PO(OR)R', $PO(OR)_2$, $PO(NHR)_2$, $PO(NRR')_2$, CN, $NO_2$, NHR, NRR', NH—NHR, NH—NRR', CONROH;
where R, R' and R'' independently are selected from $C_1$-$C_{12}$alkyl, $C_1$-$C_6$haloalkyl, phenyl, cyclopentyl, cyclohexyl; and R may also be hydrogen;
or the neighbouring residues $R_1$ and $R_2$ form an organic bridging group completing, together with the carbon atoms they are bonding to, a carbocyclic or heterocyclic, non-aromatic or preferably aromatic, 6-membered ring, which optionally may be substituted;
$R_4$, $R_5$, $R_6$ independently are H, unsubstituted or substituted $C_1$-$C_8$alkyl, unsubstituted or substituted $C_2$-$C_8$alkenyl, unsubstituted or substituted phenyl;
$R_7$, if present, together with its neighbouring residue $R_3$ forms an organic bridging group completing, with the carbon atoms they are bonding to, an aromatic 6-membered ring, which optionally may be substituted; and in case that W is O, $NR_4$, $CR_5R_6$ and/or Y contains a nitrogen atom, $R_7$ also embraces the meanings given for $R_4$;
or $R_3$ is H, unsubstituted or substituted $C_1$-$C_{18}$alkyl, unsubstituted or substituted $C_2$-$C_{18}$alkenyl, unsubstituted or substituted phenyl, unsubstituted or substituted $C_2$-$C_{10}$heteroaryl, $C_1$-$C_{18}$acyl; and
$R'_3$ is unsubstituted or substituted $C_1$-$C_8$alkylene, unsubstituted or substituted $C_2$-$C_8$alkenylene, unsubstituted or substituted phenylene, unsubstituted or substituted $C_2$-$C_{10}$heteroarylene, $C_2$-$C_8$diacylene;
$R_8$ is selected from hydrogen, $C_1$-$C_{18}$alkyl, $C_2$-$C_{18}$alkenyl, $C_5$-$C_{10}$aryl, $C_4$-$C_{10}$heteroaryl, and electron pulling substituents such as $SO_2R'$, $SO_3R'$, $SO_2NHR'$, $SO_2NRR'$, $SO_2NH$—NHR', $SO_2NH$—NRR', $C_1$-$C_{18}$acyl, $C_1$-$C_8$haloalkyl;
such as those of the formula (I) or (I') wherein
Y is O or $NR_8$;
M is selected from Tl, Pb, Bi, In, Sn, Sb, Te, Mo, Cr, Mn, Ta, V, Cu, Fe, Ru, Ni, Co, Ir, Pt, Pd, Rh, Re, Os, Ag and Au;
$R_1$, $R_2$, $R_3$, $R_4$, $R_5$, $R_6$, $R_7$, $R_8$ are as defined above and, if substituted, the substituent is selected from halogen, $C_1$-$C_{12}$alkoxy, $C_1$-$C_{12}$alkylthio, benzoyl substituted by $C_1$-$C_4$alkyl or $C_1$-$C_4$alkoxy or halogen, benzoyloxy substituted by $C_1$-$C_4$alkyl or $C_1$-$C_4$alkoxy or halogen, phenyl, phenyloxy, $C_3$-$C_{12}$cycloalkyl, $C_3$-$C_{12}$cycloalkyloxy, or from the residues COR, OCOR, COOR, CONHR, CONRR', $SO_2R$, $SO_3R$, $SO_2NHR$, $SO_2NRR'$, SiRR'R'', PORR', PO(OR)R', $PO(OR)_2$, CN, $NO_2$, NHR, NRR', NH—NHR, NH—NRR', where R, R' and R'' independently are selected from $C_1$-$C_{12}$alkyl, $C_1$-$C_6$haloalkyl, phenyl, cyclopentyl, cyclohexyl; and R may also be hydrogen.

More preferred complexes are of the formula I, wherein
n is an integer 1,
M is Co, Fe, or especially Ir, Rh, and m is 2, or
M is Ni, Rh, Ru, or especially Pd, Pt, and m is 1,
$R_1$, $R_2$ independently are selected from H, unsubstituted or substituted $C_1$-$C_8$alkyl, unsubstituted or substituted phenyl, halogen, $C_1$-$C_8$alkoxy, COR, COOR, $SO_2R$, CN, NHR, NRR';

or the neighbouring residues $R_1$ and $R_2$ form an organic bridging group completing, together with the carbon atoms they are bonding to, an annellated phenyl ring, which optionally may be substituted;

$R_5$, $R_6$ independently are H, unsubstituted or substituted $C_1$-$C_8$alkyl, unsubstituted or substituted $C_2$-$C_8$alkenyl, unsubstituted or substituted phenyl;

$R_4$ is as defined for $R_5$ or is H;

$R_7$, if present, together with its neighbouring residue $R_3$ forms an organic bridging group completing, with the carbon atoms they are bonding to, a phenyl ring, which optionally may be substituted; and in case that W is O, $NR_4$, $CR_5R_6$ and/or Y contains a nitrogen atom, $R_7$ also embraces hydrogen, $C_1$-$C_4$alkyl;

or $R_3$ is unsubstituted or substituted $C_1$-$C_8$alkyl, unsubstituted or substituted $C_2$-$C_8$alkenyl, unsubstituted or substituted phenyl; and any substituent, if present, is selected from halogen, $C_1$-$C_8$alkyl, $C_1$-$C_8$alkoxy, phenyl, phenyloxy, COR, OCOR, COOR, $SO_2R$, CN, NHR, NRR'; and R, R' and R" independently are selected from $C_1$-$C_6$alkyl, and R may also be hydrogen;

$R_8$ is H, $SO_2$—$R_{11}$, CO—$R_{11}$, where $R_{11}$ is $C_1$-$C_{12}$alkyl, $C_1$-$C_{12}$haloalkyl, phenyl, phenyl substituted by halogen.

Of special technical interest are those compounds wherein Y is O. Likewise of technical interest are those compounds wherein $R_3$ is different from hydrogen.

Examples for some more preferred complexes of the invention are those of the formulae

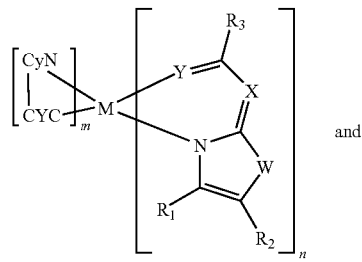

(III)

and

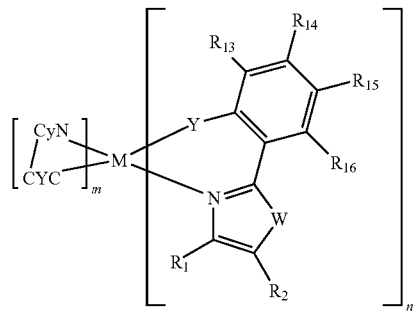

(IV)

and tautomeric forms thereof
wherein

is a bidentate C,N-binding ligand as defined above,
n is 1,
M is Ir and m is 2 or
M is Pt and m is 1;
W is O, S, $NR_4$, $CR_5R_6$,
X is N or CH,
Y is O or $NR_8$;
$R_1$, $R_2$ independently are selected from H, $C_1$-$C_8$alkyl, phenyl, halogen, $C_1$-$C_8$alkoxy, CN, NHR, NRR';
or $R_1$ and $R_2$ together with the carbon atoms they are bonding to form an annellated phenyl ring, which optionally may be substituted;
$R_3$ is H, unsubstituted or substituted $C_1$-$C_8$alkyl, unsubstituted or substituted $C_2$-$C_8$alkenyl, unsubstituted or substituted phenyl;
$R_4$, $R_5$, $R_6$ independently are H or $C_1$-$C_8$alkyl;
$R_8$ is H, $C_1$-$C_8$alkyl, COR, $SO_2R$;
$R_{13}$, $R_{14}$, $R_{15}$, $R_{16}$ independently are hydrogen or a substituent; and
any substituent, if present, is selected from halogen, $C_1$-$C_8$alkyl, $C_1$-$C_8$alkoxy, COR, NHR, NRR'; and
R, R' and R" independently are selected from $C_1$-$C_6$alkyl, and R may also be hydrogen.

Examples for dimeric complexes of the formula I' include those of the formula

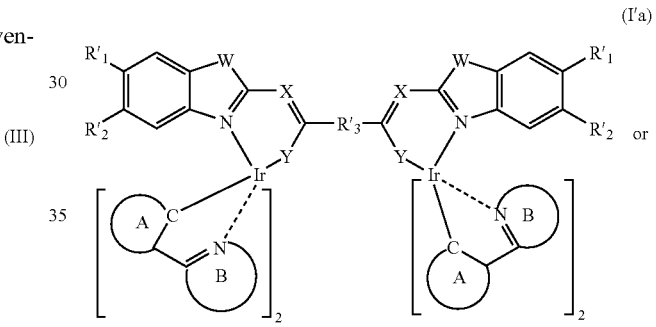

(I'a)

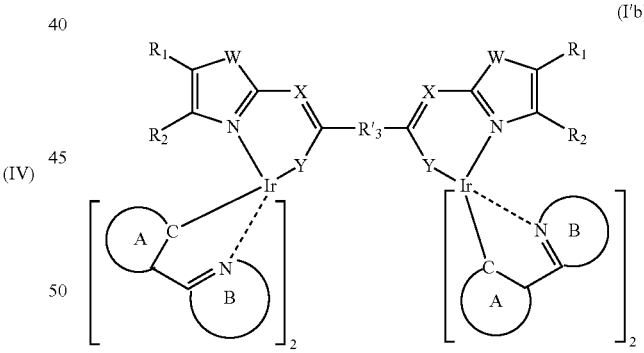

(I'b)

wherein
W, X, Y and the ligands

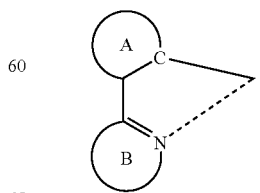

are as defined above, $R_1$, $R_2$ independently are selected from H, unsubstituted or substituted $C_1$-$C_8$alkyl, unsubstituted or substituted phenyl, halogen, $C_1$-$C_8$alkoxy, COR, COOR, $SO_2R$, CN, NHR, NRR';

$R'_1$ and $R'_2$, independently, are hydrogen or a substituent, where any substituent, if present, is selected from halogen, $C_1$-$C_8$alkoxy, phenyl, phenyloxy, COR, OCOR, COOR, $SO_2R$, CN, NHR, NRR'; and R, R' and R" independently are selected from $C_1$-$C_6$alkyl, and R may also be hydrogen; and $R'_3$ is unsubstituted or substituted $C_1$-$C_8$alkylene, unsubstituted or substituted $C_2$-$C_8$alkenylene, unsubstituted or substituted phenylene;

such as the compound

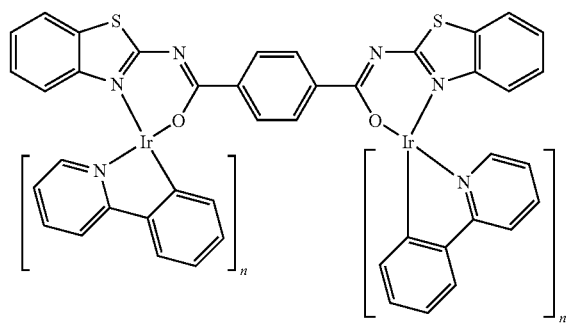

with n=2.

Conversion of the present metal complexes into suitable layers may follow methods known in the art; construction of the electroluminescent devices containing said layers is well known in the art (see, for example, WO04/017043, and further documents mentioned above).

Some of the ligands of formula II are known compounds; some of the more interesting ligands however are novel. The present invention therefore includes compounds of the formula V or VI

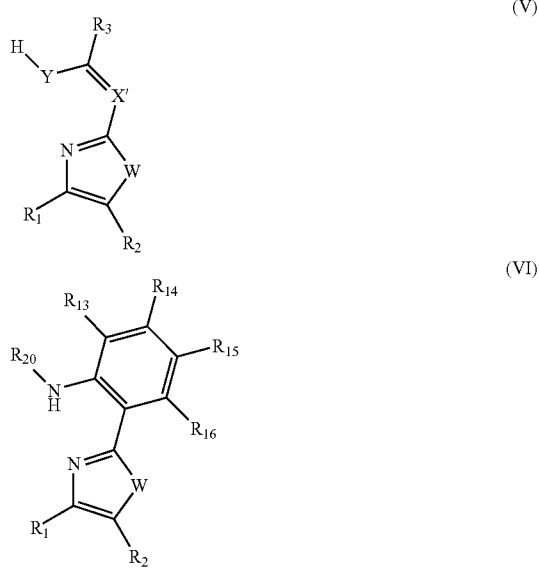

or tautomers thereof, wherein $R_1$, $R_2$, $R_3$, W and Y are as defined for the metal complexes of the invention;

X' is N, and in case that W is O, $NR_4$, $CR_5R_6$ and/or Y contains a nitrogen atom, X' may also stand for $CR_{17}$;

R is $C_1$-$C_{12}$alkyl, phenyl, or said phenyl or $C_1$-$C_{12}$alkyl substituted by $C_1$-$C_4$alkoxy or halogen;

at least one of $R_{13}$, $R_{14}$, $R_{15}$, $R_{16}$ is an electron-pushing substituent, preferably selected from halogen, hydroxy, OR, $C_1$-$C_{18}$alkyl, $C_1$-$C_{18}$alkoxy, $C_1$-$C_{18}$alkylthio, $C_1$-$C_{18}$acyloxy, NH—$C_1$-$C_{18}$acyl, NR"R', NH—NR"R', CONR'OH; especially where one of $R_{13}$, $R_{14}$, $R_{15}$, $R_{16}$ is an electron-pushing substituent selected from hydroxy, OR, $C_1$-$C_{18}$alkyl, $C_1$-$C_{18}$alkoxy, $C_1$-$C_{18}$alkylthio, NR"R';

while the remaining of $R_{13}$, $R_{14}$, $R_{15}$, $R_{16}$, independently, may also be selected from hydrogen or substituents as defined further above, for example halogen, $C_1$-$C_{18}$alkyl, $C_1$-$C_{18}$acyl, $C_5$-$C_{10}$aryl, $C_3$-$C_{12}$cycloalkyl, $C_5$-$C_{10}$aryloxy, $C_3$-$C_{12}$cycloalkyloxy, or from the residues COR', CH=NR', CH=N—OH, CH=N—OR', COOR', CONHR', CONRR', CONH—NHR', CONH—NRR', $SO_2R'$, $SO_3R'$, $SO_2NHR'$, $SO_2NRR'$, $SO_2NH$—NHR', $SO_2NH$—NRR', S(O)R, S(O)OR', S(O)NHR', S(O)NRR', S(O)NH—NHR', S(O)NH—NRR', SiRR'R", POR"R', PO(OR")R', $PO(OR')_2$, $PO(NHR')_2$, $PO(NRR')_2$, CN, $NO_2$, NHR', NRR', NH—NHR', NH—NRR', CONR'OH, and especially are hydrogen or alkyl;

R' and R" independently are as defined for R, or are hydrogen;

$R_{17}$ is H, $C_1$-$C_6$alkyl, and $R_{20}$ is an electron pulling residue selected from $SO_2R'$, $SO_3R'$, $SO_2NHR'$, $SO_2NRR'$, $SO_2NH$—NHR', $SO_2NH$—NRR', $C_1$-$C_{18}$acyl, $C_1$-$C_8$haloalkyl, especially $SO_2R$ or $C_1$-$C_4$ perhaloalkyl such as $C_1$-$C_4$ perfluoroalkyl.

The preparation of the novel ligands may follow methods known in the art. For example, those ligands wherein X is $CR_7$, may be obtained in analogy to methods described in WO05/106868.

Ligands wherein X stands for nitrogen are conveniently prepared starting from the corresponding amines

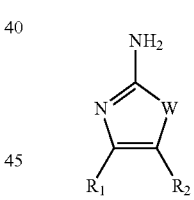

by reaction with an acyl component such as a suitable acid anhydride or acid halogenide $R_3$—CO-Hal to obtain a ligand wherein Y is O; or by reaction with a suitable nitrile to obtain a ligand wherein Y is NH.

Ligands wherein Y is O may be converted into ligands containing Y as S in analogy to the procedure described by K. Waisser, Sci. Pharm. 67, 1999, 113-122.

Reactions may be carried out in analogy to known methods (see, for example, Dothager, Robin S.; Putt, Karson S.; Allen, Brittany J.; Leslie, Benjamin J.; Nesterenko, Vitaliy; Hergenrother, Paul J.; J. Am. Chem. Soc. 127 (24), 2005, 8686). Free amino functions may be further modified following procedures known in the art to introduce residues $R_8$ other than hydrogen. For example, novel ligands of the sulfonamide class (Y=N—$SO_2R$ such as compounds of the above formula VI) may be obtained by conversion of the corresponding amine (compound of the below formula VII with Y=NH) with a suitable halogenide Cl—$R_{20}$ in analogy to J. Lee et al., J. Med. Chem. 2003, 46, 3116; or in analogy to W. Anderson, Synth. Commun. 19, 1989, 2237-2242; an example is the reaction of a ligand II or II', where X is nitrogen, with a sulfochloride Cl—SO$_2$R:

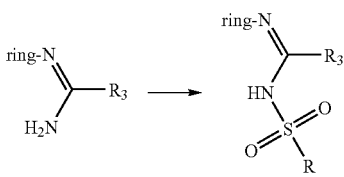

where "ring" stands for the cyclic moiety

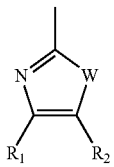

and R$_3$ may, in the synthesis for compounds of the formula II', may also stand for the bridging group R'$_3$ (dimer, 2 reaction centres converted).

The amine may be obtained, for example in analogy to methods described in DE-A-2333378. For example, the educts 2-aminothiophenol and 4-dimethylamino-2-nitrobenzaldehyde may be reacted to obtain (4-benzothiazol-2-yl-3-nitrophenyl)-dimethylamine, whose nitro group may be reduced to the amine in a conventional manner (e.g. using SnCl$_2$/HCl), and the product is reacted with methane sulfochloride.

The metal complexes of the present invention can be prepared from readily available salts of the metals and the ligands as described, including the ligands of the present invention of the formula VII

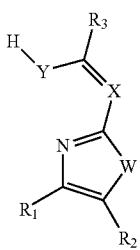

(VII)

and tautomers thereof, wherein all symbols are as defined above for formulae I and II, according to usual methods known from the prior art; see, for example, WO06/000544 and literature cited therein.

Iridium metal complexes of formula Ir(L$^a$)$_2$L', where L$^a$ and L' independently stand for the 2 classes of bidentate ligands [CyC, CyN] and formula II featured in the present invention, can, for example, be prepared by first preparing an intermediate iridium dimer of formula

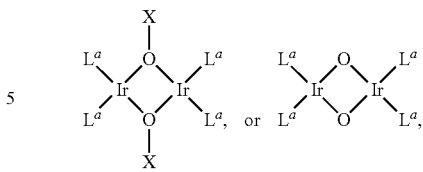

wherein X is H or lower alkyl such as methyl or ethyl, and L$^a$ is as defined above, and then addition of HL'. The iridium dimers can generally be prepared by first reacting iridium trichloride hydrate with HL$^a$ and adding NaX, and by reacting iridium trichloride hydrate with HL$^a$ in a suitable solvent, such as 2-ethoxyethanol.

The present invention is also directed to an electronic device comprising the metal complex and its fabrication process. The electronic device can comprise at least one organic active material positioned between two electrical contact layers, wherein at least one of the layers of the device includes the metallic complex compound. The electronic device can comprise an anode layer (a), a cathode layer (e), and an active layer (c). Adjacent to the anode layer (a) is an optional hole-injecting/transport layer (b), and adjacent to the cathode layer (e) is an optional electron-injection/transport layer (d). Layers (b) and (d) are examples of charge transport layers.

The active layer (c) can comprise at least approximately 1 weight percent of metal complex of present invention.

In some embodiments, the active layer (c) may be substantially 100% of the metal complex because a host charge transporting material, such as Alq$_3$ (see below) is not needed. By "substantially 100%" it is meant that the metal complex is the only material in the layer, with the possible exception of impurities or adventitious by-products from the process to form the layer. Still, in some embodiments, the metal complex may be a dopant within a host material, which is typically used to aid charge transport within the active layer (c). The active layer (c), including any of the metal complexes, can be a small molecule active material.

The device may include a support or substrate adjacent to the anode layer (a) or the cathode layer (e). Most frequently, the support is adjacent the anode layer (a). The support can be flexible or rigid, organic or inorganic. Generally, glass or flexible organic films are used as a support. The anode layer (a) is an electrode that is more efficient for injecting holes compared to the cathode layer (e). The anode can include materials containing a metal, mixed metal, alloy, metal oxide or mixed-metal oxide. Suitable metal elements within the anode layer (a) can include the Groups 4, 5, 6, and 8-11 transition metals. If the anode layer (a) is to be light transmitting, mixed-metal oxides of Groups 12, 13 and 14 metals, such as indium-tin-oxide, may be used. Some non-limiting, specific examples of materials for anode layer (a) include indium-tin-oxide ("ITO"), aluminum-tin-oxide, gold, silver, copper, nickel, and selenium.

The anode layer (a) may be formed by a chemical or physical vapor deposition process or spin-cast process. Chemical vapor deposition may be performed as a plasma-enhanced chemical vapor deposition ("PECVD") or metal organic chemical vapor deposition ("MOCVD").

Physical vapor deposition can include all forms of sputtering (e.g., ion beam sputtering), e-beam evaporation, and resistance evaporation.

Specific forms of physical vapor deposition include rf magnetron sputtering or inductively-coupled plasma physical vapor deposition ("ICP-PVD"). These deposition techniques are well-known within the semiconductor fabrication arts.

A hole-transport layer (b) may be adjacent the anode. Both hole transporting small molecule compounds and polymers can be used.

Commonly used hole transporting molecules include: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis (9H-carbazol-9-yl)cyclobutane (DCZB), N,N,N',N'-tetrakis (4-methylphenyl)-(1,1'-biphenyl)-4,4'-diamine (TTB), 4,4'-N,N-dicarbazole-biphenyl (CBP), N,N-dicarbazoyl-1,4-dimethene-benzene (DCB), porphyrinic compounds, and combinations thereof.

Commonly used hole transporting polymers are polyvinylcarbazole, (phenylmethyl) polysilane, poly(3,4-ethylendioxythiophene) (PEDOT), and polyaniline. Hole-transporting polymers can be obtained by doping hole-transporting molecules such as those mentioned above into polymers such as polystyrene and polycarbonate.

The hole-injection/transport layer (b) can be formed using any conventional means, including spin-coating, casting, and printing, such as gravure printing. The layer can also be applied by ink jet printing, thermal patterning, or chemical, or physical vapor deposition.

Usually, the anode layer (a) and the hole-injection/transport layer (b) are patterned during the same lithographic operation. The pattern may vary as desired. The layers can be formed in a pattern by, for example, positioning a patterned mask or resist on the first flexible composite barrier structure prior to applying the first electrical contact layer material. Alternatively, the layers can be applied as an overall layer (also called blanket deposit) and subsequently patterned using, for example, a patterned resist layer and wet-chemical or dry-etching techniques. Other processes for patterning that are well known in the art can also be used. When the electronic devices are located within an array, the anode layer (a) and hole injection/transport layer (b) typically are formed into substantially parallel strips having lengths that extend in substantially the same direction.

The active layer (c) may comprise the metal complexes described herein. The particular material chosen may depend on the specific application, potentials used during operation, or other factors. The active layer (c) may comprise a host material capable of transporting electrons and/or holes, doped with an emissive material that may trap electrons, holes, and/or excitons, such that excitons relax from the emissive material via a photoemissive mechanism. Active layer (c) may comprise a single material that combines transport and emissive properties. Whether the emissive material is a dopant or a major constituent, the active layer may comprise other materials, such as dopants that tune the emission of the emissive material. Active layer (c) may include a plurality of emissive materials capable of, in combination, emitting a desired spectrum of light. Examples of phosphorescent emissive materials include the metal complexes of the present invention. Examples of fluorescent emissive materials include DCM and DMQA. Examples of host materials include $Alq_3$, CBP and mCP. Examples of emissive and host materials are disclosed in U.S. Pat. No. 6,303,238, which is incorporated by reference in its entirety.

The active layer (c) can be applied from solutions by any conventional technique, including spin coating, casting, microgravure coating, roll-coating, wire bar-coating, dip-coating, spray-coating, and printing techniques such as screen-printing, flexography, offset-printing, gravure-printing and ink-jet printing. The active organic materials may also be applied directly by vapor deposition processes, depending upon the nature of the materials.

The solvent used in the solution processing method is not particularly limited and preferable are those which can dissolve or uniformly disperse the materials. Preferably the materials may be dissolved in a solvent, the solution deposited onto a substrate, and the solvent removed to leave a solid film. Any suitable solvents may be used to dissolve the ionic compounds, provided it is inert, may dissolve at least some material and may be removed from the substrate by conventional drying means (e.g. application of heat, reduced pressure, airflow, etc.). Suitable organic solvents include, but are not limited to, are aromatic or aliphatic hydrocarbons, halogenated such as chlorinated hydrocarbons, esters, ethers, ketones, amide, such as chloroform, dichloroethane, tetrahydrofuran, toluene, xylene, ethyl acetate, butyl acetate, methyl ethyl ketone, acetone, dimethyl formamide, dichlorobenzene, chlorobenzene, propylene glycol monomethyl ether acetate (PGMEA), and alcohols, and mixtures thereof. Also water and mixtures with water miscible solvents are possible.

Optional layer (d) can function both to facilitate electron injection/transport, and also serve as a buffer layer or confinement layer to prevent quenching reactions at layer interfaces. More specifically, layer (d) may promote electron mobility and reduce the likelihood of a quenching reaction if layers (c) and (e) would otherwise be in direct contact. Examples of materials for optional layer (d) include metal-cheated oxinoid compounds (e.g., tris(8-hydroxyquinolato) aluminum ($Alq_3$) or the like); phenanthroline-based compounds (e.g., 2,9-dimethyl-4,7-diphenyl-1,10-phenanthroline ("DDPA"), 4,7-diphenyl-1,10-phenanthroline ("DPA"), or the like; azole compounds (e.g., 2-(4-biphenylyl)-5-(4-t-butylphenyl)-1,3,4-oxadiazole ("PBD") or the like, 3-(4-biphenylyl)-4-phenyl-5-(4-t-butylphenyl)-1,2,4-triazole ("TAZ") or the like; other similar compounds; or any one or more combinations thereof. Alternatively, optional layer (d) may be inorganic and comprise BaO, LiF, $Li_2O$, or the like.

The electron injection/transport layer (d) can be formed using any conventional means, including spin-coating, casting, and printing, such as gravure printing. The layer can also be applied by ink jet printing, thermal patterning, or chemical or physical vapor deposition.

The cathode layer (e) is an electrode that is particularly efficient for injecting electrons or negative charge carriers. The cathode layer (e) can be any metal or nonmetal having a lower work function than the first electrical contact layer (in this case, the anode layer (a)). Materials for the second electrical contact layer can be selected from alkali metals of Group 1 (e.g., Li, Na, K, Rb, Cs), the Group 2 (alkaline earth) metals, the Group 12 metals, the rare earths, the lanthanides (e.g., Ce, Sm, Eu, or the like), and the actinides. Materials, such as aluminum, indium, calcium, barium, yttrium, and magnesium, and combinations thereof, may also be used. Li-containing organometallic compounds, LiF, and $Li_2O$ can also be deposited between the organic layer and the cathode layer to lower the operating voltage. Specific non-limiting examples of materials for the cathode layer (e) include barium, lithium, cerium, cesium, europium, rubidium, yttrium, magnesium, or samarium.

The cathode layer (e) is usually formed by a chemical or physical vapor deposition process. In general, the cathode layer will be patterned, as discussed above in reference to the anode layer (a) and optional hole injecting layer (b). If the device lies within an array, the cathode layer (e) may be patterned into substantially parallel strips, where the lengths of the cathode layer strips extend in substantially the same direction and substantially perpendicular to the lengths of the anode layer strips.

Electronic elements called pixels are formed at the cross points (where an anode layer strip intersects a cathode layer strip when the array is seen from a plan or top view).

In other embodiments, additional layer (s) may be present within organic electronic devices. For example, a layer between the hole injecting layer (b) and the active layer (c) may facilitate positive charge transport, band-gap matching of the layers, function as a protective layer, or the like. Similarly, additional layers between the electron injecting layer (d) and the cathode layer (e) may facilitate negative charge transport, band-gap matching between the layers, function as a protective layer, or the like. Layers that are known in the art can be used. Some or all of the layers may be surface treated to increase charge carrier transport efficiency. The choice of materials for each of the component layers may be determined by balancing the goals of providing a device with high device efficiency with the cost of manufacturing, manufacturing complexities, or potentially other factors.

The charge transport layers (b) and (d) are generally of the same type as the materials of the active layer (c). More specifically, if the active layer (c) has a small molecule compound, then the charge transport layers (b) and (d), if either or both are present, can have a different small molecule compound. If the active layer (c) has a polymer, the charge transport layers (b) and (d), if either or both are present, can also have a different polymer. Still, the active layer (c) may be a small molecule compound, and any of its adjacent charge transport layers may be polymers.

Each functional layer may be made up of more than one layer. For example, the cathode layer may comprise a layer of a Group I metal and a layer of aluminum. The Group I metal may lie closer to the active layer (c), and the aluminum may help to protect the Group I metal from environmental contaminants, such as water.

Although not meant to limit, the different layers may have the following range of thicknesses: inorganic anode layer (a), usually no greater than approximately 500 nm, for example, approximately 50-200 nm; optional hole-injecting layer (b), usually no greater than approximately 100 nm, for example, approximately 50-200 nm; active layer (c), usually no greater than approximately 100 nm, for example, approximately 10-80 nm; optional electron-injecting layer (d), usually no greater than approximately 100 nm, for example, approximately 10-80 nm; and cathode layer (e), usually no greater than approximately 1000 nm, for example, approximately 30-500 nm. If the anode layer (a) or the cathode layer (e) needs to transmit at least some light, the thickness of such layer may not exceed approximately 100 nm.

The location of the electron-hole recombination zone in the device, and thus the emission spectrum of the device, can be affected by the relative thickness of each layer. For example, when a potential light-emitting compound, such as $Alq_3$ is used in the electron transport layer (d), the electron-hole recombination zone can lie within the $Alq_3$ layer.

The emission would then be that of $Alq_3$, and not a desired sharp emission. Thus, the thickness of the electron-transport layer should be chosen so that the electron-hole recombination zone lies within the light-emitting layer (i.e., active layer (c)). The desired ratio of layer thicknesses can depend on the exact nature of the materials used.

The efficiency of the devices made with metal complexes can be further improved by optimizing the other layers in the device. For example, more efficient cathodes such as Ca, Ba, Mg/Ag, or LiF/Al can be used. Shaped substrates and hole transport materials that result in a reduction in operating voltage or increase quantum efficiency are also applicable. Additional layers can also be added to tailor the energy levels of the various layers and facilitate electroluminescence.

Depending upon the application of the electronic device, the active layer (c) can be a light-emitting layer that is activated by a signal (such as in a light-emitting diode) or a layer of material that responds to radiant energy and generates a signal with or without an applied potential (such as detectors or voltaic cells). Examples of electronic devices that may respond to radiant energy are selected from photoconductive cells, photoresistors, photoswitches, phototransistors, and phototubes, and photovoltaic cells. After reading this specification, skilled artisans will be capable of selecting material (s) that for their particular applications.

The electroluminescent devices may be employed for full color display panels in, for example, mobile phones, televisions and personal computer screens. Accordingly the present invention relates also to a device selected from stationary and mobile displays, such as displays for computers, mobile phones, laptops, pdas, TV sets, displays in printers, kitchen equipment, billboards, lightings, information boards and destination boards in trains and buses, containing an organic light emitting diode according to the present invention.

In OLEDs, electrons and holes, injected from the cathode (e) and anode (a) layers, respectively, into the photoactive layer (c), form negative and positively charged polarons in the active layer (c). These polarons migrate under the influence of the applied electric field, forming a polaron exciton with an oppositely charged species and subsequently undergoing radiative recombination. A sufficient potential difference between the anode and cathode, usually less than approximately 20 volts, and in some instances no greater than approximately 5 volts, may be applied to the device. The actual potential difference may depend on the use of the device in a larger electronic component. In many embodiments, the anode layer (a) is biased to a positive voltage and the cathode layer (e) is at substantially ground potential or zero volts during the operation of the electronic device. A battery or other power source (s) may be electrically connected to the electronic device as part of a circuit.

In other embodiments, the metal complex compound can be used as a charge transport material in layer (b) or (d).

The compound does not need to be in a solid matrix diluent (e.g., host charge transport material) when used in layer (b) (c), or (d) in order to be effective. A layer greater than approximately 1% by weight of the metal complex compound, based on the total weight of the layer, and up to substantially 100% of the complex compound can be used as the active layer (c). Additional materials can be present in the active layer (c) with the complex compound. For example, a fluorescent dye may be present to alter the color of emission.

A diluent may also be added. The diluent can be a polymeric material, such as poly(N-vinyl carbazole) and polysilane. It can also be a small molecule, such as 4,4'-N,N'-dicarbazole biphenyl or tertiary aromatic amines. When a diluent is used, the complex compound is generally present in a small amount, usually less than 20% by weight, preferably less than 10% by weight, based on the total weight of the layer.

The metallic complexes may be used in applications other than electronic devices. For example, the complexes may be used as catalysts or indicators (e.g., oxygen-sensitive indicators, phosphorescent indicators in bioassays, or the like).

The following examples illustrate certain features and advantages of the present invention. They are intended to be illustrative of the invention, but not limiting. Unless otherwise indicated, all percentages are by weight, "over night" stands for a time period of 14 to 16 hours, and room temperature denotes a temperature from the range 20-25° C.

ABBREVIATIONS

ITO indium doped tin oxide
Ph phenyl
t- denotes a tertiary (alkyl) group, such as t-Bu standing for tertiary butyl
Bu butyl
LC liquid chromatography
MS mass spectrometry
CIE International Commission on Illumination/chromaticity
NMR nuclear magnetic resonance, of $^1$H if not otherwise indicated
DMSO dimethyl sulfoxide

EXAMPLES

A) Ligands

Example 1

N-Benzothiazol-2-yl-benzamide

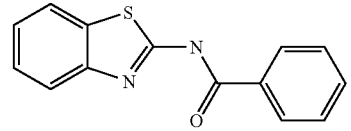 [SMILES: O=C(Nc1nc2ccccc2s1)c1ccccc1]

In a 100 ml three-necked flask equipped with magnetic stirrer, thermometer, dropping funnel and nitrogen inlet, 5.34 g (35.6 mmol) of 2-amino-benzothiazole are dissolved in 50 ml of pyridine and cooled to 3° C. using an ice bath. 5.0 g of benzoylchloride (35.6 mmol) are added dropwise within 20 minutes, keeping the temperature within the mixture below 5° C. Stirring is continued for another 15 minutes, then the mixture is poured on 500 ml of water. The white suspension is stirred for 1 hour, filtered, the white residue is washed 3 times with 100 ml of water, respectively, and dried over night at 50° C. and 30 mbar. 7.5 g crude product obtained are purified by flash-chromatography using hexane/ethylacetate 3:1 (v/v), yielding 5.8 g of the title product.

$^1$H-NMR (300 MHz, CDCl$_3$): 8.02-7.96 (m, 2H), 7.86-7.78 (m, 1H), 7.55-7.48 (m, 1H), 7.44-7.36 (m, 2H), 7.30-7.24 (m, 3H)

Examples 2-6

Compounds of the following Tab. 1 are prepared in analogy to example 1 using corresponding amines and acid chlorides or anhydrides.

TABLE 1

| example | ligand | characterization (NMR) |
|---|---|---|
| 2 | | 12.2 (s, 1H)<br>8.10-8.07 (m, 2H)<br>7.7-7.50 (m, 5H)<br>7.05 (dxd, 1H)<br>3.81 (s, 3H) |
| 3 | | 12.65 (s, 1H)<br>8.00 (d, 2H)<br>7.61 (d, 1H)<br>7.35 (d, 1H)<br>7.00 (dxd, 1H)<br>6.73 (d, 2H)<br>3.80 (s, 3H)<br>3.00 (s, 6H) |
| 4 | | 3.97 (q, 2H)<br>1.26 (t, 3H) |

TABLE 1-continued

| example | ligand | characterization (NMR) |
|---|---|---|
| 5 | 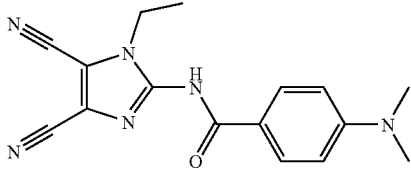 [SMILES: CCn1c(NC(=O)c2ccc(N(C)C)cc2)nc(C#N)c1C#N] | 10.76 (s, 1H)<br>7.83 (d, 2H)<br>6.75 (d, 2H)<br>4.05 (q, 2H)<br>3.01 (s, 6H)<br>1.36 (t, 3H) |
| 6 | 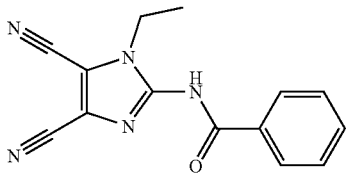 [SMILES: CCn1c(NC(=O)c2ccccc2)nc(C#N)c1C#N] | 11.19 (s, 1H)<br>7.99-7.95 (m, 2H)<br>7.69-7.62 (m, 1H)<br>7.59-7.54 (m, 2H)<br>4.10 (q, 2H)<br>1.38 (t, 3H) |

Example 7

2,2,2-Trifluoro-N-thiazol-2-yl-acetamide

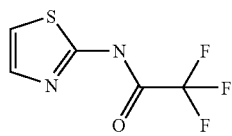 [SMILES: O=C(Nc1nccs1)C(F)(F)F]

Into a 250 ml three-necked flask equipped with magnetic stirrer, thermometer, dropping funnel and nitrogen inlet, 5.0 g (49.9 mmol) of 2-aminothiazol and 14.3 g (99.85 mmol) of ethyltrifluoroacetate in 100 ml of tetrahydrofuran are introduced. A solution of 14.4 g (124.8 mmol) of potassium-t-butylate in 50 ml of tetrahydrofuran is added dropwise within 15 minutes to the stirred brown solution, whose internal temperature is kept in the range 20-25° C. using an ice bath. Stirring is continued for another 75 minutes, then 300 ml of a buffer solution is added and pH 7 is adjusted by addition of 2N aq. HCl. Extraction with 300 ml of ethyl acetate is carried through 3 times, the combined organic phases are washed with 250 250 ml of water, dried over MgSO$_4$, and filtered. After evaporating the solvent, the crude product is recrystallized from 2-propanol, yielding 2.26 g of the title product.

$^1$H-NMR (300 MHz, DMSO): 7.62 (d, 1H), 7.29 (d, 1H),

Examples 8-10

Compounds of the following Tab. 2 are prepared in analogy to example 7 using corresponding amines and esters.

TABLE 2

| example | ligand | characterization (NMR) |
|---|---|---|
| 8 | 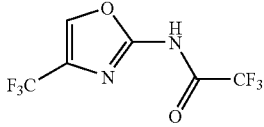 [SMILES: O=C(Nc1nc(C(F)(F)F)co1)C(F)(F)F] | 8.07 (s, 1H) |

TABLE 2-continued

| example | ligand | characterization (NMR) |
|---|---|---|
| 9 | 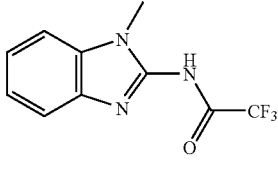 [SMILES: Cn1c(NC(=O)C(F)(F)F)nc2ccccc21] | 12.84 (s, 1H)<br>7.58-7.55 (m, 2H)<br>7.34-7.29 (m, 2H)<br>3.46 (s, 3H) |
| 10 | 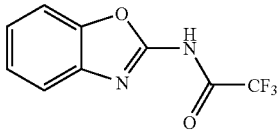 [SMILES: O=C(Nc1nc2ccccc2o1)C(F)(F)F] | 7.67-7.63 (m, 1H)<br>7.54-7.48 (m, 1H)<br>7.43-7.33 (m, 2H) |

Example 11

3-[3-Benzooxazol-(2)-yliden]-1,1,1-trifluor-propan-2-one

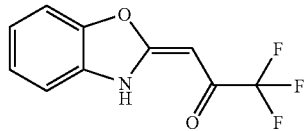 [SMILES: O=C(/C=C1\Nc2ccccc2O1)C(F)(F)F]

Into a 500 ml three-necked flask equipped with magnetic stirrer, thermometer, dropping funnel and nitrogen inlet, 14.0 g (125 mmol) of potassium-t-butylate in 120 ml of tetrahydrofuran are introduced. The clear solution is cooled to 3° C. using an ice bath. A solution of 6.65 g (50 mmol) 2-methyl-benzoxazol and 14.2 g (100 mmol) of ethyltrifluoroacetate in 200 ml of tetrahydrofuran is slowly added within 50 minutes. Stirring at 3° C. is continued for another 60 minutes, then the ice bath is removed and the orange coloured solution is stirred over night at room temperature. Subsequently, 120 ml of an aqueous 10% (w/w) solution of citric acid is added dropwise, and the mixture is poured on 1 l of water with stirring. Extraction with 500 ml of ethyl acetate is carried through 3 times, the combined organic phases are washed 3 times with 100 ml of saturated aq. NaCl, dried over MgSO$_4$, and filtered. After evaporating the solvent, the residue is washed 2 times with 10 ml of ice cooled ethyl acetate, and dried over night at 50° C. and 25 mbar, yielding 7.9 g of the title product.

$^1$H-NMR (300 MHz, DMSO-D$_6$): 7.62-7.57 (m, 1H), 7.54-7.49 (m, 1H), 7.39-7.26 (m, 2H), 5.73 (s, 1H)

Examples 12-14

Compounds of the following Tab. 3 are prepared in analogy to example 11 using corresponding methyl compounds.

TABLE 3

| example | ligand | characterization (NMR) |
|---|---|---|
| 12 | 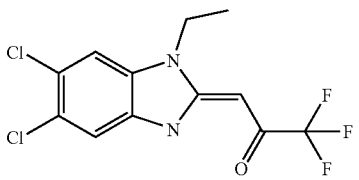 [SMILES: CCN1/C(=C/C(=O)C(F)(F)F)Nc2cc(Cl)c(Cl)cc21] | 7.98 (s, 1H)<br>7.79 (s, 1H)<br>5.54 (s, 1H)<br>4.19 (q, 2H)<br>1.24 (t, 3H) |
| 13 | 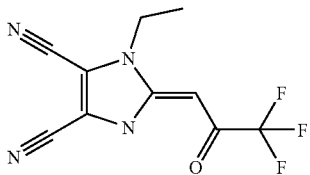 [SMILES: CCN1C(C#N)=C(C#N)N/C1=C\C(=O)C(F)(F)F] | 6.54 (s, 1H)<br>4.32 (q, 2H)<br>1.33 (t, 3H) |
| 14 | 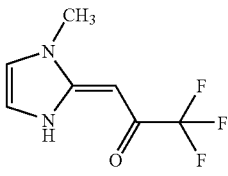 | 7.11 (d, 1H)<br>6.98 (d, 1H)<br>5.28 (s, 1H)<br>3.59 (s, 3H) |

Examples 15 and 16

Compounds of the following Tab. 4 are prepared in analogy to the synthesis of N-(1,3-benzothiazol-2-yl)-benzamidine described by T. George, Synthesis 1974, 346-347.

TABLE 4

| example | ligand | characterization (NMR) |
|---|---|---|
| 15 | 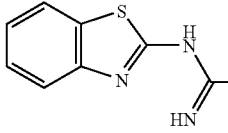 | 7.95 (d, 2H)<br>7.80 (d, 1H)<br>7.67 (d, 1H)<br>7.33 (dxd, 1H)<br>7.20 (dxd, 1H)<br>6.75 (d, 2H)<br>3.00 (s, 6H) |
| 16 | 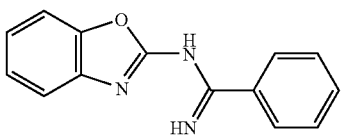 [SMILES: N=C(Nc1nc2ccccc2o1)c1ccccc1] | 9.87 (s, 1H)<br>9.35 (s, 1H)<br>8.11 (m, 2H)<br>7.59-7.50 (m, 4H)<br>7.28-7.18 (m, 3H) |

Example 17

N-(2-Benzthiazol-2-yl-5-dimethylamino-phenyl)-methanesulfonamid

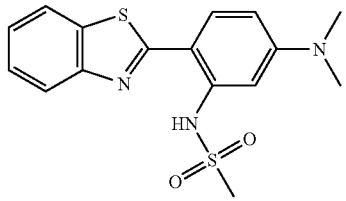 [SMILES: CN(C)c1ccc(-c2nc3ccccc3o2)c(NS(C)(=O)=O)c1]

a) Starting from 2-aminothiophenol and 4-dimethylamino-2-nitro-benzaldehyde, (4-benzthiazol-2-yl-3-nitro-phenyl)-dimethylamin is prepared in analogy to the procedure described in example 1 of DE-A-2333378.

b) In a 250 ml three-necked flask equipped with magnetic stirrer, thermometer, reflux condenser and nitrogen inlet, 15.25 g of (78.8 mmol) anhydrous tin(II) chloride are dissolved in 40 ml of 37% hydrochloric acid, and 6.94 g (23.2 mmol) of (4-benzthiazol-2-yl-3-nitro-phenyl)-dimethylamin (product of part a) are added with stirring. The thick, red suspension heats up to 100° C. The internal temperature is kept at 60° C. for the following 5 hours. After cooling, the reaction mixture is adjusted to pH 14 by addition of 180 ml of a 4N solution of sodium hydroxid, and stirring is continued for another 30 minutes. After filtration, the residue is washed three times with 50 ml of water and dried over night at 50° C. and 25 mbar, yielding 6.49 g of crude 4-benzthiazol-2-yl-N, N-dimethyl-benzene-1,3-diamin, which is used for the subsequent step without further purification.

c) Into a 250 ml three-necked flask equipped with magnetic stirrer, thermometer and nitrogen inlet, 6.20 g (23.0 mmol) of crude 4-benzthiazol-2-yl-N,N-dimethyl-benzene-1,3-diamin (product of part b) in 65 ml of pyridine are introduced and cooled to 3° C. with stirring. 3.19 g (27.6 mmol) of methansulfochloride are added dropwise within 30 Minuten using a syringe, then the ice bath is removed and the black solution is stirred over night at room temperature. The reaction mixture is then poured dropwise into 700 ml of ice water; the reddish brown suspension thus obtained is stirred for 20 minutes, filtered, the residue washed 3 times with 100 ml of ice water, and dried over night at 50° C. and 25 mbar. 7.50 g of the title product are obtained.

$^1$H-NMR (300 MHz, DMSO-D$_6$): 11.89 (s, 1H), 8.04 (d, 1H), 7.84 (d, 1H), 7.70 (d, 1H)
7.52-7.34 (m, 2H)
6.85 (d, 1H)
6.59 (dxd, 1H)
3.17 (s, 3H)
3.03 (s, 6H)

Examples 18 and 19

Compounds of the following Tab. 5 are prepared in analogy to the compound of example 17.

TABLE 5

| example | ligand | characterization (NMR) |
|---|---|---|
| 18 | [structure] | 11.16 (s, 1H)<br>7.94 (d, 1H)<br>7.72-7.69 (m, 2H)<br>7.37-7.33 (m, 2H)<br>6.88-6.87 (m, 1H)<br>6.63-6.60 (m, 1H)<br>3.20 (s, 3H)<br>3.03 (s, 6H) |
| 19 | [structure] | 11.08 (s, 1H)<br>8.22 (dxd, 1H)<br>7.88-7.81 (m, 2H)<br>7.73-7.60 (m, 2H)<br>7.52-7.41 (m, 2H)<br>7.35-7.29 (m, 1H)<br>3.25 (s, 3H) |

B) Intermediate Complexes

The compounds in Table 6 are prepared according to the method shown in example 10 of WO 2006/000544.

TABLE 6

| Example | Structure |
|---|---|
| 20 | [structure] |

TABLE 6-continued

| Example | Structure |
|---|---|
| 21 | 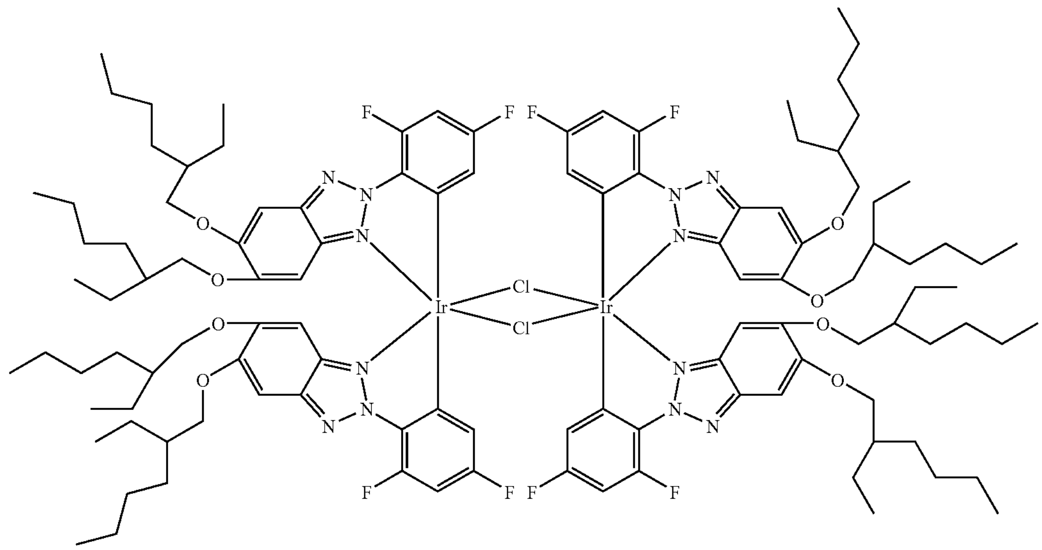 |
| 22 | 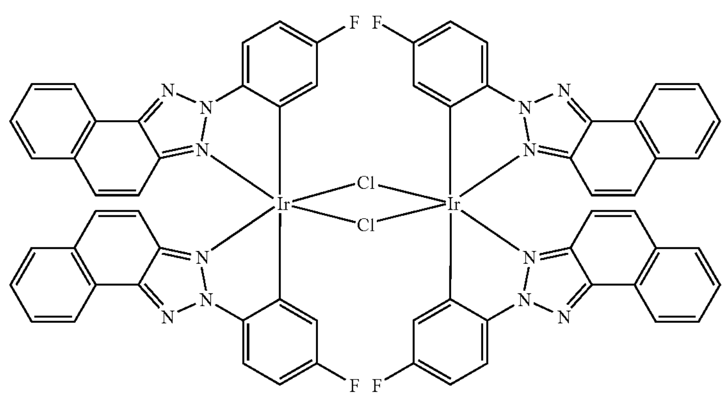 |
| 23 | 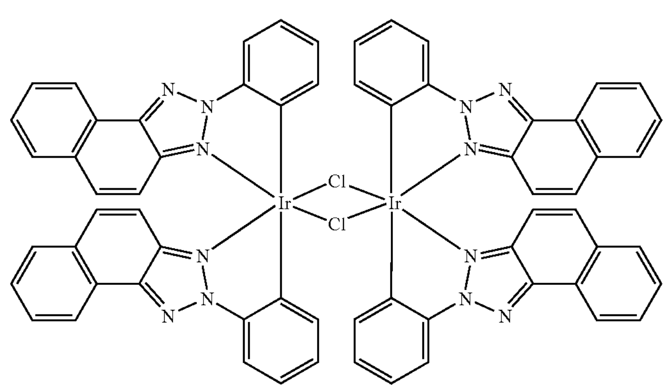 |

TABLE 6-continued

| Example | Structure |
|---|---|
| 24 | (structure shown) |

C) Final Complexes

The compounds in Table 7 are prepared according to the method shown in example 11 of WO 2006/000544.

TABLE 7

| Example | Dimer of | Ligand of | Photoluminescence in Toluene $\lambda_{max}$ [nm] |
|---|---|---|---|
| 25 | Example 20 | Example 1 | 539 |
| 26 | Example 20 | Example 2 | 543 |
| 27 | Example 20 | Example 3 | 550 |
| 28 | Example 20 | Example 4 | 539/565 |
| 29 | Example 20 | Example 5 | 541 |
| 30 | Example 20 | Example 6 | 540/564 |
| 31 | Example 20 | Example 7 | 532 |
| 32 | Example 20 | Example 8 | 525/557 |
| 33 | Example 20 | Example 9 | 538/569 |
| 34 | Example 20 | Example 10 | 530/563 |
| 35 | Example 20 | Example 11 | 538 |
| 36 | Example 20 | Example 12 | 541 |
| 37 | Example 20 | Example 14 | 559/587 |
| 38 | Example 20 | Example 15 | 576 |
| 39 | Example 20 | Example 16 | 559 |
| 40 | Example 20 | Example 17 | 552 |
| 41 | Example 20 | Example 18 | 577 |
| 42 | Example 20 | Example 19 | 541 |
| 43 | Example 20 | 2-(2-Hydroxyphenyl)benzthiazol | 574 |
| 44 | Example 20 | 2-(2-Hydroxyphenyl)benzoxazol | 564 |
| 45 | Example 22 | Example 5 | 516/549 |
| 46 | Example 22 | Example 11 | 515 |
| 47 | Example 23 | Example 5 | 525/554 |
| 48 | Example 23 | Example 11 | 517/550 |
| 49 | Example 24 | Example 4 | 501 |
| 50 | Example 24 | Example 5 | 499 |
| 51 | Example 24 | Example 7 | 458/487 |
| 52 | Example 24 | Example 9 | 464/497 |
| 53 | Example 24 | Example 10 | 544 |
| 54 | Example 24 | Example 11 | 544 |
| 55 | Example 24 | 2-(2-Hydroxyphenyl)benzthiazol | 589 |
| 56 | Example 24 | 2-(2-Hydroxyphenyl)benzoxazol | 507/539 |

Example 57

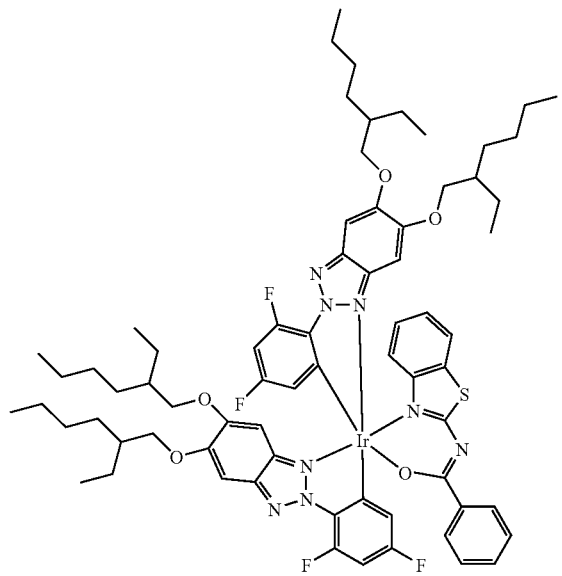

447 mg (0.186 mmol) of the compound prepared in Example 21, 98 mg (0.372 mMol) of silver trifluoromethanesulfonate and 15 ml of 2-nonanone are placed in a 50 ml three necked round bottomed flask, equipped with a magnetic stirrer and a reflux condenser. The yellow suspension is evacuated and purged with nitrogen three times. The reaction mixture is heated to 100° C. internal temperature for two hours, then to 120° C. for one additional hour and then cooled to 50° C. 95 mg (0.372 mMol) of the compound prepared in Example 1 are added to the brown suspension and the resulting reaction mixture is heated to 120° C. internal temperature for 18 hours. The brown suspension is then cooled to room temperature, filtered and the residue washed three times with 20 ml of hexane. The filtrate is evaporated and the crude product purified by flash chromatography using Hexane/Ethylacetate=40:1 as eluent. 60 mg of the desired product are isolated as a yellow powder. The photoluminescence spectrum in toluene shows emission maxima at 507 and 540 nm.

The compounds in Table 8 are prepared according to Example 57:

TABLE 8

| Example | Dimer | Ligand | Photoluminescence in Toluene/$\lambda_{max}$ [nm] |
|---|---|---|---|
| 58 | Example 21 | Example 4 | 508/538 |
| 59 | Example 21 | Example 5 | 505/540 |
| 60 | Example 21 | Example 7 | 507/538 |
| 61 | Example 21 | Example 8 | 506/541 |
| 62 | Example 21 | Example 9 | 506/543 |
| 63 | Example 21 | Example 10 | 507/539 |
| 64 | Example 21 | Example 11 | 508/540 |
| 65 | Example 21 | Example 12 | 509/540 |
| 66 | Example 21 | 2-(2-Hydroxyphenyl)benzthiazol | 535/565 |
| 67 | Example 21 | 2-(2-Hydroxyphenyl)benzoxazol | 515/541 |

Further Examples

Example 68

The following intermediate complex is prepared in analogy to example 10 of WO 2006/000544 using 2-(4-tert.butylphenyl)pyridine as a ligand:

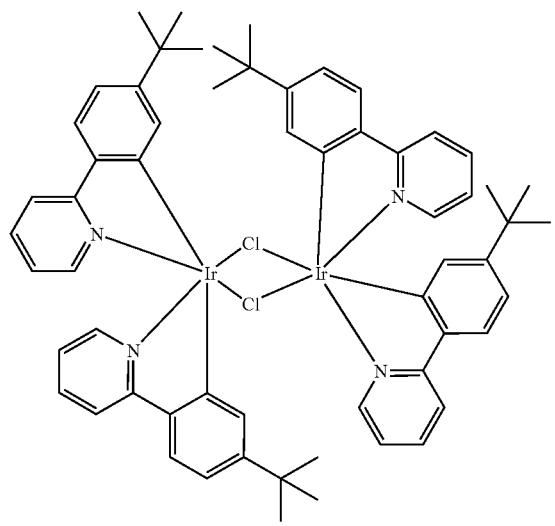

Examples 69-71

The complexes described in Tab. 9 below are prepared in analogy to those described in Tab. 7.

TABLE 9

| Luminiscent complexes from intermediate of example 68 | | |
|---|---|---|
| Example No. | Ligand of | Photoluminescence in Toluene $\lambda_{max}$ [nm] |
| 69 | Example 7 | 500/533 |
| 70 | Example 9 | 500/535 |
| 71 | Example 14 | 512 |

Application Examples

An organic luminescence device having a single organic light-emitting layer is prepared in the following manner: On a glass substrate, a 75 nm thick ITO film formed by sputtering and subsequently patterned by oxygen-plasma treatment (commercially available at Thin Film Devices (TFD), USA). Onto the ITO film, a 80 nm thick hole-injection layer using PEDOT:PSS (poly(3,4-ethylenedioxythiophene) poly(styrene sulfonate); available under the trade name Baytron® P AI 4083) is formed by spin-coating followed by heating at 200° C. (6 minutes). A solution of 48 mg of compound prepared in one of the above examples and indicated in the following Table 9, 468 mg of poly(9-vinylcarbazole) (PVK), 265 mg of 2-(4-biphenylyl)-5-(4-tert.butylphenyl)-1,3,4-oxadiazole (PBD) and 220 mg of N,N'-bis(3-methylphenyl)-N,N'-diphenylbenzidine (TPD, CAS-No. 65181-78-4) in 46.7 ml of toluene are applied by spin coating (950 rpm.; 50 seconds) to obtain a thickness of 80 nm. After the thus-treated substrate has been set in a vacuum deposition chamber, a cathode having a two-layer electrode structure is formed by depositing 5 nm barium followed by 70 nm aluminum. The following table 10 shows colour data (CIE-data x, y) and efficacy when the device is driven to emit 100 cd/sqm luminance, and corresponding current density and voltage.

TABLE 10

| Colour (CIE x, y) and light emitting efficacy of device driven at 100 cd/m² | | | | |
|---|---|---|---|---|
| Complex of Example No. | CIE x, y | efficacy cd/A | voltage V | current density mA/cm² |
| 25 | 0.45, 0.53 | 1.4 | 8.4 | 70 |
| 26 | 0.46, 0.52 | 1.3 | 8.6 | 75 |
| 27 | | | | |
| 28 | 0.50, 0.49 | 2.6 | 12.4 | 34 |
| 29 | 0.46, 0.53 | 1.2 | 7.2 | 85 |
| 30 | 0.45, 0.54 | 0.3 | 8.0 | 337 |
| 31 | 0.44, 0.54 | 1.0 | 8.3 | 104 |
| 32 | | | | |
| 33 | 0.46, 0.53 | 1.1 | 7.4 | 90 |
| 34 | 0.43, 0.55 | 0.8 | 9.6 | 135 |
| 35 | 0.45, 0.53 | 1.0 | 7.6 | 102 |
| 36 | 0.48, 0.51 | 10 | 6.3 | 10 |
| 37 | 0.51, 0.48 | 2.0 | 6.2 | 51 |
| 38 | 0.53, 0.46 | 0.8 | 8.6 | 133 |
| 39 | 0.51, 0.48 | 1.4 | 7.5 | 70 |
| 40 | | | | |
| 41 | | | | |
| 42 | 0.48, 0.50 | 0.4 | 8.6 | 256 |
| 43 | 0.52, 0.47 | 2.9 | 6.2 | 34 |
| 44 | 0.52, 0.48 | 3.3 | 5.9 | 30 |
| 45 | | | | |
| 46 | | | | |

TABLE 10-continued

Colour (CIE x, y) and light emitting efficacy of device driven at 100 cd/m²

| Complex of Example No. | CIE x, y | efficacy cd/A | voltage V | current density mA/cm² |
|---|---|---|---|---|
| 47 | | | | |
| 48 | | | | |
| 49 | | | | |
| 50 | | | | |
| 51 | | | | |
| 52 | | | | |
| 53 | | | | |
| 54 | | | | |
| 55 | | | | |
| 56 | | | | |
| 57 | | | | |
| 58 | | | | |
| 59 | 0.41, 0.54 | 5.0 | 5.6 | 20 |
| 60 | 0.41, 0.54 | 3.1 | 6.5 | 32 |
| 61 | | | | |
| 62 | 0.38, 0.56 | 6.4 | 5.6 | 13 |
| 63 | | | | |
| 64 | 0.42, 0.53 | 2.4 | 7.1 | 42 |
| 65 | 0.43, 0.52 | 5.9 | 6.1 | 17 |
| 66 | | | | |
| 67 | | | | |
| 69 | 0.29, 0.56 | 2.1 | 6.48 | 46 |
| 70 | 0.28, 0.60 | 3.0 | 5.52 | 33 |
| 71 | 0.32, 0.61 | 1.3 | 6.6 | 59 |

The invention claimed is:

1. Compound of the formula I or I'

[LDH]$_n$M[L]$_m$     (I)

[LTH](M[L]$_p$)$_2$     (I')

wherein
n is an integer 1 or 2,
m and p each is an integer 1 or 2,
the sum (n+m) being 2 or 3,
M is a metal with an atomic weight of greater than 40,
L is a moiety

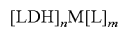
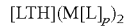

consisting of
2 monodentate ligands CyC and CyN or CyC and CyC, or
1 bidentate ligand other than LDH or LTH, wherein the 2 moieties CyC and CyN, or CyC and CyC, are interlinked by a chemical bond,
wherein CyC is an organic moiety containing a carbon atom bonding to M, and CyN is a cyclic organic moiety containing a nitrogen atom bonding to M;
LDH is a bidentate ligand of the formula II

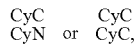

and LTH is a dimer of LDH, binding to 2 metal atoms M, of the formula II'

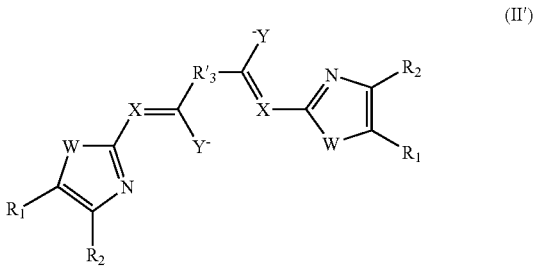

wherein

W is selected from O, S, NR$_4$ and CR$_5$R$_6$,

X is N or CH,

Y is selected from O, S and NR$_8$;

R$_1$ and R$_2$ independently are H, unsubstituted or substituted C$_1$-C$_{18}$alkyl, unsubstituted or substituted C$_2$-C$_{18}$alkenyl, unsubstituted or substituted C$_5$-C$_{10}$aryl, unsubstituted or substituted C$_5$-C$_{10}$heteroaryl, C$_1$-C$_{18}$acyl, halogen, C$_1$-C$_{18}$alkoxy, C$_1$-C$_{18}$alkylthio, C$_3$-C$_{12}$cycloalkyl, C$_1$-C$_{18}$acyloxy, C$_5$-C$_{10}$aryloxy, C$_3$-C$_{12}$cycloalkyloxy, COR, CH=NR, CH=N—OH, CH=N—OR, COOR, CONHR, CONRR', CONH—NHR, CONH—NRR', SO$_2$R, SO$_3$R, SO$_2$NHR, SO$_2$NRR',

SO$_2$NH—NHR, SO$_2$NH—NRR', S(O)R, S(O)OR, S(O)NHR, S(O)NRR', S(O)NH—NHR,

S(O)NH—NRR', SiRR'R", PORR', PO(OR)R', PO(OR)$_2$, PO(NHR)$_2$, PO(NRR')$_2$, CN, NO$_2$, NHR, NRR', NH—NHR, NH—NRR' or CONROH;

R is H, C$_1$-C$_{12}$alkyl, C$_5$-C$_{10}$aryl or C$_3$-C$_{12}$cycloalkyl,

R' and R" independently are selected from C$_1$-C$_{12}$alkyl, C$_5$-C$_{10}$aryl and C$_3$-C$_{12}$cycloalkyl, or neighbouring residues R$_1$ and R$_2$ form an organic bridging group completing, together with the carbon atoms they are bonding to, a carbocyclic or heterocyclic, non-aromatic or aromatic ring of 5 to 7 ring atoms in total, which optionally may be substituted;

R$_4$, R$_5$, R$_6$ independently are H, unsubstituted or substituted C$_1$-C$_{18}$alkyl, unsubstituted or substituted C$_2$-C$_{18}$alkenyl, unsubstituted or substituted C$_5$-C$_{10}$aryl, unsubstituted or substituted C$_2$-C$_{10}$heteroaryl, C$_1$-C$_{18}$acyl;

R$_3$ is H, unsubstituted or substituted C$_1$-C$_{18}$alkyl, unsubstituted or substituted C$_2$-C$_{18}$alkenyl, unsubstituted or substituted C$_5$-C$_{10}$aryl, unsubstituted or substituted C$_2$-C$_{10}$heteroaryl, C$_1$-C$_{18}$acyl, OR, SR, NRR', or is C$_2$-C$_5$alkynyl, C$_3$-C$_5$cycloalkyl, hetero-C$_2$-C$_5$cycloalkyl or C$_3$-C$_5$cycloalkenyl each unsubstituted or mono- or poly-substituted by COR, COOR, CONRR', CN, halogen and/or by OR;

R'$_3$ is unsubstituted or substituted C$_1$-C$_{18}$alkylene, unsubstituted or substituted C$_2$-C$_{18}$alkenylene, unsubstituted or substituted C$_5$-C$_{10}$arylene, unsubstituted or substituted C$_2$-C$_{10}$heteroarylene or C$_2$-C$_{18}$diacylene; and R$_8$ is hydrogen or a substituent.

2. Compound of claim 1, wherein formula I is formula (III) or tautomeric forms thereof,

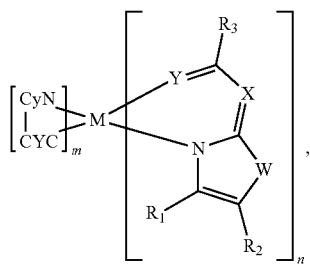 (III)

wherein

is a bidentate C,N-binding ligand, CyC and CyN are interlinked by a chemical bond, n is 1, M is Ir and m is 2 or M is Pt and m is 1;

W is O, S, $NR_4$, $CR_5R_6$,

X is N or CH,

Y is O or $NR_8$;

$R_1$, $R_2$ independently are selected from H, $C_1$-$C_8$alkyl, phenyl, halogen, $C_1$-$C_8$alkoxy, CN, NHR, NRR';

or $R_1$ and $R_2$ together with the carbon atoms they are bonding to form an annellated phenyl ring, which optionally may be substituted;

$R_3$ is H, unsubstituted or substituted $C_1$-$C_8$alkyl, unsubstituted or substituted $C_2$-$C_8$alkenyl, unsubstituted or substituted phenyl;

$R_4$, $R_5$, $R_6$ independently are H or $C_1$-$C_8$alkyl;

$R_8$ is H, $C_1$-$C_8$alkyl, COR, $SO_2R$; and

R and R' independently are selected from $C_1$-$C_6$alkyl, and R may also be hydrogen.

3. Compound of claim 2, wherein

is

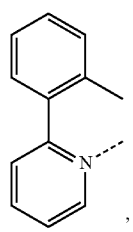 (VI-1)

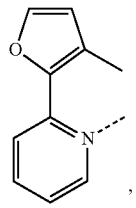 (VI-2)

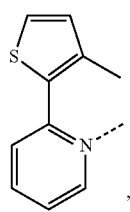 (VI-3)

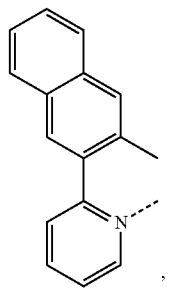 (VI-4)

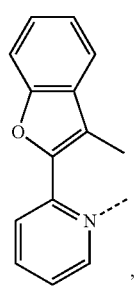 (VI-5)

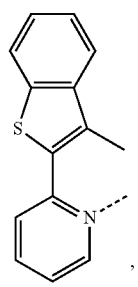 (VI-6)

(VI-7)

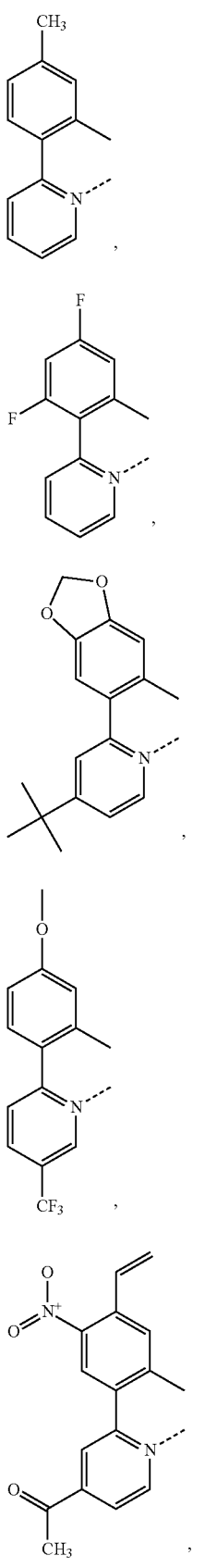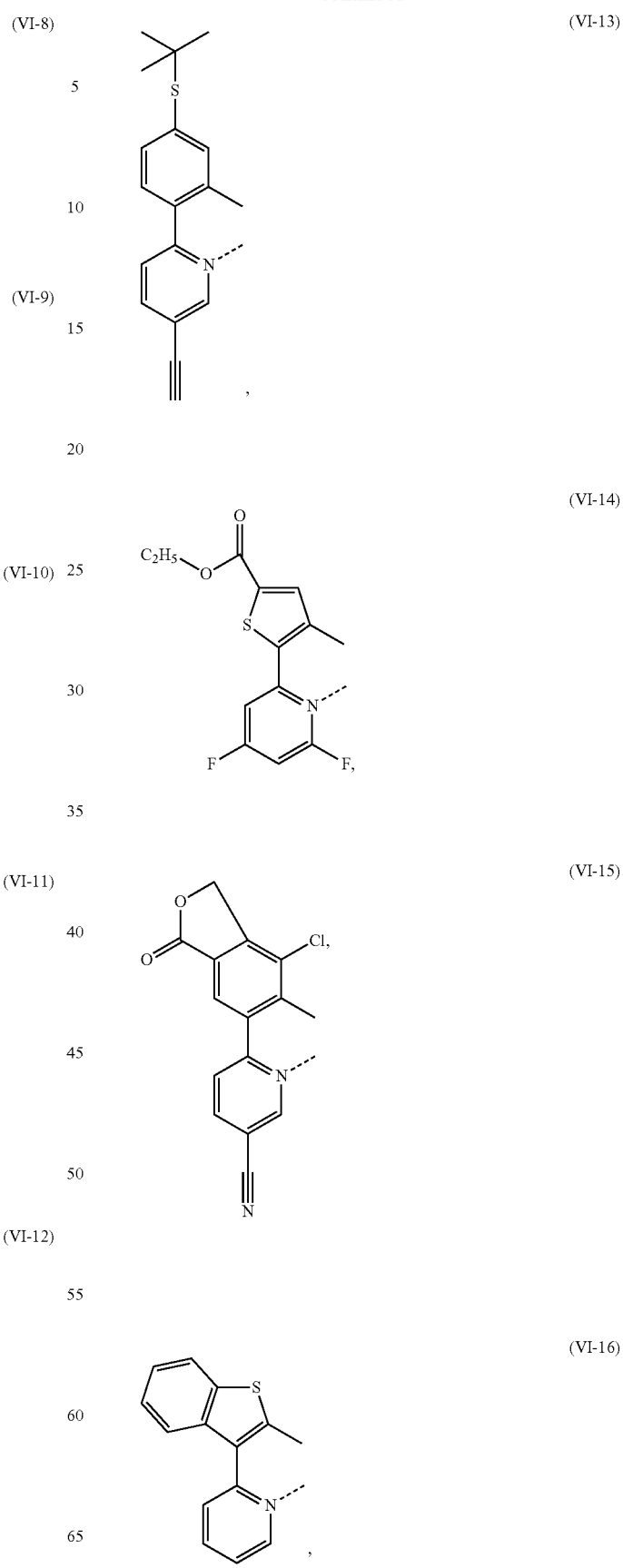

(VI-17) 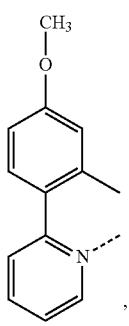
(VI-18) 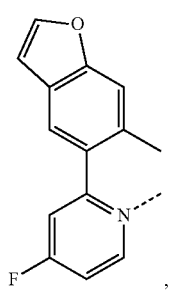
(VI-19) 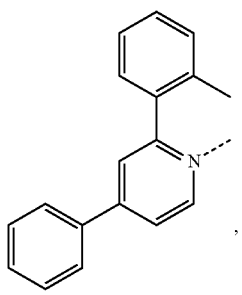
(VI-20) 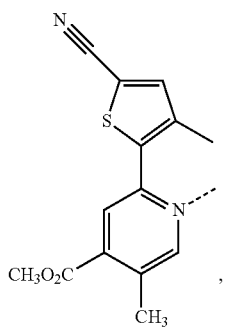
(VI-21) 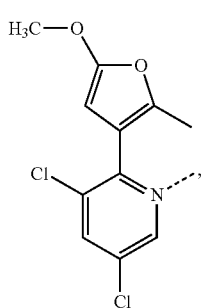
(VI-22) 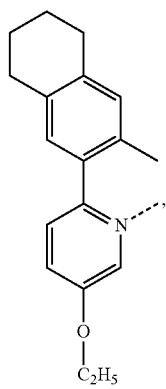
(VI-23) 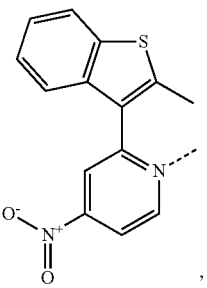
(VI-24) 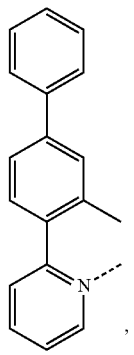
(VI-25) 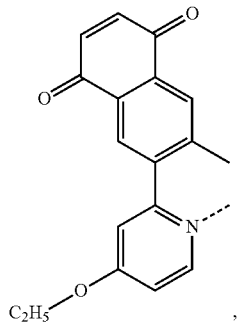

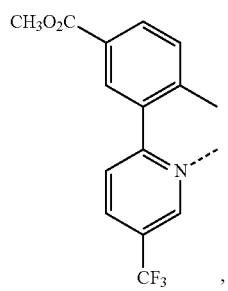
(VI-26)
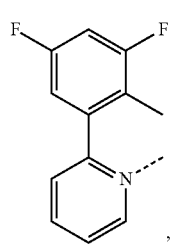
(VI-27)
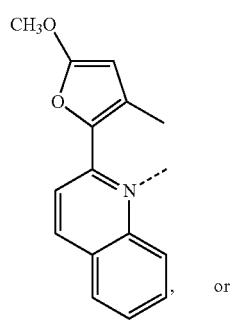
(VI-28)
or
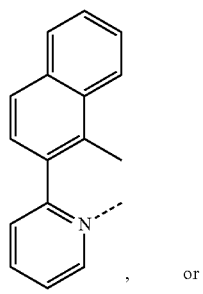
(VI-29)
or
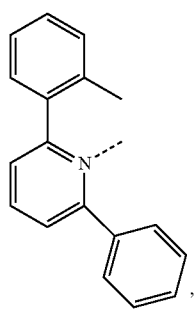
(VI-30)
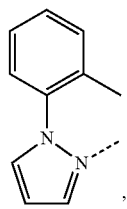
(VI-31)
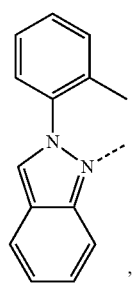
(VI-32)
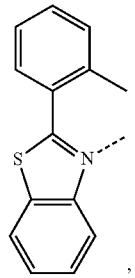
(VI-33)
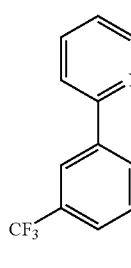
(VI-34)
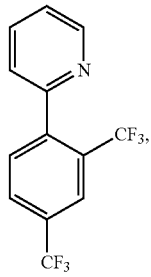
(VI-35)
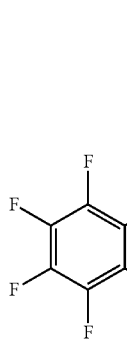
(VI-36)

-continued
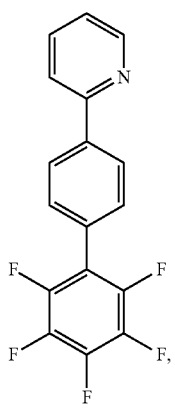
(VI-37)
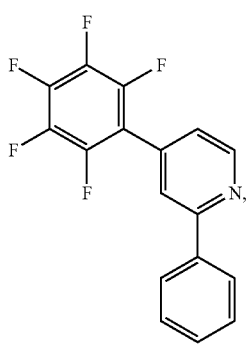
(VI-37-A)
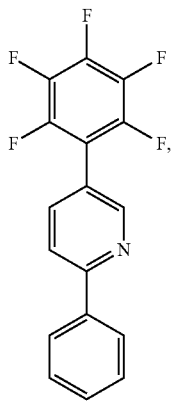
(VI-38)
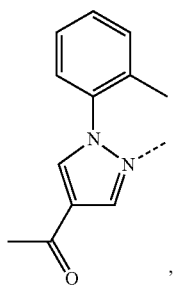
(VI-39)
-continued
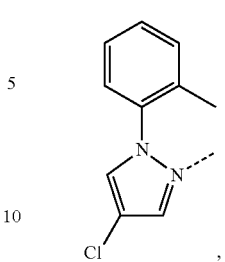
(VI-40)
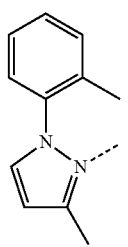
(VI-41)
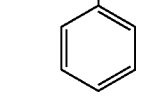
(VI-42)
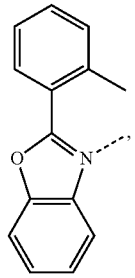
(VI-43)
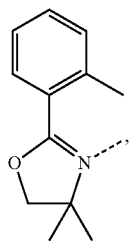
(VI-44)

4. Compound of claim 1 of formula (I) or (I') wherein

Y is O or $NR_8$;

M is selected from Tl, Pb, Bi, In, Sn, Sb, Te, Mo, Cr, Mn, Ta, V, Cu, Fe, Ru, Ni, Co, Ir, Pt, Pd, Rh, Re, Os, Ag and Au;

$R_1$, $R_2$, $R_3$, $R_4$, $R_5$, $R_6$, $R_8$ are as defined above and, if substituted, the substituent is selected from halogen, $C_1$-$C_{12}$alkoxy, $C_1$-$C_{12}$alkylthio, benzoyl substituted by $C_1$-$C_4$alkyl or $C_1$-$C_4$alkoxy or halogen, benzoyloxy substituted by $C_1$-$C_4$alkyl or $C_1$-$C_4$alkoxy or halogen, phenyl, phenyloxy, $C_3$-$C_{12}$cycloalkyl, $C_3$-$C_{12}$cycloalkyloxy, or from the residues COR, OCOR, COOR, CONHR, CONRR', $SO_2R$, $SO_3R$, $SO_2NHR$, $SO_2NRR'$, SiRR'R", PORR', PO(OR)R', $PO(OR)_2$, CN, $NO_2$, NHR, NRR', NH—NHR, NH—NRR', where R, R' and R" independently are selected from $C_1$-$C_{12}$alkyl, $C_1$-$C_6$haloalkyl, phenyl, cyclopentyl, cyclohexyl; and R may also be hydrogen.

5. Compound according to claim 1, wherein L is selected from the ligands:

a) of formula

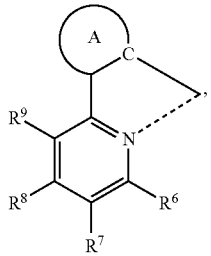

wherein $R^6$, $R^7$, $R^8$, and $R^9$ are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, acyl, alkyloxycarbonyl, a nitro group, or a halogen atom; or two substituents $R^6$, $R^7$, $R^8$, and $R^9$, which are adjacent to each other, together form a group

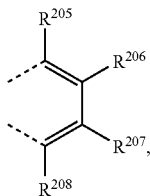

wherein $R^{205}$, $R^{206}$, $R^{207}$ and $R^{208}$ are independently of each other H, or $C_1$-$C_8$alkyl, the ring A represents an optionally substituted aryl or heteroaryl group; or the ring A may be taken with the pyridyl group binding to the ring A to form a ring; the alkyl group, alkenyl group, alkynyl group, aryl group, heteroaryl group, alkoxy group, alkylthio group, acyl group, and alkyloxycarbonyl group represented by $R^6$, $R^7$, $R^8$, and $R^9$ may be substituted;

b) of formula

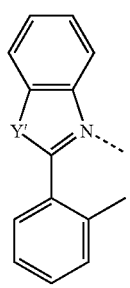

wherein Y' is S, O, $NR^{200}$, wherein $R^{200}$ is hydrogen, cyano, $C_1$-$C_4$alkyl, $C_2$-$C_4$alkenyl, $C_6$-$C_{10}$aryl, —$(CH_2)_{r'}$—Ar wherein Ar is $C_6$-$C_{10}$aryl, a group —$(CH_2)_{r'}X^{20}$, wherein r' is an integer of 1 to 5, $X^{20}$ is halogen, hydroxy, —O—$C_1$-$C_4$alkyl, di($C_1$-$C_4$alkyl)amino, amino, or cyano; a group —$(CH_2)_rOC(O)(CH_2)_{r''}CH_3$, wherein r is 1, or 2, and r'' is 0, or 1;

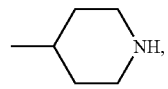

—NH-Ph, —C(O)CH$_3$, —CH$_2$—O—(CH$_2$)$_2$—Si(CH$_3$)$_3$, or

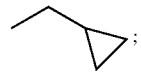

c) of formula

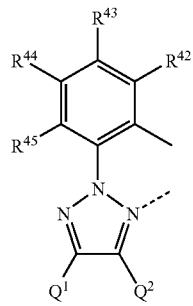 or 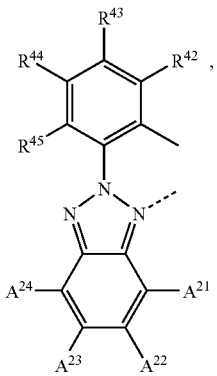

wherein $Q^1$ and $Q^2$ are independently of each other hydrogen, $C_1$-$C_{24}$alkyl, or $C_6$-$C_{18}$aryl, $A^{21}$ is hydrogen, halogen, $C_1$-$C_4$alkoxy, or $C_1$-$C_4$alkyl, $A^{22}$ is hydrogen, halogen, $C_1$-$C_{12}$alkoxy, $C_1$-$C_{12}$alkyl, or $C_6$-$C_{10}$aryl, $A^{23}$ is hydrogen, halogen, $C_1$-$C_{12}$alkoxy, $C_1$-$C_{12}$alkyl, or $C_6$-$C_{10}$aryl, $A^{24}$ is hydrogen, halogen, $C_1$-$C_4$alkoxy, or $C_1$-$C_4$alkyl, or $A^{22}$ and $A^{23}$, or $A^{23}$ and $A^{24}$ together form a group

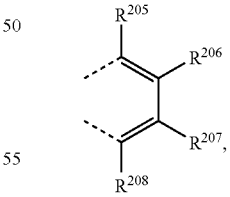

wherein $R^{205}$, $R^{206}$, $R^{207}$ and $R^{208}$ are independently of each other H, halogen, $C_1$-$C_{12}$alkoxy, or $C_1$-$C_{12}$alkyl, $R^{42}$ is H, halogen, $C_1$-$C_{12}$alkyl, $C_1$-$C_{12}$alkoxy, or $C_1$-$C_4$perfluoroalkyl, $R^{43}$ is H, halogen, $C_1$-$C_{12}$alkyl, $C_1$-$C_{12}$alkoxy, $C_1$-$C_4$perfluoroalkyl, $C_7$-$C_{15}$aralkyl, or $C_6$-$C_{10}$aryl, $R^{44}$ is H, halogen, $C_1$-$C_{12}$alkyl, $C_1$-$C_{12}$alkoxy, $C_6$-$C_{10}$aryl, $C_7$-$C_{15}$aralkyl, or $C_1$-$C_4$perfluoroalkyl, $R^{45}$ is H, halogen, $C_1$-$C_{12}$alkyl, $C_1$-$C_{12}$alkoxy, or $C_1$-$C_4$perfluoroalkyl;

d1) of formula

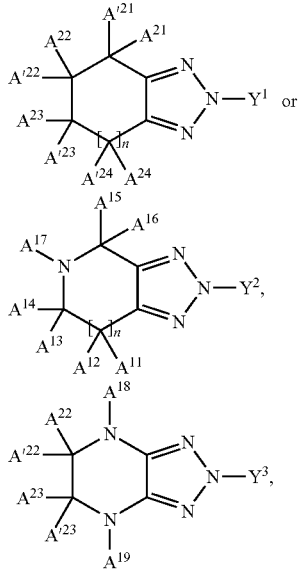

wherein n is 0, 1 or 2;

$A^{12}$, $A^{14}$, $A^{16}$, $A^{21}$, $A^{22}$, $A^{23}$, and $A^{24}$ are independently of each other hydrogen, CN, halogen, $C_1$-$C_{24}$alkyl, $C_1$-$C_{24}$alkoxy, $C_1$-$C_{24}$alkylthio, $C_1$-$C_{24}$perfluoroalkyl, $C_6$-$C_{18}$aryl, which is optionally substituted by G; —$NR^{25}R^{26}$, —$CONR^{25}R^{26}$, or —$COOR^{27}$, or $C_2$-$C_{10}$heteroaryl, which is optionally substituted by G; or $C_5$-$C_{12}$cycloalkyl, $C_5$-$C_{12}$cycloalkoxy, $C_5$-$C_{12}$cycloalkylthio, each of which is optionally substituted by G;

2 adjacent radicals $A^{14}$, $A^{17}$ or $A^{17}$, $A^{16}$, bonding to vicinal atoms, together are a group of formula

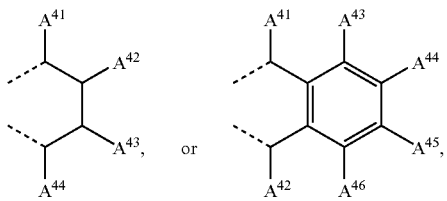

wherein $A^{41}$, $A^{42}$, $A^{43}$, $A^{44}$, $A^{45}$, and $A^{46}$ are independently of each other H, halogen, CN, $C_1$-$C_{24}$alkyl, $C_1$-$C_{24}$perfluoroalkyl, $C_1$-$C_{24}$alkoxy, $C_1$-$C_{24}$alkylthio, $C_6$-$C_{18}$aryl, which may optionally be substituted by G, —$NR^{25}R^{26}$, —$CONR^{25}R^{26}$, or —$COOR^{27}$, or $C_2$-$C_{10}$heteroaryl;

$A^{11}$, $A^{13}$, $A^{15}$, $A'^{21}$, $A'^{22}$, $A'^{23}$, and $A'^{24}$ are independently of each other is hydrogen or $C_1$-$C_{24}$alkyl;

or 2 adjacent radicals $A^{11}$, $A^{12}$; $A^{13}$, $A^{14}$; $A^{15}$, $A^{16}$; $A'^{21}$, $A^{21}$; $A'^{22}$, $A^{22}$; $A'^{23}$, $A^{23}$; $A'^{24}$, $A^{24}$, bonding to the same carbon atom, together are =O or =$NR^{25}$ or =N—$OR^{25}$ or =N—OH;

$R^{25}$ and $R^{26}$ are independently of each other $C_6$-$C_{18}$aryl, $C_7$-$C_{15}$aralkyl, or $C_1$-$C_{24}$alkyl, $R^{27}$ is $C_1$-$C_{24}$alkyl, $C_6$-$C_{18}$aryl, or $C_7$-$C_{18}$aralkyl;

or d2) of the formula

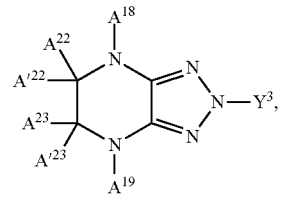

wherein $A'^{22}$ and $A'^{23}$ are independently of each other hydrogen or $C_1$-$C_{24}$alkyl;

2 adjacent radicals $A^{18}$, $A^{22}$ and $A^{23}$, $A^{19}$, bonding to vicinal atoms, together are a group of formula

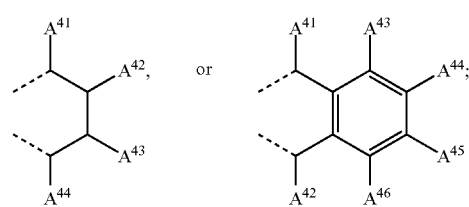

wherein $A^{41}$, $A^{42}$, $A^{43}$, $A^{44}$, $A^{45}$, and $A^{46}$ are independently of each other H, halogen, CN, $C_1$-$C_{24}$alkyl, $C_1$-$C_{24}$perfluoroalkyl, $C_1$-$C_{24}$alkoxy, $C_1$-$C_{24}$alkylthio, $C_6$-$C_{18}$aryl, which may optionally be substituted by G, —$NR^{25}R^{26}$, —$CONR^{25}R^{26}$, or —$COOR^{27}$, or $C_2$-$C_{10}$heteroaryl;

$R^{25}$ and $R^{26}$ are independently of each other $C_6$-$C_{18}$aryl, $C_7$-$C_{18}$aralkyl, or $C_1$-$C_{24}$alkyl, $R^{27}$ is $C_1$-$C_{24}$alkyl, $C_6$-$C_{18}$aryl, or $C_7$-$C_{18}$aralkyl; and for d1) and d2):

$Y^1$, $Y^2$ and $Y^3$ are independently of each other a group of formula

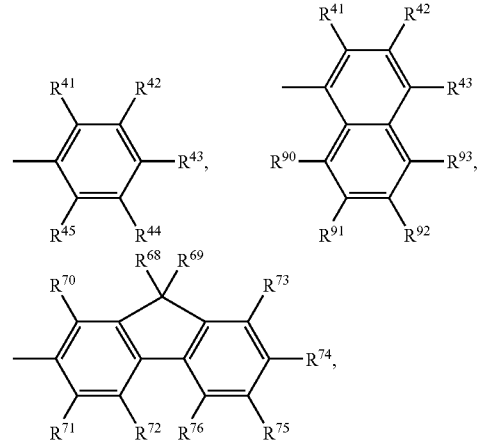

-continued

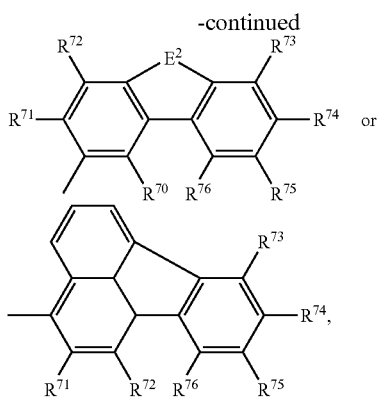

wherein
R$^{41}$ is the bond to M,
R$^{71}$ is the bond to M,
R$^{42}$ is hydrogen, C$_1$-C$_{24}$alkyl, CN, C$_1$-C$_{24}$alkyl, which is substituted by halogen, C$_6$-C$_{18}$-aryl, C$_6$-C$_{18}$-aryl substituted by C$_1$-C$_{12}$alkyl, or C$_1$-C$_8$alkoxy,
R$^{43}$ is hydrogen, CN, halogen, C$_1$-C$_{24}$alkyl substituted by F, C$_6$-C$_{18}$aryl, C$_6$-C$_{18}$aryl substituted by C$_1$-C$_{12}$alkyl, or C$_1$-C$_8$alkoxy, —CONR$^{25}$R$^{26}$, —COOR$^{27}$,

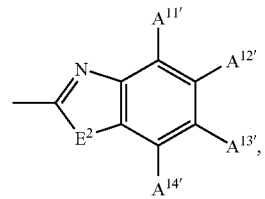

wherein
E$^2$ is —S—, —O—, or —NR$^{25'}$—, wherein R$^{25'}$ is C$_1$-C$_{24}$alkyl, or C$_6$-C$_{10}$aryl,
or
R$^{42}$ and R$^{43}$ are a group of formula

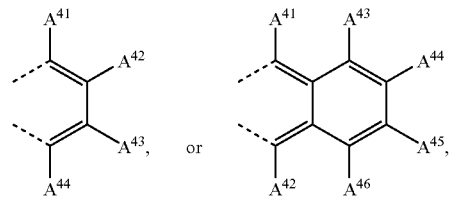

wherein A$^{41}$, A$^{42}$, A$^{43}$, A$^{44}$, A$^{45}$, and A$^{46}$ are independently of each other H, halogen, CN, C$_1$-C$_{24}$alkyl, C$_1$-C$_{24}$perfluoroalkyl, C$_1$-C$_{24}$alkoxy, C$_1$-C$_{24}$alkylthio, C$_6$-C$_{18}$aryl, which may optionally be substituted by G, —NR$^{25}$R$^{26}$, —CONR$^{25}$R$^{26}$, or —COOR$^{27}$, or C$_2$-C$_{10}$heteroaryl;
R$^{44}$ is hydrogen, CN, C$_1$-C$_{24}$alkyl, C$_1$-C$_{24}$alkyl substituted by F, halogen, C$_6$-C$_{18}$-aryl, C$_6$-C$_{18}$-aryl substituted by C$_1$-C$_{12}$ alkyl, or C$_1$-C$_8$alkoxy,
R$^{45}$ is hydrogen, CN, C$_1$-C$_{24}$alkyl, C$_1$-C$_{24}$alkyl substituted by F, halogen, C$_6$-C$_{18}$-aryl, C$_6$-C$_{18}$-aryl substituted by C$_1$-C$_{12}$alkyl, or C$_1$-C$_8$alkoxy,
A$^{11'}$, A$^{12'}$, A$^{13'}$ and A$^{14'}$ are independently of each other H, halogen, CN, C$_1$-C$_{24}$alkyl, C$_1$-C$_{24}$alkoxy, C$_1$-C$_{24}$alkylthio, —NR$^{25}$R$^{26}$, —CONR$^{25}$R$^{26}$, or —COOR$^{27}$, R$^{68}$ and R$^{69}$ are independently of each other C$_1$-C$_{24}$alkyl, which may be interrupted by one or two oxygen atoms,
R$^{70}$, R$^{72}$, R$^{73}$, R$^{74}$, R$^{75}$, R$^{76}$, R$^{90}$, R$^{91}$, R$^{92}$, and R$^{93}$ are independently of each other H, halogen, CN, C$_1$-C$_{24}$alkyl, C$_6$-C$_{10}$aryl, C$_1$-C$_{24}$alkoxy, C$_1$-C$_{24}$alkylthio, —NR$^{25}$, R$^{26}$, —CONR$^{25}$R$^{26}$, or —COOR$^{27}$, wherein R$^{25}$, R$^{26}$ and R$^{27}$ are as defined above and
G is C$_1$-C$_{18}$alkyl, —OR$^{305}$, —SR$^{305}$, —NR$^{305}$R$^{306}$, —CONR$^{305}$R$^{306}$, or —CN, wherein R$^{305}$ and R$^{306}$ are independently of each other C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl, or C$_1$-C$_{18}$alkyl which is interrupted by —O—; or R$^{305}$ and R$^{306}$ together form

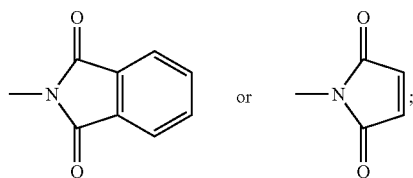

e) of formula

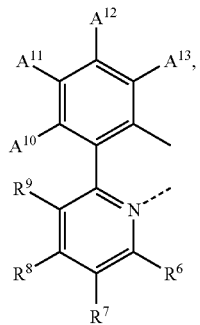

wherein
R$^6$ is hydrogen, halogen, nitro, C$_1$-C$_4$alkyl, C$_1$-C$_4$perfluoroalkyl, C$_1$-C$_4$alkoxy, or C$_6$-C$_{10}$aryl,
R$^7$ is hydrogen, halogen, C$_1$-C$_4$alkyl, C$_1$-C$_4$perfluoroalkyl, C$_6$-C$_{10}$aryl, C$_6$-C$_{10}$perfluoroaryl,
R$^8$ is hydrogen, C$_1$-C$_4$alkyl, C$_1$-C$_8$alkoxy, C$_1$-C$_4$perfluoroalkyl, C$_6$-C$_{10}$aryl, C$_6$-C$_{10}$perfluoroaryl,
R$^9$ is hydrogen, halogen, nitro, cyano, C$_1$-C$_4$alkyl, C$_1$-C$_4$perfluoroalkyl, C$_1$-C$_4$alkoxy, or C$_6$-C$_{10}$aryl,
A$^{10}$ is hydrogen, halogen, nitro, cyano, C$_1$-C$_4$alkyl, C$_2$-C$_4$alkenyl, C$_1$-C$_4$perfluoroalkyl, —O—C$_1$-C$_4$perfluoroalkyl, tri(C$_1$-C$_4$alkyl)silanyl, C$_6$-C$_{10}$aryl, or C$_6$-C$_{10}$perfluoroaryl,
A$^{11}$ is hydrogen, halogen, nitro, cyano, C$_1$-C$_4$alkyl, C$_2$-C$_4$alkenyl, C$_1$-C$_4$perfluoroalkyl, —O—C$_1$-C$_4$perfluoroalkyl, tri(C$_1$-C$_4$alkyl)silanyl, C$_6$-C$_{10}$aryl, or C$_6$-C$_{10}$perfluoroaryl,
A$^{12}$ is hydrogen, halogen, nitro, hydroxy, mercapto, amino, C$_1$-C$_4$alkyl, C$_2$-C$_4$alkenyl, C$_1$-C$_4$perfluoroalkyl, C$_1$-C$_4$alkoxy, —O—C$_1$-C$_4$perfluoroalkyl, —S—C$_1$-C$_4$alkyl, a group —(CH$_2$)$_r$X$^{20}$, wherein r is 1, or 2, X$^{20}$ is halogen, hydroxy, cyano, —O—C$_1$-C$_4$alkyl, di(C$_1$-C$_4$alkyl)amino, —CO$_2$X$^{21}$, wherein X$^{21}$ is H, or C$_1$-C$_4$alkyl; —CH═CHCO$_2$X$^{22}$, wherein X$^{22}$ is C$_1$-C$_4$alkyl; —CH(O), —SO$_2$X$^{23}$, —SOX$^{23}$, —NC(O)X$^{23}$, —NSO$_2$X$^{23}$, —NHX$^{23}$, —N(X$^{23}$)$_2$, wherein X$^{23}$ is $C_1$-$C_4$alkyl; tri($C_1$-$C_4$alkyl)siloxanyl, —O—$C_6$-$C_{10}$aryl, cyclohexyl, $C_6$-$C_{10}$aryl, or $C_6$-$C_{10}$perfluoroaryl, and $A^{13}$ is hydrogen, nitro, cyano, $C_1$-$C_4$alkyl, $C_2$-$C_4$alkenyl, $C_1$-$C_4$perfluoroalkyl, —O—$C_1$-$C_4$perfluoroalkyl, tri ($C_1$-$C_4$alkyl)silanyl, or $C_6$-$C_{10}$aryl.

6. Compound of claim 1, wherein n is an integer 1,

M is Co, Fe, Ir or Rh, and m is 2, or

M is Ni, Rh, Ru, Pd or Pt, and m is 1, $R_1$, $R_2$ independently are selected from H, unsubstituted or substituted $C_1$-$C_8$alkyl, unsubstituted or substituted phenyl, halogen, $C_1$-$C_8$alkoxy, COR, COOR, $SO_2R$, CN, NHR and NRR';

or the neighbouring residues $R_1$ and $R_2$ form an organic bridging group completing, together with the carbon atoms they are bonding to, an annellated phenyl ring, which optionally may be substituted;

$R_5$, $R_6$ independently are unsubstituted or substituted $C_1$-$C_8$alkyl, unsubstituted or substituted $C_2$-$C_8$alkenyl, unsubstituted or substituted phenyl;

$R_4$ is as defined for $R_5$ or is hydrogen;

$R_3$ is unsubstituted or substituted $C_1$-$C_8$alkyl, unsubstituted or substituted $C_2$-$C_8$alkenyl, unsubstituted or substituted phenyl; and any substituent, if present, is selected from halogen, $C_1$-$C_8$alkyl, $C_1$-$C_8$alkoxy, phenyl, phenyloxy, COR, OCOR, COOR, $SO_2R$, CN, NHR, NRR'; and R and R' independently are selected from $C_1$-$C_6$alkyl, and R may also be hydrogen;

$R_8$ is H, $SO_2$—$R_{11}$, CO—$R_{11}$, where $R_{11}$ is $C_1$-$C_{12}$alkyl, $C_1$-$C_{12}$haloalkyl, phenyl, phenyl substituted by halogen.

7. An organic electronic device comprising an emitting layer wherein the emitting layer comprises a compound according to claim 1.

8. The device of claim 7, further comprising a hole transport layer selected from polyvinyl-carbazol, N, N'-diphenyl-N, N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis (9H-carbazol-9-yl)cyclobutane (DCZB), N,N,N',N'-tetrakis (4-methylphenyl)-(1,1'-biphenyl)-4,4'-diamine (TTB), 4,4'-N,N-dicarbazole-biphenyl (CBP), N,N-dicarbazoyl-1,4-dimethene-benzene (DCB), porphyrinic compounds, and combinations thereof.

9. A compound of formula (III) or tautomeric forms thereof,

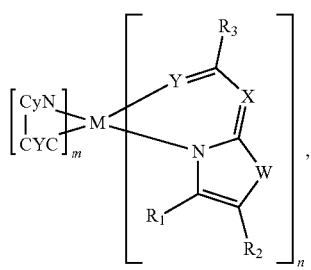

(III)

wherein

is a bidentate C,N-binding ligand, CyC and CyN are interlinked by a chemical bond, n is 1, M is Ir and m is 2 or M is Pt and m is 1; and wherein the moiety

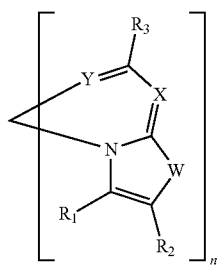

is selected from a group consisting of

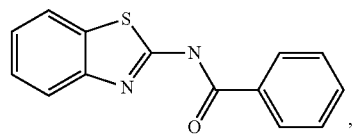

,

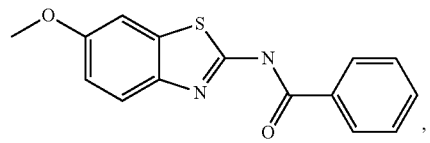

,

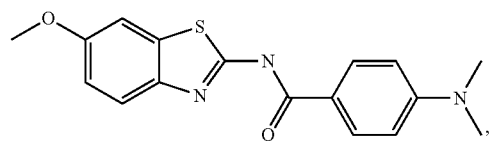

,

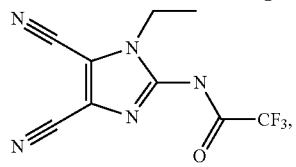

,

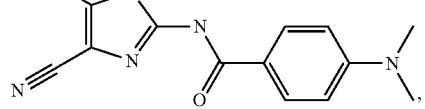

,

-continued

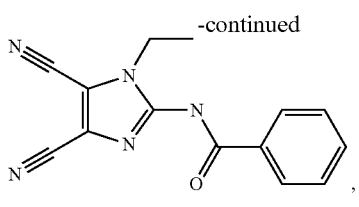

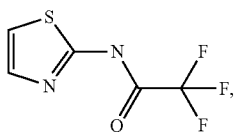

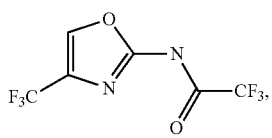

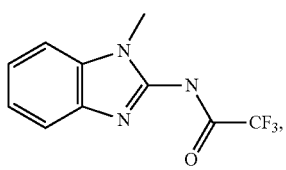

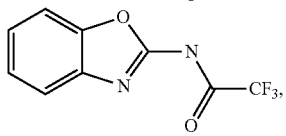

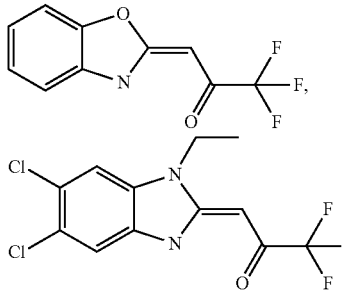

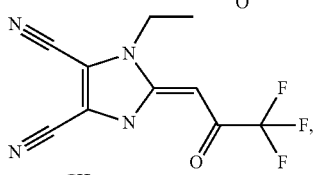

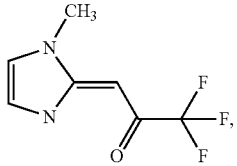

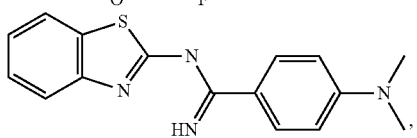 and

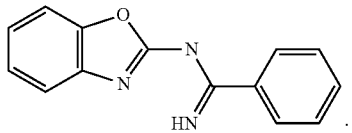.

10. Compound of claim 1, wherein formula (I') is

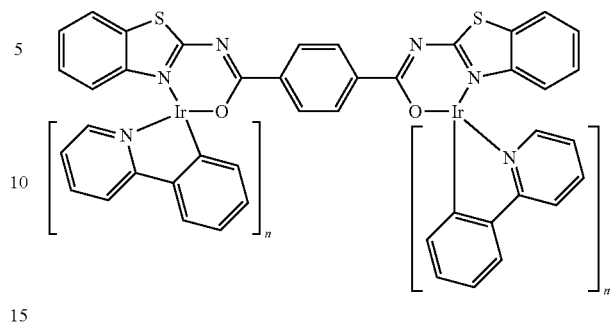

with n=2.

11. Compound of the formula I $$[LDH]_n M[L]_m \qquad (I),$$

wherein n is an integer 1,

M is Co, Fe, Ir, or Rh, and m is 2, or

M is Ni, Rh, Ru, Pd, or Pt, and m is 1,

LDH is a bidentate ligand of the formula II

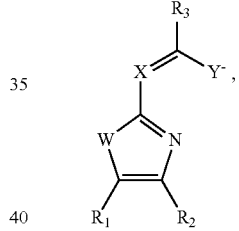

(II)

wherein

W is selected from O, S, $NR_4$, $CR_5R_6$,

X is N or CH,

Y is selected from O, S, $NR_8$;

$R_1$, $R_2$ independently are selected from H, unsubstituted or substituted $C_1$-$C_8$alkyl, unsubstituted or substituted phenyl, halogen, $C_1$-$C_8$alkoxy, COR, COOR, $SO_2R$, CN, NHR, NRR';

or the neighbouring residues $R_1$ and $R_2$ form an organic bridging group completing, together with the carbon atoms they are bonding to, an annellated phenyl ring, which optionally may be substituted;

$R_4$, $R_5$, $R_6$ independently are H, unsubstituted or substituted $C_1$-$C_8$alkyl, unsubstituted or substituted $C_2$-$C_8$alkenyl, unsubstituted or substituted phenyl;

$R_3$ is H, unsubstituted or substituted $C_1$-$C_8$alkyl, unsubstituted or substituted $C_2$-$C_8$alkenyl, unsubstituted or substituted phenyl; and any substituent, if present, is selected from halogen, $C_1$-$C_8$alkyl, $C_1$-$C_8$alkoxy, phenyl, phenyloxy, COR, OCOR, COOR, $SO_2R$, CN, NHR, NRR'; and R and R' independently are selected from $C_1$-$C_6$alkyl, and R may also be hydrogen;

$R_8$ is H, $SO_2-R_{11}$, $CO-R_{11}$, where $R_{ii}$ is $C_1-C_{12}$alkyl, $C_1-C_{12}$haloalkyl, phenyl, phenyl substituted by halogen; and L is a bidentate ligand and is selected from the ligands:
a) of formula

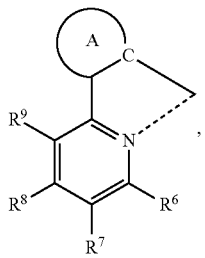

wherein $R^6$, $R^7$, $R^8$, and $R^9$ are independently of each other hydrogen, $C_1-C_{24}$alkyl, $C_2-C_{24}$alkenyl, $C_2-C_{24}$alkynyl, aryl, heteroaryl, $C_1-C_{24}$alkoxy, $C_1-C_{24}$alkylthio, cyano, acyl, alkyloxycarbonyl, a nitro group, or a halogen atom; or two $R^6$, $R^7$, $R^8$, and $R^9$, which are adjacent to each other, together form a group

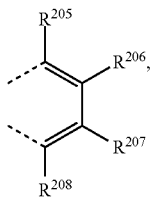

wherein $R^{205}$, $R^{206}$, $R^{207}$ and $R^{208}$ are independently of each other H, or $C_1-C_8$alkyl, the ring A represents an optionally substituted aryl or heteroaryl group; or the ring A may be taken with the pyridyl group binding to the ring A to form a ring; the alkyl group, alkenyl group, alkynyl group, aryl group, heteroaryl group, alkoxy group, alkylthio group, acyl group, and alkyloxycarbonyl group represented by $R^6$, $R^7$, $R^8$, and $R^9$ may be substituted;

b) of the formula

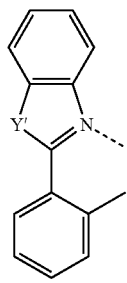

wherein Y' is S, O, $NR^{200}$, wherein
$R^{200}$ is hydrogen, cyano, $C_1-C_4$alkyl, $C_2-C_4$alkenyl, optionally substituted $C_6-C_{10}$aryl, $-(CH_2)_r-Ar$ wherein Ar is an optionally substituted $C_6-C_{10}$aryl, a group $-(CH_2)_rX^{20}$, wherein r' is an integer of 1 to 5, $X^{20}$ is halogen, hydroxy, $-O-C_1-C_4$alkyl, $di(C_1-C_4$alkyl)amino, amino, or cyano; a group $-(CH_2)_rOC(O)(CH_2)_{r''}CH_3$, wherein r is 1, or 2, and r'' is 0, or 1;

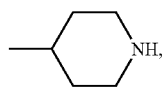

$-NH-Ph$, $-C(O)CH_3$, $-CH_2-O-(CH_2)_2-Si(CH_3)_3$, or

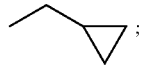

c) of the formula

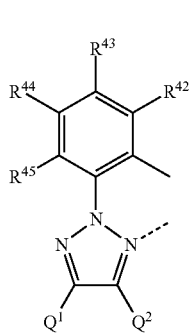 or 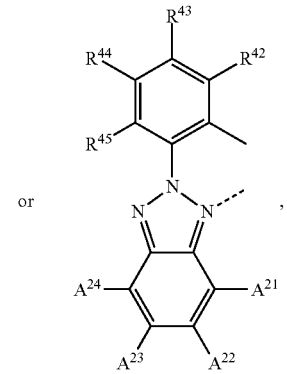

wherein
$Q^1$ and $Q^2$ are independently of each other hydrogen, $C_1-C_{24}$alkyl, or $C_6-C_{18}$aryl, $A^{21}$ is hydrogen, halogen, $C_1-C_4$alkoxy, or $C_1-C_4$alkyl, $A^{22}$ is hydrogen, halogen, $C_1-C_{12}$alkoxy, $C_1-C_{12}$alkyl, or $C_6-C_{10}$aryl, $A^{23}$ is hydrogen, halogen, $C_1-C_{12}$alkoxy, $C_1-C_{12}$alkyl, or $C_6-C_{10}$aryl, $A^{24}$ is hydrogen, halogen, $C_1-C_4$alkoxy, or $C_1-C_4$alkyl, or $A^{22}$ and $A^{23}$, or $A^{23}$ and $A^{24}$ together form a group

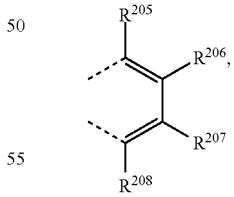

wherein $R^{205}$, $R^{206}$, $R^{207}$ and $R^{208}$ are independently of each other H, halogen, $C_1-C_{12}$alkoxy, or $C_1-C_{12}$alkyl, $R^{42}$ is H, halogen, $C_1-C_{12}$alkyl, $C_1-C_{12}$alkoxy, or $C_1-C_4$perfluoroalkyl, $R^{43}$ is H, halogen, $C_1-C_{12}$alkyl, $C_1-C_{12}$alkoxy, $C_1-C_4$perfluoroalkyl, $C_7-C_{15}$aralkyl, or $C_6-C_{10}$aryl, $R^{44}$ is H, halogen, $C_1-C_{12}$alkyl, $C_1-C_{12}$alkoxy, $C_6-C_{10}$aryl, $C_7-C_{15}$aralkyl, or $C_1-C_4$perfluoroalkyl, $R^{45}$ is H, halogen, $C_1$-$C_{12}$alkyl, $C_1$-$C_{12}$alkoxy, or $C_1$-$C_4$perfluoroalkyl;

d1) of the formula

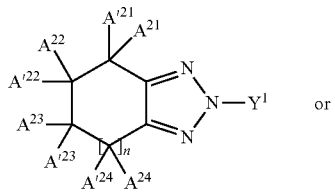

or

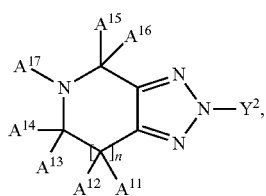

wherein n is 0, 1 or 2, $A^{12}, A^{14}, A^{16}, A^{21}, A^{22}, A^{23}$, and $A^{24}$ are independently of each other hydrogen, CN, halogen, $C_1$-$C_{24}$alkyl, $C_1$-$C_{24}$alkoxy, $C_1$-$C_{24}$alkylthio, $C_1$-$C_{24}$perfluoroalkyl, $C_6$-$C_{18}$aryl, which is optionally substituted by G; —$NR^{25}R^{26}$, —$CONR^{25}R^{26}$, or —$COOR^{27}$, or $C_2$-$C_{10}$heteroaryl, which is optionally substituted by G; or $C_5$-$C_{12}$cycloalkyl, $C_5$-$C_{12}$cycloalkoxy, $C_5$-$C_{12}$cycloalkylthio, each of which is optionally substituted by G;

2 adjacent radicals $A^{14}, A^{17}$ or $A^{17}, A^{16}$, bonding to vicinal atoms, together are a group of formula

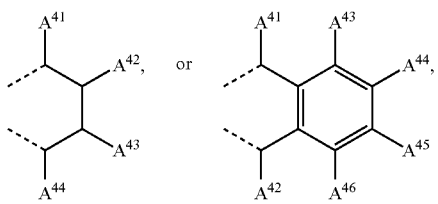

wherein $A^{41}, A^{42}, A^{43}, A^{44}, A^{45}$, and $A^{46}$ are independently of each other H, halogen, CN, $C_1$-$C_{24}$alkyl, $C_1$-$C_{24}$perfluoroalkyl, $C_1$-$C_{24}$alkoxy, $C_1$-$C_{24}$alkylthio, $C_6$-$C_{18}$aryl, which may optionally be substituted by G, —$NR^{25}R^{26}$, —$CONR^{25}R^{26}$, or —$COOR^{27}$, or $C_2$-$C_{10}$heteroaryl;

$A^{11}, A^{13}, A^{15}, A^{'21}, A^{'22}, A^{'23}$ and $A^{'24}$ are independently of each other hydrogen or $C_1$-$C_{24}$alkyl;

or 2 adjacent radicals $A^{11}, A^{12}; A^{13}, A^{14}; A^{15}, A^{16}; A^{'21}, A^{21}; A^{'22}, A^{22}; A^{'23}, A^{23}; A^{'24}, A^{24}$, bonding to the same carbon atom, together are =O or =$NR^{25}$ or =N—$OR^{25}$ or =N—OH;

$R^{25}$ and $R^{26}$ are independently of each other $C_6$-$C_{18}$aryl, $C_7$-$C_{18}$aralkyl, or $C_1$-$C_{24}$alkyl, $R^{27}$ is $C_1$-$C_{24}$alkyl, $C_6$-$C_{18}$aryl, or $C_7$-$C_{18}$aralkyl;

or d2) of the formula

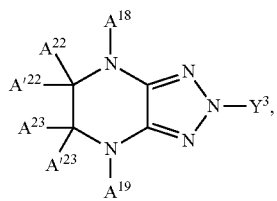

wherein $A^{'22}$ and $A^{'23}$ are independently of each other hydrogen or $C_1$-$C_{24}$alkyl;

2 adjacent radicals $A^{18}, A^{22}$ and $A^{23}, A^{19}$, bonding to vicinal atoms, together are a group of formula

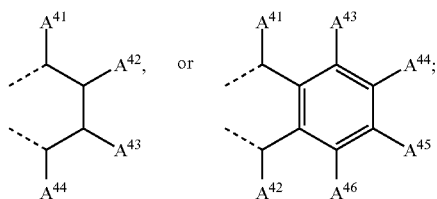

wherein $A^{41}, A^{42}, A^{43}, A^{44}, A^{45}$, and $A^{46}$ are independently of each other H, halogen, CN, $C_1$-$C_{24}$alkyl, $C_1$-$C_{24}$perfluoroalkyl, $C_1$-$C_{24}$alkoxy, $C_1$-$C_{24}$alkylthio, $C_6$-$C_{18}$aryl, which may optionally be substituted by G, —$NR^{25}R^{26}$, —$CONR^{25}R^{26}$, or —$COOR^{27}$, or $C_2$-$C_{10}$heteroaryl;

$R^{25}$ and $R^{26}$ are independently of each other $C_6$-$C_{18}$aryl, $C_7$-$C_{18}$aralkyl, or $C_1$-$C_{24}$alkyl, $R^{27}$ is $C_1$-$C_{24}$alkyl, $C_6$-$C_{18}$aryl, or $C_7$-$C_{18}$aralkyl; and for d1) and d2):

$Y^1, Y^2$ and $Y^3$ are independently of each other a group of formula

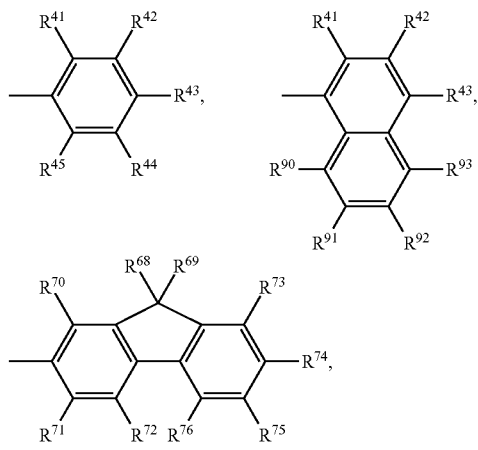

-continued

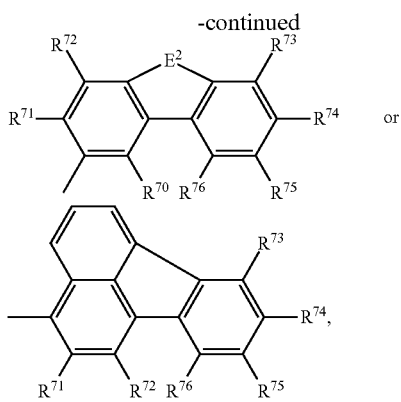

wherein
R⁴¹ is the bond to M,
R⁷¹ is the bond to M,
R⁴² is hydrogen, or $C_1$-$C_{24}$alkyl, CN, $C_1$-$C_{24}$alkyl, which is substituted by halogen, $C_6$-$C_{18}$-aryl, $C_6$-$C_{18}$-aryl substituted by $C_1$-$C_{12}$alkyl, or $C_1$-$C_8$alkoxy,
R⁴³ is hydrogen, CN, halogen, $C_1$-$C_{24}$alkyl substituted by F, $C_6$-$C_{18}$aryl, $C_6$-$C_{18}$aryl substituted by $C_1$-$C_{12}$alkyl, or $C_1$-$C_8$alkoxy, —CONR²⁵R²⁶, —COOR²⁷,

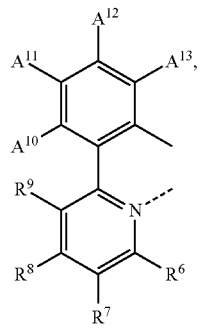

wherein
E² is —S—, —O—, or —NR²⁵'—, wherein R²⁵' is $C_1$-$C_{24}$alkyl, or $C_6$-$C_{10}$aryl,
or R⁴² and R⁴³ are a group of formula

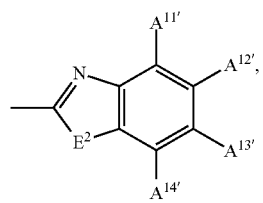

wherein A⁴¹, A⁴², A⁴³, A⁴⁴, A⁴⁵, and A⁴⁶ are independently of each other H, halogen, CN, $C_1$-$C_{24}$alkyl, $C_1$-$C_{24}$perfluoroalkyl, $C_1$-$C_{24}$alkoxy, $C_1$-$C_{24}$alkylthio, $C_6$-$C_{18}$aryl, which may optionally be substituted by G, —NR²⁵R²⁶, —CONR²⁵R²⁶, or —COOR²⁷, or $C_2$-$C_{10}$heteroaryl;
R⁴⁴ is hydrogen, CN or $C_1$-$C_{24}$alkyl, $C_1$-$C_{24}$alkyl substituted by F, halogen, $C_6$-$C_{18}$-aryl, $C_6$-$C_{18}$-aryl substituted by $C_1$-$C_{12}$ alkyl, or $C_1$-$C_8$alkoxy,
R⁴⁵ is hydrogen, CN or $C_1$-$C_{24}$alkyl, $C_1$-$C_{24}$alkyl substituted by F, halogen, $C_6$-$C_{18}$-aryl, $C_6$-$C_{18}$-aryl substituted by $C_1$-$C_{12}$alkyl, or $C_1$-$C_8$alkoxy,
A¹¹', A¹²', A¹³', and A¹⁴' are independently of each other H, halogen, CN, $C_1$-$C_{24}$alkyl, $C_1$-$C_{24}$alkoxy, $C_1$-$C_{24}$alkylthio, —NR²⁵R²⁶, —CONR²⁵R²⁶, or —COOR²⁷, R⁶⁸ and R⁶⁹ are independently of each other $C_1$-$C_{24}$alkyl, which may be interrupted by one or two oxygen atoms,
R⁷⁰, R⁷², R⁷³, R⁷⁴, R⁷⁵, R⁷⁶, R⁹⁰, R⁹¹, R⁹², and R⁹³ are independently of each other H, halogen, CN, $C_1$-$C_{24}$alkyl, $C_6$-$C_{10}$aryl, $C_1$-$C_{24}$alkoxy, $C_1$-$C_{24}$alkylthio, —NR²⁵R²⁶, —CONR²⁵R²⁶, or —COOR²⁷, wherein R²⁵, R²⁶ and R²⁷ are as defined above and
G is $C_1$-$C_{18}$alkyl, —OR³⁰⁵, —SR³⁰⁵, —NR³⁰⁵R³⁰⁶, —CONR³⁰⁵R³⁰⁶, or —CN, wherein R³⁰⁵ and R³⁰⁶ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—; or R³⁰⁵ and R³⁰⁶ together form a five or six membered ring;

e) of formula

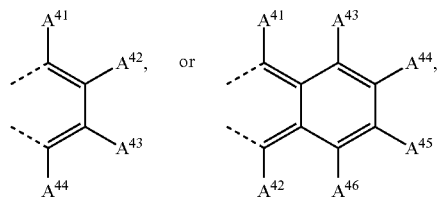

wherein R⁶ is hydrogen, halogen, nitro, $C_1$-$C_4$alkyl, $C_1$-$C_4$perfluoroalkyl, $C_1$-$C_4$alkoxy, or optionally substituted $C_6$-$C_{10}$aryl,
R⁷ is hydrogen, halogen, $C_1$-$C_4$alkyl, $C_1$-$C_4$perfluoroalkyl, optionally substituted $C_6$-$C_{10}$aryl, or optionally substituted $C_6$-$C_{10}$perfluoroaryl,
R⁸ is hydrogen, $C_1$-$C_4$alkyl, $C_1$-$C_8$alkoxy, $C_1$-$C_4$perfluoroalkyl, optionally substituted $C_6$-$C_{10}$aryl, or optionally substituted $C_6$-$C_{10}$perfluoroaryl,
R⁹ is hydrogen, halogen, nitro, cyano, $C_1$-$C_4$alkyl, $C_1$-$C_4$perfluoroalkyl, $C_1$-$C_4$alkoxy, or optionally substituted $C_6$-$C_{10}$aryl,
A¹⁰ is hydrogen, halogen, nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, optionally substituted $C_6$-$C_{10}$aryl, or optionally substituted $C_6$-$C_{10}$perfluoroaryl,
A¹¹ is hydrogen, halogen, nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, optionally substituted $C_6$-$C_{10}$aryl, or optionally substituted $C_6$-$C_{10}$perfluoroaryl,
A¹² is hydrogen, halogen, nitro, hydroxy, mercapto, amino, $C_1$-$C_4$alkyl, $C_2$-$C_4$alkenyl, $C_1$-$C_4$perfluoroalkyl, $C_1$-$C_4$alkoxy, —O—$C_1$-$C_4$perfluoroalkyl, —S—$C_1$-$C_4$alkyl, a group —(CH₂)ᵣX²⁰, wherein r is 1, or 2, X²⁰ is halogen, hydroxy, cyano, —O—$C_1$-$C_4$alkyl, di($C_1$-$C_4$alkyl)amino, —CO₂X²¹, wherein X²¹ is H, or $C_1$-$C_4$alkyl; —CH=CHCO₂X²², wherein X²² is $C_1$-$C_4$alkyl; —CH(O), —SO₂X²³, —SOX²³, —NC(O)X²³, —NSO₂X²³, —NHX²³, —N(X²³)₂, wherein X²³ is $C_1$-$C_4$alkyl; tri($C_1$-$C_4$alkyl)siloxanyl, optionally substituted —O—$C_6$-$C_{10}$aryl, cyclohexyl, optionally substituted $C_6$-$C_{10}$aryl, or optionally substituted $C_6$-$C_{10}$perfluoroaryl, and $A^{13}$ is hydrogen, nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, or optionally substituted $C_6$-$C_{10}$aryl.

12. The compound according to claim 11, wherein
n is an integer 1,
M is Ir, or Rh, and
m is 2.

13. The compound according to claim 11, wherein
n is an integer 1,
M is Pd, or Pt, and
m is 1.

14. The compound according to claim 11, wherein L is a ligand of formula

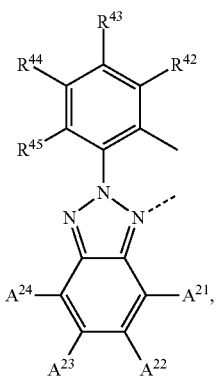

wherein
$A^{21}$, $A^{22}$, $A^{23}$, $A^{24}$, $R^{42}$, $R^{43}$, $R^{44}$ and $R^{45}$ are as defined for c) in claim 11.

15. The compound according to claim 11, which is a compound of formula

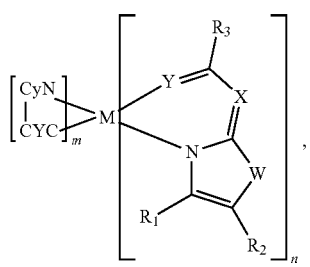

(III)

wherein

is a bidentate ligand L,
L is as defined in claim 11,
n is 1,
M is Ir and m is 2, or
M is Pt and m is 1;
W is O, S, $NR_4$, $CR_5R_6$,
X is N or CH,
Y is O or $NR_8$;
$R_1$, $R_2$ independently are selected from H, $C_1$-$C_8$alkyl, phenyl, halogen, $C_1$-$C_8$alkoxy, CN, NHR, NRR';
or $R_1$ and $R_2$ together with the carbon atoms they are bonding to form an annellated phenyl ring, which optionally may be substituted;
$R_3$ is H, unsubstituted or substituted $C_1$-$C_8$alkyl, unsubstituted or substituted $C_2$-$C_8$alkenyl, unsubstituted or substituted phenyl;
$R_4$, $R_5$, $R_6$ independently are H or $C_1$-$C_8$alkyl;
$R_8$ is H, $SO_2$—$R_{11}$, CO—$R_{11}$, where $R_{11}$ is $C_1$-$C_{12}$alkyl, $C_1$-$C_{12}$haloalkyl, phenyl, phenyl substituted by halogen; and
any substituent, if present, is selected from halogen, $C_1$-$C_8$alkyl, $C_1$-$C_8$alkoxy, COR, NHR, NRR'; and
R and R' independently are selected from $C_1$-$C_6$alkyl, and R may also be hydrogen.

16. An organic electronic device comprising an emitting layer wherein the emitting layer comprises a compound according to claim 11.

17. The organic electronic device according to claim 16, which is an organic light emitting diode.

18. The device of claim 17, further comprising a hole transport layer selected from the group consisting of polyvinyl-carbazol, N, N'-diphenyl-N, N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-4)-(diethylamino)phenyl]pyrazoline (PPR or DEASP), 1,2-trans-bis (9H-carbazol-9-yl)cyclobutane (DCZB), N,N,N',N'-tetrakis (4-methylphenyl)-(1,1'-biphenyl)-4,4'-diamine (TTB), 4,4'-N,N-dicarbazole-biphenyl (CBP), N,N-dicarbazoyl-1,4-dimethene-benzene (DCB), porphyrinic compounds, and combinations thereof.

19. A stationary display or a mobile display comprising the organic light emitting diode according to claim 17.

20. A method of using the compound according to claim 11 in an electronic device comprising:
adding the compound according to claim 11 in an emitting layer in the electronic device.

* * * * *